US 8,492,377 B2

(12) United States Patent
Papanikos et al.

(10) Patent No.: US 8,492,377 B2
(45) Date of Patent: Jul. 23, 2013

(54) MTKI QUINAZOLINE DERIVATIVES

(75) Inventors: Alexandra Papanikos, Berchem (BE); Eddy Jean Edgard Freyne, Rumst (BE); Peter Ten Holte, Beerse (BE); Marc Willems, Vosselaar (BE); Werner Constant Johan Embrechts, Beerse (BE); Laurence Anne Mevellec, Louviers (FR); Pierre-Henri Storck, Rouen (FR)

(73) Assignee: Janssen Pharmaceutica NV, Beerse (BE)

( * ) Notice: Subject to any disclaimer, the term of this patent is extended or adjusted under 35 U.S.C. 154(b) by 414 days.

(21) Appl. No.: 12/373,404

(22) PCT Filed: Jul. 12, 2007

(86) PCT No.: PCT/EP2007/057200
§ 371 (c)(1),
(2), (4) Date: Jan. 12, 2009

(87) PCT Pub. No.: WO2008/006884
PCT Pub. Date: Jan. 17, 2008

(65) Prior Publication Data
US 2010/0029627 A1    Feb. 4, 2010

(30) Foreign Application Priority Data
Jul. 13, 2006  (EP) .................................. 06117185

(51) Int. Cl.
*A61K 31/54*     (2006.01)
*A61K 31/535*    (2006.01)
*A61K 31/497*    (2006.01)
*C07D 471/04*    (2006.01)

(52) U.S. Cl.
USPC ................ 514/228.5; 514/232.8; 514/252.16; 514/257

(58) Field of Classification Search
USPC ..................................... 514/228.5
See application file for complete search history.

(56) References Cited

U.S. PATENT DOCUMENTS

| | | | |
|---|---|---|---|
| 4,067,726 A | 1/1978 | Sasse et al. |
| 4,160,836 A | 7/1979 | Vandenberk et al. |
| 4,442,278 A | 4/1984 | Giants |
| 5,679,683 A | 10/1997 | Bridges et al. |
| 5,721,237 A | 2/1998 | Myers et al. |
| 5,770,599 A | 6/1998 | Gibson |
| 5,821,240 A | 10/1998 | Himmelsbach et al. |
| 6,002,008 A | 12/1999 | Wissner et al. |
| 6,265,410 B1 | 7/2001 | Bridges et al. |
| 6,288,082 B1 | 9/2001 | Wissner et al. |
| 6,344,459 B1 | 2/2002 | Bridges et al. |
| 6,414,148 B1 | 7/2002 | Thomas et al. |
| 6,521,620 B1 | 2/2003 | Bridges et al. |
| 6,602,863 B1 | 8/2003 | Bridges et al. |
| 6,794,395 B1 | 9/2004 | Roth et al. |
| 7,067,507 B2 | 6/2006 | Pulley et al. |
| 7,312,225 B2 | 12/2007 | Luecking et al. |
| 7,648,975 B2 | 1/2010 | Freyne et al. |
| 7,655,642 B2 | 2/2010 | Freyne et al. |
| 7,799,772 B2 | 9/2010 | Freyne et al. |
| RE42,353 E | 5/2011 | Thomas et al. |
| 2002/0173646 A1 | 11/2002 | Thomas et al. |
| 2003/0087908 A1 | 5/2003 | Geuns-Meyer et al. |
| 2003/0186987 A1 | 10/2003 | Bridges et al. |
| 2004/0048880 A1 | 3/2004 | Himmelsbach et al. |
| 2004/0116388 A1 | 6/2004 | Armistead et al. |

(Continued)

FOREIGN PATENT DOCUMENTS

| | | |
|---|---|---|
| GB | 807899 A | 1/1959 |
| GB | 1465451 A | 2/1977 |

(Continued)

OTHER PUBLICATIONS

Anderson (Chem and Biol 10:787-797, 2003).*

(Continued)

*Primary Examiner* — Craig Ricci
(74) *Attorney, Agent, or Firm* — Philip S. Johnson

(57) ABSTRACT

The present invention concerns the compounds of formula (I)

the N-oxide forms, the pharmaceutically acceptable addition salts and the stereochemically isomeric forms thereof, wherein
Y represents —$C_{3-9}$alkyl-, —$C_{1-5}$alkyl-$NR^6$—$C_{1-5}$alkyl- or —$C_{1-5}$alkyl-$NR^7$—CO—$C_{1-5}$alkyl-;
$X^1$ represents —O—;
$X^2$ represents $NR^5$—$C_{1-2}$alkyl-;
$R^1$ represents hydrogen, halo or $Het^3$-O—;
$R^2$ represents hydrogen;
$R^3$ represents hydroxy, $C_{1-4}$alkyloxy- or $C_{1-4}$alkyloxy substituted with one or two substituents each independently selected from $Het^4$, hydroxy, $C_{1-4}$alkyloxy-, $C_{1-4}$alkyloxy-$C_{1-4}$alkyloxy and $NR^9R^{10}$;
$R^5$ represents hydrogen or $C_{1-4}$alkyl;
$R^6$ represents hydrogen or $C_{1-4}$alkyl;
$R^7$ represents hydrogen;
$R^9$ and $R^{10}$ each independently represent hydrogen; $C_{1-4}$alkyl-S(=O)$_2$—$C_{1-4}$alkyl-C(=O)—; $C_{1-4}$alkyl or $C_{1-4}$alkyl substituted with hydroxy;
$Het^3$ represents pyridinyl optionally substituted with $C_{1-4}$alkyl;
$Het^4$ represents morpholinyl, piperidinyl or piperazinyl wherein said $Het^4$ is optionally substituted with hydroxy-$C_{1-4}$alkyl or $C_{1-4}$alkyl-S(=O)$_2$—$C_{1-4}$alkyl-.

15 Claims, No Drawings

U.S. PATENT DOCUMENTS

| | | | |
|---|---|---|---|
| 2005/0009867 | A1 | 1/2005 | Hennequin |
| 2005/0250797 | A1 | 11/2005 | Hennequin et al. |
| 2007/0078132 | A1 | 4/2007 | Freyne et al. |
| 2008/0219975 | A1 | 9/2008 | Perera et al. |
| 2009/0075999 | A1 | 3/2009 | Blanchard et al. |
| 2010/0029627 | A1 | 2/2010 | Papanikos et al. |
| 2010/0069424 | A1 | 3/2010 | Freyne et al. |
| 2010/0105668 | A1 | 4/2010 | Freyne et al. |
| 2010/0152174 | A1 | 6/2010 | Freyne et al. |
| 2010/0160310 | A1 | 6/2010 | Freyne et al. |
| 2010/0173913 | A1 | 7/2010 | Freyne |
| 2010/0190786 | A1 | 7/2010 | Diels et al. |
| 2010/0204197 | A1 | 8/2010 | Diels et al. |
| 2010/0222574 | A1 | 9/2010 | Rombouts et al. |
| 2011/0009404 | A1 | 1/2011 | Buijnsters et al. |

FOREIGN PATENT DOCUMENTS

| | | | |
|---|---|---|---|
| GB | 1542514 | A | 3/1979 |
| WO | WO-95/19774 | A1 | 7/1995 |
| WO | WO-96/07657 | A1 | 3/1996 |
| WO | WO-96/09294 | A1 | 3/1996 |
| WO | WO-96/33980 | A1 | 10/1996 |
| WO | WO-96/39145 | A1 | 12/1996 |
| WO | WO-97/32880 | A1 | 9/1997 |
| WO | WO-97/38983 | A1 | 10/1997 |
| WO | WO-98/13354 | A1 | 4/1998 |
| WO | WO-98/43960 | A1 | 10/1998 |
| WO | WO-99/33792 | A2 | 7/1999 |
| WO | WO-99/33793 | A2 | 7/1999 |
| WO | WO-99/33795 | A1 | 7/1999 |
| WO | WO-99/33815 | A1 | 7/1999 |
| WO | WO-00/018761 | A1 | 4/2000 |
| WO | WO-00/055159 | A2 | 9/2000 |
| WO | WO-01/016130 | A1 | 3/2001 |
| WO | WO-02/020479 | A1 | 3/2002 |
| WO | WO-02/083654 | A1 | 10/2002 |
| WO | WO-03/072062 | A2 | 9/2003 |
| WO | WO-03/082290 | A1 | 10/2003 |
| WO | WO-2004/004732 | A1 | 1/2004 |
| WO | WO-2004/009562 | A1 | 1/2004 |
| WO | WO-2004/014899 | A1 | 2/2004 |
| WO | WO-2004/026829 | A2 | 4/2004 |
| WO | WO-2004/026881 | A1 | 4/2004 |
| WO | WO-2004/037814 | A1 | 5/2004 |
| WO | WO-2004/043936 | A1 | 5/2004 |
| WO | WO-2004/074224 | A1 | 9/2004 |
| WO | WO-2004/078682 | A2 | 9/2004 |
| WO | WO-2004/105765 | A1 | 12/2004 |
| WO | WO-2005/058318 | A1 | 6/2005 |
| WO | WO-2005/058913 | A1 | 6/2005 |
| WO | WO-2006/061415 | A1 | 6/2006 |
| WO | WO-2006/061417 | A2 | 6/2006 |
| WO | WO-2007/003525 | A2 | 1/2007 |
| WO | WO-2007/058267 | A1 | 5/2007 |
| WO | WO-2007/058627 | A1 | 5/2007 |
| WO | WO-2007/058628 | A1 | 5/2007 |
| WO | WO-2008/006884 | A2 | 1/2008 |
| WO | WO-2008/049902 | A2 | 5/2008 |
| WO | WO-2008/155421 | A2 | 12/2008 |
| WO | WO-2009/016132 | A1 | 2/2009 |
| WO | WO-2009/112439 | A1 | 9/2009 |

OTHER PUBLICATIONS

Thiel (Nature Biotechnol 2:513-519, 2004).*
Mackay et al (J Clin Oncol 28(suppl): abstract e14544, 2010).*
Abe et al., "Fyn kinases-mediated phosphorylation of NMDA receptor NR2B subunit at Tyr1472 is essential for maintenance of neuropathic pain" *Eur J Neurosci*, 2005; 22(6):1445-1454.
Bolen et al., "Nonreceptor tyrosine protein kinases" *Oncogene*, 1993; 8(8):2025-2031.
Boyce et al., "Requirement of pp60$^{c\text{-}src}$ Expression for Osteoclasts to Form Ruffled Borders and Resorb Bone in Mice" *J.Clin. Invest.*, 1992; 90:1622-1627.
Bradshaw, "Cell transformation: the role of oncogenes and factors" *Mutagenesis*, 1986; 1(2):91-97.
Brown et al., "Regulation, substrates and functions of src" *Biochimica et Biophysica Acta*, 1996; 1287(2-3):121-149.
Brunton et al., "A role for epidermal growth factor receptor, c-Src and focal adhesion kinase in an in vitro model for the progression of colon cancer" *Oncogene*, 1997; 14:283-293.
Cartwright et al., "Activation of the pp60$^{c\text{-}src}$ protein kinase in an early event in colonic carcinogenesis" *Proc. Natl. Acad. Sci.*, 1990; 87(2):558-562.
Courtneidge et al., "Protein tyrosine kinases, with emphasis on the Src family" *Semin. Cancer Biol.*, 1994; 5(4):239-246.
Davies et al., "Specificity and mechanism of Action of Some Commonly Used Protein Kinase Inhibitors," *Biochemical Society*, 2000; 351:95-105.
Druker et al., "Lessons learned from the development of an Abl tyrosine kinase ihibitor for chronic myelogenous leukemia," *J. Clin. Invest.*, 2000; 105(1):3-7.
Fanning et al., "Elevated Expression of pp60$^{c\text{-}src}$ in Low Grade Human Bladder Carcinomas" *Cancer Research*, 1992; 52:1457-1462.
Gennaro et al., "Remington's Pharmaceutical Sciences" 18th ed., *mack publishing Co.*, (see especially Part 8: Pharmaceutical preparations and their Manufacture, 1990.
Greene et al., "Protective Groups in Organic Synthesis," *John Wiley & Sons*, 3$^{rd}$ Ed1999.
Hanks et al., "Signaling through focal adhesion kinase" *BioEssays*, 1997; 19(2):137-145.
Jankowski et al., "Oncogenes and onco-suppressor gene in adenocarcinoma of the oesophagus" *Gut*, 1992; 33:1033-1038.
Klinghoffer et al., "Src family kinases are required for integrin but not PDGFR signal transduction" *EMBO Journal*, 1999; 18(9):2459-2471.
Larson et al., "Chapter 13. New Approaches to Antitumor Therapy", *Ann. Reports in Med. Chem.*, 1989; 24(13):121-128.
Lauffenburger et al., "Cell Migration: A Physically Integrated Molecular Process", *Cell*, 1996; 84:359-369.
Lutz et al., "Overexpression and Activation of the Tyrosine Kinase Src in Human Pancreatic Carcinoma" *Biochem. and Biophys. Res. Comm.*, 1998; 243(2):503-508.
Mao et al., "Activation of c-Src by receptor tyrosine kinases in human colon cancer cells with high metastatic potential" *Oncongene*, 1997; 15:3083-3090.
Mazurenko et al., "Expression of pp60$^{c\text{-}src}$ in human small cell and non-small cell lung carcinomas" *European Journal of Cancer*, 1992; 28(2/3):372-377.
Muthuswamy et al., "Activation of Src family kinases in Neu-induced mammary tumors correlates with their asociation with distinct sets of tyrosine phosphorylated proteins in vivo" *Oncogene*, 1995; 11(9):1801-1810.
Owens et al., "The catalytic activity of the Src family kinases is required to disrupt cadherin-dependent cell-cell contacts" *Molecular Biology of the Cell*, 2000; 11(1):51-64.
Parsons et al., "Src family protein tyrosine kinases: cooperating with growth factor and adhesion signaling pathways" *Current Opinion in Cell Biology*, 1997; 9(2):187-192.
Schlaepfer et al., "Signaling through focal adhesion kinase" *Progress in Biophysics and Molecular Biology*, 1999; 71(3-4):435-478.
Shawver et al, "Smart Drugs: Tyrosine kinase inhibitors in cancer therapy," *Cancer Cell*, 2002; 1:117-123.
Ullrich et al., "Signal transduction by receptors with tyrosine kinase activity" *Cell*, 1990; 61(2):203-212.
Verbeek et al., "Overexpression of c-Src enhances cell-matrix adhesion and cell migration in PDGF-stimulated NIH3T3 fibroblasts" *Exp. Cell Res.*, 1999; 248(2):531-537.
Wiener et al., "Decreased Src tyrosine kinase activity inhibits malignant human ovarian cancer tumor growth in a nude mouse model" *Clin. Cancer Res.*, 1999; 5(8):2164-2170.
Wilks, "Protein tyrosine kinase growth factor receptors and their ligands in development, differentiation, and cancer" *Adv. Cancer Res.*, 1993; 60:43-73.
Yarden et al., "Growth factor receptor tyrosine kinases" *Ann. Rev. Biochem.*, 1988; 57:443-478.
Yoneda et al., "Herbimycin A, a pp60c-src tyrosine kinase inhibitor, inhibits osteoclastic bone resorption in vitro and hypercalcemia in vivo" *J. Clin. Invest.*, 1993; 91(6):2791-2795.

In the U.S. Patent and Trademark Office U.S. Appl. No. 10/558,007 Non-Final Office Action dated Apr. 28, 2008, 5 pages.
In the U.S. Patent and Trademark Office U.S. Appl. No. 10/558,007 Non-Final Office Action dated Nov. 25, 2008, 5 pages.
In the U.S. Patent and Trademark Office U.S. Appl. No. 10/596,509 Non-Final Office Action dated Nov. 26, 2008, 6 pages.
In the U.S. Patent and Trademark Office U.S. Appl. No. 11/720,681 Non-Final Office Action dated Mar. 3, 2011, 6 pages.
In the U.S. Patent and Trademark Office U.S. Appl. No. 11/720,681 Non-Final Office Action dated Sep. 14, 2010, 7 pages.
In the U.S. Patent and Trademark Office U.S. Appl. No. 11/875,288 Final Office Action dated Sep. 24, 2009, 2009, 8 pages.
In the U.S. Patent and Trademark Office U.S. Appl. No. 11/875,288 Non-Final Office Action dated Apr. 15, 2009, 8 pages.
In the U.S. Patent and Trademark Office U.S. Appl. No. 11/993,237 Final Office Action dated Jul. 21, 2011, 5 pages.
In the U.S. Patent and Trademark Office U.S. Appl. No. 11/993,237 Non-Final Office Action dated Dec. 10, 2010, 7 pages.
In the U.S. Patent and Trademark Office U.S. Appl. No. 12/373,404 Final Office Action dated Jun. 28, 2011, 47 pages.
In the U.S. Patent and Trademark Office U.S. Appl. No. 12/373,404 Non-Final Office Action dated Oct. 27, 2010, 12 pages.
In the U.S. Patent and Trademark Office U.S. Appl. No. 12/624,637 Non-Final Office Action dated Feb. 2, 2012, 5 pages.
In the U.S. Patent and Trademark Office U.S. Appl. No. 12/670,670 Final Office Action dated Mar. 9, 2012, 5 pages.
In the U.S. Patent and Trademark Office U.S. Appl. No. 12/670,670 Non-Final Office Action dated Nov. 9, 201, 10 pages.
In the U.S. Patent and Trademark Office U.S. Appl. No. 11/720,693 Non-Final Office Action dated Jul. 21, 2010, 5 pages.
In the U.S. Patent and Trademark Office U.S. Appl. No. 11/720,693 Final Office Action dated Nov. 4, 2011, 6 pages.
Arora et al., "Role of Tyrosine Kinase Inhibitors in Cancer Therapy," *Perspectives in Pharmacology*, 2005; 315: 971-979.
Bagrov et al., "N-[Hydroxy(amino)alkyl]amides of Amino(nitro)benzoic Acids", *Russian Journal of Organic Chemistry*, 2000; 36: 674-678.
Barr et al. "Polo-Like Kinases and the Orchestration of Cell Division", *Molecular Cell Biology, Nature Reviews*, 2004; 5: 429-440.
Bettencourt-Dias, et al. "SAK/PLK4 is Required for Centriole Duplication and Flagella Development", *Current Biology*, 2005; 15:2199-2207.
Burke, "Protein-Tyrosine Kinase Inhibitors", *Drugs of the Future*, 1992; 17: 119-131.
Burns, et al. "Silencing of the Novel p53 Target Gene Sank/Plk2 Leads to Mitotic Catastrophe in Paclitaxel (Taxol)-Exposed Cells", *Molecular and Cellular Biology*, 2003; 23: 5556-5571.
Carvajal et al., "Aurora Kinases: New Targets for Cancer Therapy", *Clinical Cancer Research*, 2006; vol. 12, No. 23: (6869-6875).
Castedo et al., "Cell death by mitotic catastrophe: a molecular definition." *Oncogene*, 2004; 23: 2825-2837.
Coghlan et al., "Selective small molecule inhibitors of glycogen synthase kinase-3 modulate glycogen metabolism and gene transcription", *Chemistry & Biology*, 2000; 7: 793-803.
Collins et al., "The Chemotherapy of Schistosomiasis. Part IV. Some Ethers of 4-Amino-2- methoxyphenol", *Journal of the Chemical Society*, 1961: 1863-1879.
Cross et al., "Selective small-molecule inhibitors of glycogen synthase kinase-3 activity protect primary neurons from death", *Journal of Neurochemistry*, 2001; 77: 94-102.
Dai et al., "Tyrosine Kinase Etk/BMX is Up-Regulated in Human Prostate Cancer and Its Overexpression Induces Prostate Intraepithelial Neoplasia in Mouse", *Cancer Research*, 2006; 66: 8058-8064.
Delia et al., "Fused Pyrimidines Part Four: Miscellaneous Fused Pyrimidines", *The Chemistry of Heterocyclic Compounds, A Series of Monographs*, 1992: 261-305.
Elder et al., "Overexpression of Transforming Growth Factor a in Psoriatic Epidermis", *Science*, 1989; 243: 811-814.
Embi et al., "Glycogen Synthase Kinase-3 from Rabbit Skeletal Muscle Separation from Cyclic-AMP-Dependent Protein Kinase and Phosporylase Kinase", *Eur. J. Biochem.*, 1980; 107: 519-527.

Fode et al. "Sak, a Murine Protein-Serine/Threonine Kinase that is Related to the Drosophila Polo Kinase and Involved in Cell Proliferation", *Proc. Natl. Acad. Sci.*, 1994; 9: 6388-6392.
Furuta et al, "Molecular Design of Glutathione-Derived Biochemical Probes Targeting the GS-X Pump", *Tetrahedron*, 1999; 55: 7529-7540.
He et al., "Suppression of Tumor Lymphangiogenesis and Lymph Node Metastasis by Blocking Vascular Endothelial Growth Factor Receptor 3 Signaling", *Journal of the National Cancer Institute*, 2002; 94:819-825.
Hennequin et al., "Novel-4 Anilinoquinazolines with C-7 Basic Side Chains: Design and Structure Activity Relationship of a Series of Potent, Orally Active, VEGF Receptor Tyrosine Kinase Inhibitors", *Journal of Medicinal Chemistry*, 2002; 45: 1300-1312.
International Search Report from PCT/EP2004/005621, dated Oct. 27, 2004.
International Search Report from PCT/EP2004/053497, dated Apr. 12, 2005.
International Search Report from PCT/EP2004/053501, dated Apr. 28, 2005.
International Search Report from PCT/EP2005/056606, dated Apr. 3, 2006.
International Search Report from PCT/EP2005/056609, dated May 26, 2005.
International Search Report from PCT/EP2007/061499, dated Jul. 30, 2008.
International Search Report from PCT/EP2008/059833, dated Oct. 23, 2008.
International Search Report from PCT/EP2009/052692, dated Jun. 9, 2009.
International Search Report from PCT/EP2006/063555, dated Feb. 21, 2008.
Kaipainen et al. "Expression of the fms-Like Tyrosine Kinase 4 Gene Becomes Restricted to Lymphatic Endothelium During Development", *Pro. Natl. Acad. Sci.*, 1995; 92: 3566-70.
Karkkainen et al. "Lymphatic Endothelial Regulation, Lymphoedema, and Lymph Node Metastasis", *Cell & Developmental Biology*, 2002; 13: 9-18.
Kawato et al., "Novel Pepitdomimetics of the Antifungal Cyclic Peptide Rhodopeptin: Synthesis of Mimetics and Their Antifungal Activity", *Organic Letters*, 2001; 3: 3451-3454.
Kuo et al., Synthesis and Identification of [1,3,5]Triazine-pyridine Biheteroaryl as a Novel Series of Potent Cyclin-Dependent Kinase Inhibitors, *J. Med. Chem.*, 2005; 48: 4535-4546.
Li, et al., "Sak, a New Polo-Like Kinase, is Transcriptionally Repressed by p53 and Induces Apoptosis upon RNAi Silencing", *Neoplasia*, 2005; 7: 312-323.
Morin, "Oncogene to Drug: Development of Small Molecule Tyrosine Kinase Inhibitors as Anti-Tumor and Anti-Angiogenic Agents", *Oncogene*, 2000; 19: 6574-6583.
Murphy et al., "Intramolecular Termination of Radical-Polar Crossover Reactions", *Journal of the Chemical Society Perkin Transactions 1*, 1998; 15: 2331-2339.
Nagamatsu et al., "General Syntheses of 1-Alkyltoxoflavin and 8-Alkylfervenulin Derivatives of Biological Significance by the Regioselective Alkylation of Reumycin Derivatives and the Rates of Transalkylation From 1-Alkyltoxoflavins Into Nucleophiles", *J. Chem. Soc., Perkin Trans.* 1, 2001: 130-137.
Nagamatsu et al., "Syntheses of 3-Substituted 1-Methyl-6-Phenylprimido[5,4-e]-1,2,4- Triazine-5,7(1H,6H)-Diones (6-Phenyl Analogs of Toxoflavin) and Their 4-Oxides, and Evaluation of Antimicrobial Activity of Toxoflavins and Their Analogs", *Chem. Pharm. Bull*, 1993; 41: 362-368.
Palmer et al., "Tyrosine Kinase Inhitors. Ii. Soluble Analogues of Pyrrolo- and Pyrazoloquinazolines as Epidermal Growth Factor Receptor Inhibitors: Synthesis, Biological Evaluation, and Modeling of the Mode of Binding", *Journal of Medicinal Chemistry*, 1997; 40: 1519-1529.
Rusnak et al., "The characterization of novel, dual ErbB-2/Egfr, tyrosine kinase inhibitors: potential therapy for cancer", *Cancer Research*, 2001; 61: 7196-7203.
Saito et al., "Fyn: a Novel Molecular Target in Prostate Cancer", *Cancer*, 2010; 116:1629- 1637.

Spankuch-Schmitt et al., "Downregulaton of Human Polo-Like Kinase Activity by Antisense Oligonucleotides Induces Growth Inhibitor in Cancer Cells", *Oncogene*, 2002: 31623171.

Stacker et al., "The Role of Tumor Lymphangiogenesis in Metastatic Spread", *FASEB J.*, 2002; 16: 922-34.

Table of Contents, Chemical Reviews, 1996; vol. 96, No. 8.

Von Pawel, "Gefitinib (Iressa, ZD1839): a novel targeted approach for the treatment of solid tumors," *Bull. Cancer*, 2004; 91(5): E70-E76.

Wang et al., "Cell Cycle Arrest and Apoptosis Induced by Human Polo-Like Kinase 3 Is Mediated through Perturbation of Microtubule Integrity", *Molecular and Cellular Biology*, 2002: 22:3450-3459.

Wedge et al. "ZD6474 Inhibits Vascular Endothelial Growth Factor Signaling, Angiogenesis, and Tumor Growth Following Oral Administration", *Cancer Research*, 2002; vol. 62: (4645).

Yuan et al. "Efficient Internalization of the Polo-Box of Polo-Like Kinase 1 Fused to an Antennapedia Peptide Results in Inhibition of Cancer Cell Proliferation":, *Cancer Research*, 2002; 62: 4186-4190.

Zeneca Ltd., "4-Anilinoquinazoline Derivatives", *Expert Opinion on Therapeutic Patents*, 1998; 8: 475-478.

Brown et al., "FlasPLate Technology—Principles and Characteristics of Flashplate Scintillation Counting", *High Throughput Screening, The Discovery of Bioactive Substances*, 1997; 317-328.

Calderwood et al., "Pyrrolo[2,3-d]pyrimidines Containing Diverse N-7 Substituents as Potent Inhibitors of Lck", *Biorganic & Medicinal Chemistry Letters*, 2002; 12: 1683-1686.

Cardiello et al., "Epidermal Growth Factor Receptor Tyrosine Kinase Inhibitors in Late Stage Clinical Trials", *Oncologic, Endocrine & Metabolic, Expert Opinion*, 2003; 8(2): 501-514.

Cohen et al., "The renaissance of GSK3", *Nature Reviews: Molecular Cell Biology*, 2001; 2: 769-776.

Cook et al., "Scintillation Proximity Enzyme Assay. A Rapid and Novel Assay Technique Applied to HIV Proteinase", *Structure and Function of the Aspartic Proteinases*, 1991: 525-528.

Dumont et al. "Cardiovascular Failure in Mouse Embryos Deficient in VEGF Receptor-3", *Science*, 1998; 282:946-949.

Grimminger et al., "Targeting non-malignant disorders with tyrosine kinase inhibitors", *Nature Review: Drug Discovery*, 2010; 9: 856-870.

Kaidanovich et al. "The role of glycogen synthase kinase-3 in insulin resistance and Type 2 diabetes", *Expert Opinion on Therapeutic Targets*, 2002; 6: 555-561.

Karn et al. "Human SAK Related to the PLK/polo Family of Cell Cycle Kinases Shows High mRNA Expression in testis", *Oncology Reports*, 1997; 5: 505-10 (Abstract Only).

Kypta, "Gsk-3 inhibitors and their potential in the treatment of Alzheimer's disease", *Expert Opinion on Therapeutic Patents*, 2005; 15: 1315-1331.

Liotta et al. "Tumor Invasion and Metastases: Biochemical Mechanisms", *Cancer Treatment and Research*, 1988; 40: 223-238.

Makinen et al., "Inhibition of Lymphangiogenesis with Resulting Lymphedema in Transgenic Mice Expressing Soluble VEGF Receptor-3", *Nature Medicine*, 2001; 7: 199-205.

Nicolson et al., "Cancer Metastasis: Tumor Cell and Host Organ Properties Important in Metastasis to Specific Secondary Sites", *Biochimica et Biophysica Acta*, 1988; 948: 175-224.

Norman, "Emerging Fundamental Themes in Modern Medicinal Chemistry", *Drug News Perspect*, 2001; 14: 242-247.

Ny et al., "A Genetic Xenopus Laevis Tadpole Model to Study Lymphangiogenesis", *Nature Medicine*, 2005; 11: 998-1004.

Pleixats et al., "The Search for New Biochemical Photoprobes. The Nucleophilic Photosubstitution of 2-Fluoro-4-Nitronisole", *Tetrahedron*, 45: 7817-7826. (1989).

Prichard et al., "The prevention of breast cancer," *British Journal of Surgery*, 2003; 90: 772-783.

Skobe et al. "Induction of Tumor Lymphangiogenesis by Vegf-C Promotes Breast Cancer Metastasis", *Nature Medicine*, 2001; 7: 192-198.

Underiner et al., "Development of Vascular Endothelial Growth Factor Receptor (VEGFT) Kinase Inhibitors as Anti-Angiogenic Agents in Cancer Therapy", *Current Medicinal Chemistry*, 2004; 11: 731-745.

Wissner et al., "4-Anilino-6,7-dialkoxyquinoline-3-carbonitrile Inhibitors of Epidermal Growth Factor Receptor Kinase and Their Bioisosteric Relationship To The 4-Anilino-6,7-dialkoxyquinazoline Inhibitors", *Journal of Medicinal Chemistry*, 2000; 43: 3244-3256.

Wright et al., "Anilinoquinazoline Inhibitors of Fructose 1,6-Bisphosphate Bind at a Nove Allosteric Site: Synthesis, in vitro Characterizations, and X-ray Crystallography", *J. Med. Chem.*, 2002; 45:3865-3877.

Yang et al., "Inhibition of Epidermal Growth Factore Receptor Tyrosine Kinase by Chalcone Derivatives," *Biochimica of Biophysica Acta*, 2001; 1550: 144-152.

Zetter et al., "The Cellular Basis of Site-Specific Tumor Metastasis", *N. Engl. J. Med.*, 1990; 322: 605-12.

* cited by examiner ns
MTKI QUINAZOLINE DERIVATIVES

CROSS REFERENCE TO RELATED APPLICATIONS

This application is a national stage application of Patent Application No. PCT/EP2007/057200, filed Jul. 12, 2007, which application claims priority from EPO Patent application Ser. No. 06117185.6, filed Jul. 13, 2006, both of which are hereby incorporated by reference in their entirety.

The invention concerns certain novel quinazoline derivatives, or pharmaceutically acceptable salts thereof, which possess anti-tumour activity and are accordingly useful in methods of treatment of the human or animal body. The invention also concerns processes for the manufacture of said quinazoline derivatives, pharmaceutical compositions containing them and their use in therapeutic methods, for example in the manufacture of medicaments for use in prevention or treatment of cell proliferative diseases such as atherosclerosis, restinosis and cancer in the human or animal body.

In recent years, it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Several such oncogenes give rise to the production of peptides which are receptors for growth factors. Activation of the growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988 57, 443; Larsen et al., *Ann. Reports in Med. Chem.*, 1989, Chpt. 13). The first group of tyrosine kinases to be identified arose from such viral oncogenes, for example pp60v-Src tyrosine kinase (otherwise known as v-Src), and the corresponding tyrosine kinases in normal cells, for example pp60c-Src tyrosine kinase (otherwise known as c-Src).

Receptor tyrosine kinases play an important role in the transmission of biochemical signals which initiate cell replication. These are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43-73) based on families of growth factors which bind to different receptor tyrosine kinases. The classification includes Class I receptor tyrosine kinases comprising the EGF family of receptor tyrosine kinases such as the EGFR (or Her1 or erbB1), HER2 (or ErbB2), HER3 (or ErbB3) and HER4 (or ErbB4). Within these Class I receptors, HER3 does not have tyrosine kinase activity but retains ligand-binding function and is competent for signal transduction. The classification further includes Class II receptor tyrosine kinases comprising the insulin family of receptor tyrosine kinases such as the insulin and IGFI receptors and insulin-related receptor (IRR) and Class III receptor tyrosine kinases comprising the platelet-derived growth factor (PDGF) family of receptor tyrosine kinases such as the PDGFα, PDGFβ; and colony-stimulating factor 1 (CSF1) receptors.

It is also known that certain tyrosine kinases belong to the class of non-receptor tyrosine kinases which are located intracellularly and are involved in the transmission of biochemical signals such as those that influence tumour cell motility, dissemination and invasiveness and subsequently metastatic tumour growth (Ulkich et al., *Cell*, 1990, 61, 203-212, Bolen et al., *FASEB J.*, 1992, 6, 3403-3409, Brickell et al., *Critical Reviews in Oncogenesis*, 1992, 3, 401-406, Bohlen et al., *Oncogene*, 1993, 8 2025-2031, Courtneidge et al., *Semin. Cancer Biol.*, 1994, 5, 239-246, Lauffenburger et al., *Cell*, 1996, 84, 359-369, Hanks et al., *BioEssays*, 1996, 19, 137-145, Parsons et al., *Current Opinion in Cell Biology*, 1997, 9, 187-192, Brown et al., *Biochimica et Biophysica Acta*, 1996, 1287, 121-149 and Schlaepfer et al., *Progress in Biophysics and Molecular Biology*, 1999, 71, 435-478). Various classes of non-receptor tyrosine kinases are known including the Src-family such as the Src, Lyn, Fyn and Yes tyrosine kinases, the Abl family such as Abl and Arg and the Jak family such as Jak 1 and Tyk 2.

It is known that the Src family of non-receptor tyrosine kinases are highly regulated in normal cells and in the absence of extracellular stimuli are maintained in an inactive-conformation. However, some Src family members, for example c-Src tyrosine kinase, is frequently significantly activated (when compared to normal cell levels) in common human cancers such as gastrointestinal cancer, colon, rectal, stomach cancer (Cartwright et al., *Proc. Natl. Acad. Sci; USA*, 1990, 87, 558-562 and Mao et al., Oncogene, 1997, 15, 3083-3090), and breast cancer (Muthuswamy et al., *Oncognen*, 1995, 11, 1801-1810). The Src family of non-receptor tyrosine kinases has also been identified in other common human cancers such as non-small cell lung cancers (NSCLCS) including adenocarcinomas and squamous cell cancer of the lung (Mazurenko et al., *European Journal of Cancer*, 1992, 28, 372-7), bladder cancer (Fanning et al., *Cancer Research*, 1992, 52, 1457-62), oesophageal cancer (Jankowski et al., *Gut*, 1992, 33, 1033-8), cancer of the prostate, ovarian cancer (Wiener et al., *Clin. Cancer Research*, 1999, A, 2164-70) and pancreatic cancer (Lutz et al., *Biochem. and Biophys. Res. Comm.*, 1998, 243, 503-8). As more human tumour tissues are tested for the Src family of non-receptor tyrosine kinases, it is expected that its widespread prevalence will be established.

It is further known that the predominant role of c-Src non-receptor tyrosine kinase is to regulate the assembly of focal adhesion complexes through interaction with a number of cytoplasmic proteins including, for example, focal adhesion kinase and paxillin. In addition, c-Src is coupled to signalling pathways that regulate the actin cytoskeleton which facilitates cell motility. Likewise, important roles are played by the c-Src, c-Yes and c-Fyn non-receptor tyrosine kinases in integrin mediated signalling and in disrupting cadherin-dependent cell-cell junctions (Owens et al., *Molecular Biology of the Cell*, 2000, LI, 51-64 and Klinghoffer et al., *EMBO Journal*, 1999, 18, 2459-2471). Cellular motility is necessarily required for a localised tumour to progress through the stages of dissemination into the blood stream, invasion of other tissues and initiation of metastatic tumour growth. For example, colon tumour progression from localised to disseminate, invasive metastatic disease has been correlated with c-Src non-receptor tyrosine kinase activity (Brunton et al., *Oncogene*, 1997, 14, 283-293, Fincham et al., *EMBO J*, 1998, 17, 81-92 and Verbeek et al., *Exp. Cell Research*, 1999, 248, 531-537).

Accordingly, it has been recognised that an inhibitor of such non-receptor tyrosine kinases should be of value as a selective inhibitor of the motility of tumour cells and as a selective inhibitor of the dissemination and invasiveness of mammalian cancer cells leading to inhibition of metastatic tumour growth. In particular, an inhibitor of such non-receptor tyrosine kinases should be of value as an anti-invasive agent for use in the containment and/or treatment of solid tumour disease. Support for this view is provided by the development of Herceptin® (Trastuzumab) and Gleevec™ (imatinib mesylate), the first examples of target-based cancer drugs. Herceptin® (Trastuzumab) is targeted against Her2/neu, a receptor tyrosine kinase found to be amplified up to 100-fold in about 30% of patients with invasive breast cancer. In clinical trials, Herceptin® (Trastuzumab) proved to have anti-tumour activity against breast cancer (Review by L. K. Shawer et al, "Smart Drugs: Tyrosine kinase inhibitors in cancer therapy", 2002, Cancer Cell Vol. 1, 117), and accordingly provided the proof of principle for therapy targeting the receptor tyrosine kinases. The second example, Gleevec™ (imatinib mesylate), developed against the abelson tyrosine kinase (Bcr-Abl), a constitutively active cytoplasmic tyrosine kinase present in virtually all patients with chronic myelogenous leukaemia (CML) and 15% to 30% of adult patients with acute lymphoblastic leukaemia. In clinical trials, Gleevec™ (imatinib mesylate) showed a spectacular efficacy with minimal side effects that led to an approval within 3 months of submission. The speed of passage of this agent through clinical trials and regulatory review has become a case study in rapid drug development (Drucker B. J. & Lydon N., "Lessons learned from the development of an Abl tyrosine kinase inhibitor for chronic myelogenous leukaemia.", 2000, J. Clin. Invest., 105, 3).

We have now found that surprisingly, certain quinazoline derivatives possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of the receptor and non-receptor tyrosine-specific protein kinases that are involved in the signal transduction steps which lead to the invasiveness and migratory ability of metastatic tumour cells. In particular, it is believed that the compounds of the present invention provide an anti-tumour effect by way of inhibition of the Src family of non-receptor tyrosine kinases, for example by inhibition of one or more of c-Src, c-Yes and c-Fyn.

It is also known that c-Src non-receptor tyrosine kinase enzyme is involved in the control of osteoclast-driven bone resorption (Soriano et al., *Cell* 1991, 64, 693-702; Boyce et al., *J. Clin. Invest.*, 1992, 90, 1622-1627; Yoneda et al., *J. Clin. Invest.*, 1993, 91, 2791-2795 and Missbach et al., *Bone,* 1999, 24, 43749). An inhibitor of c-Src non-receptor tyrosine kinase is therefore of value in the prevention and treatment of bone diseases such as osteoporosis, Paget's disease, metastatic disease in bone and tumour-induced hypercalcaemia.

Fyn kinase mediated phosphorylation of the NMDA receptor NR2B subunit has been shown to be essential for the maintenance of neuropathic pain (Abe et al, *Eur J Neurosci*, 2005, 22, 1445-1454). An inhibitor of Fyn kinase is therefore of value in the treatment of neuropathic pain.

The compounds of the present invention, are also useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, hypersensitivity reactions of the skin, blood vessel diseases (for example atherosclerosis and restenosis), allergic asthma, insulin-dependent diabetes, diabetic retinopathy and diabetic nephropathy.

Generally, the compounds of the present invention possess potent inhibitory activity against the Src family of non-receptor tyrosine kinases, for example by inhibition of c-Src and/or c-Yes, whilst possessing less potent inhibitory activity against other tyrosine kinase enzymes such as the receptor tyrosine kinases, for example EGF receptor tyrosine kinase and/or VEGF receptor tyrosine kinase. Furthermore, certain compounds of the present invention possess substantially better potency against the Src family of non-receptor tyrosine kinases, for example c-Src and/or c-Yes, than against VEGF receptor tyrosine kinase. Such compounds possess sufficient potency against the Src family of non-receptor tyrosine kinases, for example c-Src and/or c-Yes, that they may be used in an amount sufficient to inhibit, for example, c-Src and/or c-Yes whilst demonstrating little activity against VEGF receptor tyrosine kinase.

It is disclosed in US 2005/0009867 that certain 4-(2,3-methylenedioxyanilino)-3-cyanoquinoline derivatives are useful for the inhibition of Src-dependent cell proliferation. There is no disclosure therein of any macrocyclized 4-(2,3-methylenedioxyanilino)-3-quinazoline derivatives.

It is disclosed in US 2005/0250797 that certain 7-alkynyl-1,3-benzodioxol-4-yl containing quinazolines or 7-alkenyl-1,3-benzodioxol-4-yl containing quinazolines are useful in treating hyperproliferative diseases such as cancer. There is no disclosure therein of any macrocyclized 4-(2,3-methylenedioxyanilino)-3-quinazoline derivatives.

It is accordingly an object of the present invention, to provide further tyrosine kinase inhibitors useful in the manufacture of medicaments in the treatment of cell proliferative related disorders.

It is further an object of the present invention to provide Fyn kinase inhibitors useful in the manufacture of medicaments in the treatment of neuropathic pain.

This invention concerns compounds of formula (I)

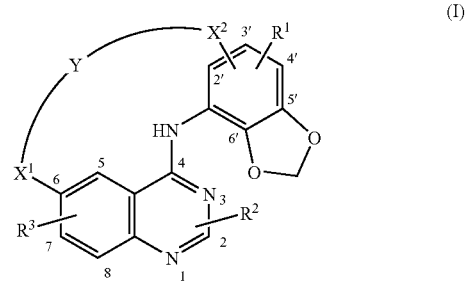

the N-oxide forms, the pharmaceutically acceptable addition salts and the stereochemically isomeric forms thereof, wherein Y represents —$C_{3-9}$alkyl-, —$C_{1-5}$alkyl-O—$C_{1-5}$alkyl-, —$C_{1-5}$ alkyl-$NR^6$—$C_{1-5}$alkyl-, —$C_{1-5}$alkyl-$NR^7$—CO—$C_{1-5}$alkyl-, —$C_{1-6}$alkyl-$NR^7$—CO—, —$NR^7$—CO—$C_{1-6}$alkyl-, —$C_{1-3}$alkyl-$NR^7$—CO-$Het^1$-, —$C_{1-6}$alkyl-$NR^8$-$Het^2$-, $C_{1-6}$alkyl-CO—$C_{1-6}$alkyl-, —$C_{1-6}$alkyl-CO—$NR^7$— or —CO—$NR^7$—$C_{1-6}$alkyl-;
  in particular Y represents —$C_{3-9}$alkyl-, —$C_{1-5}$alkyl-O—$C_{1-5}$alkyl-, —$C_{1-5}$alkyl-$NR^6$—$C_{1-5}$alkyl-, —$C_{1-5}$alkyl-$NR^7$—CO—$C_{1-5}$alkyl-, —$C_{1-6}$alkyl-NH—CO—, —NH—CO—$C_{1-6}$alkyl-, —$C_{1-3}$alkyl-NH—CO-$Het^1$-, —$C_{1-6}$alkyl-$NR^8$-$Het^2$-, $C_{1-6}$alkyl-CO—$C_{1-6}$alkyl-, —$C_{1-6}$alkyl-CO—NH— or —CO—NH—$C_{1-6}$alkyl-;

$X^1$ represents —O—, —O—$C_{1-2}$alkyl- or —$NR^4$—$C_{1-2}$alkyl-;

$X^2$ represents a direct bond, —$C_{1-2}$alkyl-, —O—, —O—$C_{1-2}$alkyl- or —$NR^5$—$C_{1-2}$alkyl-;

$R^1$ represents hydrogen, cyano, halo, hydroxy, $C_{1-4}$alkyl, $Het^3$, $Ar^1$, $Het^3$-O— or $Ar^1$—O—;

$R^2$ represents hydrogen, cyano, halo, $C_{2-6}$alkenyl, $C_{2-6}$alkynyl, $C_{3-7}$cycloalkyl or $C_{1-6}$alkyl wherein said $C_{2-6}$alkenyl, $C_{2-6}$alkynyl, $C_{3-7}$cycloalkyl or $C_{1-6}$alkyl are optionally substituted with one or where possible two or more substituents selected from hydroxy or halo; in particular $R^2$ represents hydrogen, cyano, halo or $C_{1-6}$alkyl optionally substituted with one or where possible two or more substituents selected from hydroxy or halo;

$R^3$ represents hydroxy; $C_{1-4}$alkyloxy; or $C_{1-4}$alkyloxy-substituted with one or where possible two or more substituents each independently selected from $Het^4$, hydroxy, $C_{1-4}$alkyloxy-, halo, $NR^9R^{10}$, $C_{1-4}$alkyl-O—C(=O)—O—, $Ar^2$, $NR^{11}R^{12}$-carbonyl, $Het^5$-carbonyl and oxiranyl;

$R^4$ represents hydrogen, $Ar^3$—S(=O)$_2$—, $Ar^3$—S(=O)—, $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- wherein said $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- is optionally substituted with $C_{1-4}$alkyloxy-, $Het^6$ or phenyl; in particular $R^4$ represents hydrogen, $C_{1-4}$alkyl or $C_{1-4}$alkyloxycarbonyl- wherein said $C_{1-4}$alkyloxycarbonyl- is optionally substituted with phenyl;

$R^5$ represents hydrogen, $Ar^3$—S(=O)$_2$—, $Ar^3$—S(=O)—, $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- wherein said $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- is optionally substituted with $C_{1-4}$alkyloxy-, $Het^6$ or phenyl; in particular $R^5$ represents hydrogen, $C_{1-4}$alkyl, $C_{1-4}$alkyloxycarbonyl-, $Ar^3$—S(=O)$_2$— or $Het^6$-$C_{1-4}$alkylcarbonyl wherein said $C_{1-4}$alkyloxycarbonyl- is optionally substituted with phenyl;

$R^6$ represents hydrogen, $Ar^4$—S(=O)$_2$—, $Ar^4$—S(=O)—, $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- wherein said $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- is optionally substituted with $C_{1-4}$alkyloxy-, $Het^7$ or phenyl; in particular $R^6$ represents hydrogen, $C_{1-4}$alkyl, $C_{1-4}$alkyloxycarbonyl-, $Ar^4$—S(=O)$_2$— or $Het^7$-$C_{1-4}$alkylcarbonyl wherein said $C_{1-4}$alkyloxycarbonyl- is optionally substituted with phenyl;

$R^7$ represents hydrogen, $Ar^4$—S(=O)$_2$—, $Ar^4$—S(=O)—, $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- wherein said $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- is optionally substituted with $C_{1-4}$alkyloxy-, $Het^8$ or phenyl; in particular $R^7$ represents hydrogen, $C_{1-4}$alkyl, $Het^8$-$C_{1-4}$alkyl or $C_{1-4}$alkyloxy$C_{1-4}$alkyl;

$R^8$ represents hydrogen, $Ar^5$—S(=O)$_2$—, $Ar^5$—S(=O)—, $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- wherein said $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- is optionally substituted with $C_{1-4}$alkyloxy-, $Het^8$ or phenyl; in particular $R^8$ represents hydrogen, $C_{1-4}$alkyl, $Ar^5$—S(=O)$_2$—, $Ar^5$—S(=O)—, $C_{1-4}$alkyloxycarbonyl or $Het^8$-$C_{1-4}$alkyloxycarbonyl;

$R^9$ and $R^{10}$ each independently represent hydrogen; $Het^9$; $Het^{11}$—S(=O)$_2$; $Het^{11}$—S(=O)—; $C_{1-4}$alkyl or $C_{1-4}$alkyl substituted with one or where possible two or more substituents selected from hydroxy, $C_{1-4}$alkyloxy, $C_{1-4}$alkyl-S(=O)$_2$, halo, $Het^{10}$, $C_{1-4}$alkyl-C(=O)—NR$^{13}$—, $C_{1-4}$alkyl-S(=O)$_2$—NR$^{14}$—, $C_{1-4}$alkyl-S(=O)—NR$^{14}$—, amino-C(=O)—NR$^{15}$, mono- or di($C_{1-4}$alkyl)amino-C(=O)—NR$^{16}$—, aminocarbonyl, aminocarbonyloxy, mono- or di($C_{1-4}$alkyl)aminocarbonyl, mono- or di($C_{1-4}$alkyl)aminocarbonyloxy, $Het^{12}$-oxycarbonyl, $C_{1-4}$alkyloxy-$C_{1-4}$alkyloxy-, $Het^{13}$-carbonyl; $C_{1-4}$alkyl-S(=O)—$C_{1-4}$alkyl-NR$^{17}$—C(=O)—; or $C_{1-4}$alkyl-S(=O)$_2$—$C_{1-4}$alkyl-NR$^{17}$—C(=O)—;

$R^{11}$ and $R^{12}$ each independently represent hydrogen; $C_{1-4}$alkyl or $C_{1-4}$alkyl substituted with one or where possible two or more substituents selected from hydroxy, $C_{1-4}$alkyloxy, $C_{1-4}$alkyl-S(=O)— or $C_{1-4}$alkyl-S(=O)$_2$—;

$R^{13}$ represents hydrogen or $C_{1-4}$alkyl;
$R^{14}$ represents hydrogen or $C_{1-4}$alkyl;
$R^{15}$, $R^{16}$ and $R^{17}$ each independently represent hydrogen or $C_{1-4}$alkyl;

$R^{18}$ and $R^{19}$ each independently represent hydrogen; $C_{1-4}$alkyl or $C_{1-4}$alkyl substituted with one or where possible two or more substituents selected from hydroxy, $C_{1-4}$alkyloxy, $C_{1-4}$alkyl-S(=O)— or $C_{1-4}$alkyl-S(=O)$_2$—;

$Het^1$ represents pyrrolidinyl, 2-pyrrolidinonyl or piperidinyl wherein said $Het^1$ is optionally substituted with one or where possible two or more substituents selected from hydroxy, $C_{1-4}$alkyl, $C_{1-4}$alkyloxy or $C_{1-4}$alkyloxycarbonyl;

$Het^2$ represents pyrrolidinyl, 2-pyrrolidinonyl or piperidinyl wherein said $Het^2$ is optionally substituted with one or where possible two or more substituents selected from hydroxy, $C_{1-4}$alkyl, $C_{1-4}$alkyloxy or $C_{1-4}$alkyloxycarbonyl;

$Het^3$ represents morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said $Het^3$ is optionally substituted with one or where possible two or more substituents selected from hydroxy, $C_{1-4}$alkyl, $C_{1-4}$alkyloxy- or $C_{1-4}$alkylsulfonyl;

$Het^4$ represents morpholinyl, piperidinyl, pyrrolidinyl, 1,1-dioxothiomorpholinyl, piperazinyl, furanyl, thiomorpholinyl, imidazolyl or pyrazolidinyl wherein said $Het^4$ is optionally substituted with one or where possible two or more substituents selected from hydroxy; $C_{1-4}$alkyl; amino; mono- or di($C_{1-4}$alkyl)amino; $C_{1-4}$alkyl-S(=O)$_2$—; $C_{1-4}$alkyl-S(=O)—; $C_{1-4}$alkyl substituted with one or where possible two or more substituents selected from hydroxy, $C_{1-4}$alkyl-C(=O)—NH—, $C_{1-4}$alkyl-S(=O)$_2$—, $C_{1-4}$alkyl-S(=O)—, amino, mono- or di($C_{1-4}$alkyl)aminocarbonyl, NR$^{18}$R$^{19}$, aminocarbonyl, $C_{1-4}$alkyloxy and mono- or di($C_{1-4}$alkyl)aminocarbonyl; $C_{1-4}$alkyl-C(=O)— optionally substituted with one or where possible two or more substituents selected from hydroxy, $C_{1-4}$alkyloxy, $C_{1-4}$alkylsulfoxy and $C_{1-4}$alkylsulfonyl; or with $C_{1-4}$alkyloxycarbonyl optionally substituted with one or where possible two or more substituents selected from hydroxy, $C_{1-4}$alkyloxy, $C_{1-4}$alkylsulfoxy and $C_{1-4}$alkylsulfonyl;

$Het^5$ represents morpholinyl, piperidinyl, pyrrolidinyl, 1,1-dioxothiomorpholinyl, piperazinyl or thiomorpholinyl wherein said $Het^5$ is optionally substituted with one or where possible two or more substituents selected from $C_{1-4}$alkyl; hydroxy; amino; mono- or di($C_{1-4}$alkyl)amino; $C_{1-4}$alkyl-S(=O)$_2$; $C_{1-4}$alkyl-S(=O) and $C_{1-4}$alkyl substituted with one or where possible two or more substituents selected from hydroxy, $C_{1-4}$alkyl-C(=O)—NH—, $C_{1-4}$alkyl-S(=O)$_2$— and $C_{1-4}$alkyl-S(=O));

$Het^6$, $Het^7$ and $Het^8$ each independently represent morpholinyl, piperazinyl, piperidinyl or pyrrolidinyl wherein said $Het^6$, $Het^7$ and $Het^8$ are optionally substituted with one or more substituents selected from hydroxy, amino, $C_{1-4}$alkyl and $C_{1-4}$alkyl substituted with one or where possible two or more substituents selected from hydroxy, halo, and $C_{1-4}$alkyloxy-;

$Het^9$ and $Het^{10}$ each independently represent morpholinyl, piperidinyl, pyrrolidinyl, 1,1-dioxothiomorpholinyl, piperazinyl or thiomorpholinyl wherein said $Het^9$ and $Het^{10}$ are optionally substituted with one or where possible two or more substituents selected from $C_{1-4}$alkyl; hydroxy; amino; mono- or di($C_{1-4}$alkyl)amino; $C_{1-4}$alkyl-S(=O)$_2$; and $C_{1-4}$alkyl substituted with one or where possible two or more substituents selected from hydroxy, $C_{1-4}$alkyl-C(=O)—NH—, $C_{1-4}$alkyl-S(=O)$_2$— and $C_{1-4}$alkyl-S(=O);

$Het^{11}$, $Het^{12}$ and $Het^{13}$ each independently represent morpholinyl, piperazinyl, piperidinyl or pyrrolidinyl wherein said $Het^{11}$, $Het^{12}$ and $Het^{13}$ are optionally substituted with one or more substituents selected from hydroxy, amino, $C_{1-4}$alkyl and $C_{1-4}$alkyl substituted with one or where possible two or more substituents selected from hydroxy, halo, and $C_{1-4}$alkyloxy-;

$Ar^1$ and $Ar^2$ each independently represent phenyl optionally substituted with nitro, cyano, hydroxy, $C_{1-4}$alkyl, $C_{1-4}$alkyloxy- or amino;

$Ar^3$, $Ar^4$ and $Ar^5$ each independently represent phenyl optionally substituted with nitro, cyano, hydroxy, $C_{1-4}$alkyl, $C_{1-4}$alkyloxy- or amino.

As used in the foregoing definitions and hereinafter, $C_{1-2}$alkyl defines methyl or ethyl;

$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like;

$C_{1-5}$alkyl defines straight and branched chain saturated hydrocarbon radicals having from 1 to 5 carbon atoms such as, for example, methyl, ethyl, propyl, butyl, pentyl, 1-methylbutyl, 2,2-dimethylpropyl, 2,2-dimethylethyl and the like;

$C_{1-6}$alkyl is meant to include $C_{1-5}$alkyl and the higher homologues thereof having 6 carbon atoms such as, for example hexyl, 1,2-dimethylbutyl, 2-methylpentyl and the like;

$C_{1-7}$alkyl is meant to include $C_{1-6}$alkyl and the higher homologues thereof having 7 carbon atoms such as, for example 1,2,3-dimethylbutyl, 1,2-methylpentyl and the like;

$C_{3-9}$alkyl defines straight and branched chain saturated hydrocarbon radicals having from 3 to 9 carbon atoms such as propyl, butyl, pentyl, hexyl, heptyl, octyl, nonyl and the like;

$C_{1-4}$alkyloxy defines straight or branched saturated hydrocarbon radicals such as methoxy, ethoxy, propyloxy, butyloxy, 1-methylethyloxy, 2-methylpropyloxy and the like;

$C_{1-6}$alkyloxy is meant to include $C_{1-4}$alkyloxy and the higher homologues such as methoxy, ethoxy, propyloxy, butyloxy, 1-methylethyloxy, 2-methylpropyloxy and the like;

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalo$C_{1-6}$alkyl as a group or part of a group is defined as mono- or polyhalosubstituted $C_{1-6}$alkyl, for example methyl with one or more fluoro atoms, for example, difluoromethyl or trifluoromethyl, 1,1-difluoro-ethyl and the like. In case more than one halogen atoms are attached to an alkyl group, within the definition of polyhalo$C_{1-4}$alkyl or polyhalo$C_{1-6}$alkyl, they may be the same or different.

The heterocycles as mentioned in the above definitions and hereinafter, are meant to include all possible isomeric forms thereof, for instance pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl. Further, the heterocycles as mentioned in the above definitions and hereinafter may be attached to the remainder of the molecule of formula (I) through any ring carbon or heteroatom as appropriate. Thus, for example, when the heterocycle is imidazolyl, it may be a 1-imidazolyl, 2-imidazolyl, 3-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzothiazolyl, it may be 2-benzothiazolyl, 4-benzothiazolyl, 5-benzothiazolyl, 6-benzothiazolyl and 7-benzothiazolyl.

The pharmaceutically acceptable addition salts as mentioned hereinabove, are meant to comprise the therapeutically active non-toxic acid addition salt forms which the compounds of formula (I) are able to form. The latter, can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove, are meant to comprise the therapeutically active non-toxic base addition salt forms which the compounds of formula (I) are able to form. Examples of such base addition salt forms are, for example, the sodium, potassium, calcium salts, and also the salts with pharmaceutically acceptable amines such as, for example, ammonia, alkylamines, benzathine, tromethamine, N-methyl-D-glucamine, hydrabamine, amino acids, e.g. arginine, lysine.

Conversely said, salt forms can be converted by treatment with an appropriate base or acid into the free acid or base form.

The term addition salt as used hereinabove also, comprises the solvates which the compounds of formula (I) as well as the salts thereof, are able to form. Such solvates are for example hydrates, alcoholates and the like.

The term stereochemically isomeric forms as used hereinbefore, defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I), both in pure form or in admixture with each other, are intended to be embraced within the scope of the present invention.

Some of the compounds of formula (I) may also exist in their tautomeric forms. Such forms although not explicitly indicated in the above formula are intended to be included within the scope of the present invention.

The N-oxide forms of the compounds of formula (I) are meant to comprise those compounds of formula (I) wherein one or several nitrogen atoms are oxidized to the so-called N-oxide.

The chemical names of the macrocyclic compounds of the present invention were generated according to the nomenclature rules agreed upon by the Chemical Abstracts Service (CAS). In case of tautomeric forms, the name of the depicted tautomeric form of the structure was generated. However it should be clear for the present invention that the other, non-depicted tautomeric form is also included within the scope of the present invention.

A first group of compounds according to the present invention, consists of those compounds of formula (I) wherein one or more of the following restrictions apply;

Y represents —$C_{3-9}$alkyl-, —$C_{1-5}$alkyl-$NR^6$—$C_{1-5}$alkyl-, —$C_{1-5}$alkyl-$NR^7$—CO—$C_{1-5}$alkyl-, —$C_{1-6}$alkyl-NH—CO—, —$C_{1-3}$alkyl-NH—CO-$Het^1$-, —$C_{1-6}$alkyl-$NR^8$-$Het^2$ —$X^1$— represents —O—, or —O—$C_{1-2}$alkyl-; in particular $X^1$ represents —O—;

—$X^2$— represents a direct bond, —$C_{1-2}$alkyl- or $NR^5$—$C_{1-2}$alkyl-;

$R^1$ represents hydrogen, cyano, halo, hydroxy, $C_{1-4}$alkyl, $Het^3$, $Het^3$-O— or $Ar^1$—O—; in particular $R^1$ represents hydrogen, cyano, halo or $Het^3$-O—;

$R^2$ represents hydrogen;

$R^3$ represents hydroxy; $C_{1-4}$alkyloxy; or $C_{1-4}$alkyloxy- substituted with one or where possible two or more substituents each independently selected from $Het^4$, hydroxy, $C_{1-4}$alkyloxy-, halo, $NR^9R^{10}$, $C_{1-4}$alkyl-O—C(=O)—O— and oxiranyl;

$R^5$ represents hydrogen, $C_{1-4}$alkyl, $C_{1-4}$alkyloxycarbonyl-, $Ar^3$—S(=O)— or $Ar^3$—S(=O)$_2$— wherein said $C_{1-4}$alkyloxycarbonyl- is optionally substituted with phenyl;

$R^6$ represents hydrogen, $C_{1-4}$alkyl or $C_{1-4}$alkyloxycarbonyl- wherein said $C_{1-4}$alkyloxycarbonyl- is optionally substituted with phenyl;

$R^7$ represents hydrogen or $C_{1-4}$alkyl;

$R^8$ represents hydrogen, $C_{1-4}$alkyl, $Ar^5$—S(=O)—, $Ar^5$—S(=O)$_2$— or $C_{1-4}$alkyloxycarbonyl; in particular $R^8$ represents hydrogen, $C_{1-4}$alkyl or $Ar^5$—S(=O)$_2$—;

$R^9$ and $R^{10}$ each independently represent hydrogen; $C_{1-4}$alkyl or $C_{1-4}$alkyl substituted with one or where possible two or more substituents selected from hydroxy, $C_{1-4}$alkyloxy, $C_{1-4}$alkyl-S(=O), $C_{1-4}$alkyl-S(=O)$_2$, halo, or $C_{1-4}$alkyloxy-$C_{1-4}$alkyloxy-; in particular $R^9$ and $R^{10}$ each independently represent hydrogen; $C_{1-4}$alkyl or $C_{1-4}$alkyl substituted with one or where possible two or more substituents selected from hydroxy, $C_{1-4}$alkyloxy or $C_{1-4}$alkyl-S(=O)$_2$;

$Het^1$ represents pyrrolidinyl or piperidinyl wherein said $Het^1$ is optionally substituted with one or where possible two or more substituents selected from hydroxy, or $C_{1-4}$alkyl; in particular $Het^1$ represents pyrrolidinyl optionally substituted with hydroxy or $C_{1-4}$alkyl;

$Het^2$ represents pyrrolidinyl or piperidinyl wherein said $Het^2$ is optionally substituted with one or where possible two or more substituents selected from hydroxy, or $C_{1-4}$alkyl; in particular $Het^2$ represents pyrrolidinyl optionally substituted with hydroxy or $C_{1-4}$alkyl;

$Het^3$ represents morpholinyl, piperidinyl, piperazinyl or pyrrolidinyl wherein said $Het^3$ is optionally substituted with one or where possible two or more substituents selected from hydroxy or $C_{1-4}$alkyl; in particular $Het^3$ represents piperidinyl optionally substituted with hydroxy or $C_{1-4}$alkyl;

$Het^4$ represents morpholinyl, piperidinyl, pyrrolidinyl, 1,1-dioxothiomorpholinyl, or piperazinyl wherein said $Het^4$ is optionally substituted with one or where possible two or more substituents selected from hydroxy; $C_{1-4}$alkyl; amino; $C_{1-4}$alkyl-S(=O)—; $C_{1-4}$alkyl-S(=O)$_2$—; $C_{1-4}$alkyl substituted with one or where possible two or more substituents selected from hydroxy and $C_{1-4}$alkyl-C(=O)—NH—; or with $C_{1-4}$alkyl-C(=O)— optionally substituted with one or where possible two or more substituents selected from hydroxy, $C_{1-4}$alkyloxy and $C_{1-4}$alkylsulfonyl; in particular $Het^4$ represents morpholinyl, piperidinyl, pyrrolidinyl, 1,1-dioxothiomorpholinyl, or piperazinyl wherein said $Het^4$ is optionally substituted with one or where possible two or more substituents selected from hydroxy; $C_{1-4}$alkyl; amino; $C_{1-4}$alkyl-S(=O)—; $C_{1-4}$alkyl-S(=O)$_2$—; $C_{1-4}$alkyl substituted with one or where possible two or more substituents selected from hydroxy and $C_{1-4}$alkyl-C(=O)—NH—; or with $C_{1-4}$alkyl-C(=O)— optionally substituted with $C_{1-4}$alkylsulfonyl;

$Ar^3$ and $Ar^5$ each independently represent phenyl optionally substituted with nitro, cyano, hydroxy, or $C_{1-4}$alkyloxy-; in particular $Ar^3$ and $Ar^5$ each independently represent phenyl optionally substituted with nitro.

Another group of compounds according to the present invention, consists of those compounds of formula (I) wherein the following restriction applies;

$R^3$ represents hydroxy; $C_{1-4}$alkyloxy; or $C_{1-4}$alkyloxy- substituted with one or where possible two or more substituents each independently selected from $Het^4$, hydroxy, $C_{1-4}$alkyloxy-, halo, $NR^9R^{10}$, $C_{1-4}$alkyl-O—C(=O)—O—, $Ar^2$, $NR^{11}R^{12}$-carbonyl and $Het^5$-carbonyl;

Another group of compounds according to the present invention, consists of those compounds of the first group wherein the following restriction applies;

$R^3$ represents hydroxy; $C_{1-4}$alkyloxy; or $C_{1-4}$alkyloxy- substituted with one or where possible two or more substituents each independently selected from $Het^4$, hydroxy, $C_{1-4}$alkyloxy-, halo, $NR^9R^{10}$, and $C_{1-4}$alkyl-O—C(=O)—O—;

Another group of compounds according to the present invention, consists of those compounds of formula (I) wherein one or more of the following restrictions apply;

Y represents —$C_{3-9}$alkyl-, —$C_{1-5}$alkyl-$NR^6$—$C_{1-5}$alkyl- or —$C_{1-5}$alkyl-$NR^7$—CO—$C_{1-5}$alkyl-;

$X^1$ represents —O—;

$X^2$ represents $NR^5$—$C_{1-2}$alkyl-;

$R^1$ represents hydrogen, halo or $Het^3$-O—;

$R^2$ represents hydrogen;

$R^3$ represents hydroxy, $C_{1-4}$alkyloxy- or $C_{1-4}$alkyloxy substituted with one or two substituents each independently selected from $Het^4$, hydroxy, $C_{1-4}$alkyloxy-, $C_{1-4}$alkyloxy-$C_{1-4}$alkyloxy and $NR^9R^{10}$;

$R^5$ represents hydrogen or $C_{1-4}$alkyl; in particular $R^5$ represents hydrogen or methyl;

$R^6$ represents hydrogen or $C_{1-4}$alkyl; in particular $R^6$ represents hydrogen or methyl;

$R^7$ represents hydrogen;

$R^9$ and $R^{10}$ each independently represent hydrogen; $C_{1-4}$alkyl-S(=O)—$C_{1-4}$alkyl-C(=O)—; $C_{1-4}$alkyl-S(=O)$_2$—$C_{1-4}$alkyl-C(=O)—; $C_{1-4}$alkyl or $C_{1-4}$alkyl substituted with hydroxy;

Het$^3$ represents pyridinyl optionally substituted with $C_{1-4}$alkyl; in particular Het$^3$ represents pyridinyl optionally substituted with methyl;

Het$^4$ represents morpholinyl, piperidinyl or piperazinyl wherein said Het$^4$ is optionally substituted with hydroxy-$C_{1-4}$alkyl or $C_{1-4}$alkyl-S(=O)$_2$—$C_{1-4}$alkyl-;

A further interesting group of compounds consists of those compounds of formula (I) selected from the group consisting of;

1-piperidineethanol, alpha-[[(8,9,10,11,12,13,14,20-octahydro-13-methyl-4,6-etheno[1,3]dioxolo[4,5-q]pyrimido[4,5-b][6,1,12]benzoxadiazacyclopentadecin-21-yl)oxy]methyl]-, (alphaS)-4,6-etheno[1,3]dioxolo[4,5-q]pyrimido[4,5-b][6,1,12]benzoxadiazacyclopentadecine, 8,9,10,11,12,13,14,20-octahydro-21-(2-methoxyethoxy)-13-methyl-ethanol,2-[methyl[3-[(8,9,10,11,12,13,14,20-octahydro-13-methyl-4,6-etheno[1,3]dioxolo[4,5-q]pyrimido[4,5-b][6,1,12]benzoxadiazacyclopentadecin-21-yl)oxy]propyl]amino]-propanamide, 3-(methylsulfonyl)-N-[3-[(8,9,10,11,12,13,14,20-octahydro-13-methyl-4,6-etheno[1,3]dioxolo[4,5-q]pyrimido[4,5-b][6,1,12]benzoxadiazacyclopentadecin-21-yl)oxy]propyl]-5,7-etheno-1H-[1,3]dioxolo[4,5-r]pyrimido[4,5b][6,1,10,13]benzoxatriazacyclohexadecine, 9,10,11,12,13,14,15,16-octahydro-15-methyl-22-[3-(4-methyl-1-piperazinyl)propoxy]-5,7-etheno-1H-[1,3]dioxolo[4,5-r]pyrimido[4,5-b][6,1,10,13]benzoxatriazacyclohexadecine, 9,10,11,12,13,14,15,16-octahydro-22-[2-(2-methoxyethoxy)ethoxy]-15-methyl-ethanol, 2-[methyl[3-[(9,10,11,12,13,14,15,16-octahydro-15-methyl-5,7-etheno-1H-[1,3]dioxolo[4,5-r]pyrimido[4,5-b][6,1,10,13]benzoxatriazacyclohexadecin-22-yl)oxy]propyl]amino]-5,7-etheno-13H-[1,3]dioxolo[4,5-r]pyrimido[4,5b][6,1,10,13]benzoxatriazacyclohexadecin-13-one, 1,9,10,11,12,14,15,16-octahydro-14,15-dimethyl-22-[3-(4-morpholinyl)propoxy]-, (14S)-4,6-etheno[1,3]dioxolo[4,5-q]pyrimido[4,5-b][6,1,12]benzoxadiazacyclopentadecine, 8,9,10,11,12,13,14,20-octahydro-21-methoxy-16-[(6-methyl-3-pyridinyl)oxy]- 5,7-etheno-13H-[1,3]dioxolo[4,5-r]pyrimido[4,5-b][6,1,10,13]benzoxatriazacyclohexadecin-13-one, 1,9,10,11,12,14,15,16-octahydro-22-[2-(2-methoxyethoxy)ethoxy]-14,15-dimethyl-, (14S)-4,6-etheno[1,3]dioxolo[4,5-q]pyrimido[4,5-b][6,1,12]benzoxadiazacyclopentadecine, 16-bromo-8,9,10,11,12,13,14,20-octahydro-21-methoxy-5,7-etheno-1H-[1,3]dioxolo[4,5-r]pyrimido[4,5-b][6,1,10,13]benzoxatriazacyclohexadecine, 9,10,11,12,13,14,15,16-octahydro-22-methoxy-12,15-dimethyl-5,7-etheno-13H-[1,3]dioxolo[4,5-r]pyrimido[4,5-b][6,1,10,13]benzoxatriazacyclohexadecin-13-one,1,9,10,11,12,14,15,16-octahydro-22-methoxy-14,15-dimethyl-, (14S)-5,7-etheno-1H-[1,3]dioxolo[4,5-r]pyrimido[4,5-b][6,1,10,13]benzoxatriazacyclohexadecin-22-ol, 9,10,11,12,13,14,15,16-octahydro-15-methyl-4,6-etheno[1,3]dioxolo[4,5-q]pyrimido[4,5-b][6,1,12]benzoxadiazacyclopentadecine, 8,9,10,11,12,13,14,20-octahydro-13-methyl-21-[3-(4-methyl-1-piperazinyl)propoxy]-1-piperazineethanol, 4-[3-[(8,9,10,11,12,13,14,20-octahydro-13-methyl-4,6-etheno[1,3]dioxolo[4,5-q]pyrimido[4,5-b][6,1,12]benzoxadiazacyclopentadecin-21-yl)oxy]propyl]-5,7-etheno-1H-[1,3]dioxolo[4,5-r]pyrimido[4,5-b][6,1,10,13]benzoxatriazacyclohexadecine, 9,10,11,12,13,14,15,16-octahydro-15-methyl-22-[3-[4-(methylsulfonyl)-1-piperidinyl]propoxy]-

Other special group of compounds are:
those compounds of formula (I) wherein —$X^1$— represents —O—;
those compounds of formula (I) wherein —$X^2$— represents —NR$^5$—$C_{1-2}$alkyl, in particular —N(CH$_3$)—$C_{1-2}$alkyl-;
those compounds of formula (I) wherein $R^1$ is fluoro, chloro or bromo;
those compounds of formula (I) wherein $R^2$ is cyano;
those compounds of formula (I) wherein $R^3$ is at position 7 of the structure of formula (I).
those compounds of formula (I) wherein $R^3$ represents $C_{1-4}$alkyloxy substituted with hydroxy and one substituent selected from NR$^9$R$^{10}$ or Het$^4$-;
those compounds of formula (I) wherein $R^3$ represents $C_{1-4}$alkyloxy substituted with $C_{1-4}$alkyloxy-$C_{1-4}$alkyloxy;
those compounds of formula (I) wherein $R^3$ represents $C_{1-4}$alkyloxy, more in particular methoxy;
those compounds of formula (I) wherein $R^9$ is hydrogen or methyl and $R^{10}$ represents $C_{1-4}$alkyl-S(=O)$_2$—$C_{1-4}$alkyl-C(=O)—, $C_{1-4}$alkyl or hydroxy-$C_{1-4}$alkyl; in particular those compounds of formula (I) wherein $R^9$ is hydrogen or methyl and $R^{10}$ represents methyl-S(=O)$_2$—(CH$_2$)$_2$—C(=O)— or hydroxy-$C_{1-4}$alkyl-; more in particular
those compounds of formula (I) wherein $R^9$ represents hydrogen or methyl and $R^{10}$ represents methyl-S(=O)$_2$—(CH$_2$)$_2$—C(=O)— or hydroxy-ethyl-;
those compounds of formula (I) wherein Het$^4$ represents piperidinyl or piperazinyl wherein said Het$^4$ is substituted with methyl or hydroxyethyl.
those compounds of formula (I) selected from the group consisting of
4,6-ethanediylidene[1,3]dioxolo[4,5-q]pyrimido[4,5-b][6,1,12]benzoxadiazacyclopentadecine, 8,9,10,11,12,13,14,20-octahydro-13-methyl-21-[(2S)-oxiranylmethoxy]-5,7-ethanediylidene-13H-[1,3]dioxolo[4,5-r]pyrimido[4,5-b][6,1,10,13]benzoxatriazacyclohexadecin-13-one,1,9,10,11,12,14,15,16-octahydro-14,15-dimethyl-22-[(2S)-oxiranylmethoxy]-,(14S)-

In a further embodiment of the present invention, the $X^2$ substituent is at position 2', the $R^1$ substituent represents hydrogen or halo and is at position 4', the $R^2$ substituent is at position 2 and the $R^3$ substituent at position 7 of the structure of formula (I). Alternatively, the $X^2$ substituent is at position 3', the $R^1$ substituent represents hydrogen or halo and is at position 4', the $R^2$ substituent is at position 2 and the $R^3$ substituent at position 7 of the structure of formula (I).

The compounds of this invention can be prepared by any of several standard synthetic processes commonly used by those skilled in the art of organic chemistry and described for instance in the following references; "Heterocyclic Compounds"—Vol. 24 (part 4) p 261-304 Fused pyrimidines, Wiley—Interscience; Chem. Pharm. Bull., Vol 41(2), 362-368 (1993); J. Chem. Soc., Perkin Trans. 1, 2001, 130-137.

As further exemplified in the experimental part hereinafter, a particular group of compounds are those compounds of formula (I) were —$X^1$— represents —O— hereinafter referred to as the compounds of formula (3). Said compounds are generally prepared starting from the known 6-acetoxy-4-chloro-7-methoxy quinazoline (II') which can be prepared from commercially available veratric acid and 4-hydroxy-3-methoxy benzoic acid, respectively.

Coupling of the latter with suitable substituted benzodioxole-amines (III') under standard conditions, for example stirred in 2-propanol at an elevated temperature ranging from 40-100° C. during 3-12 h, furnish the intermediate compounds (IV') (Scheme 1).

Scheme 1:

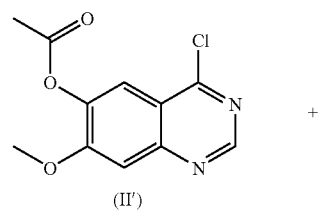

(II')

+

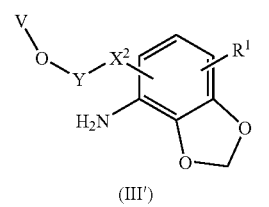

(III')

↓

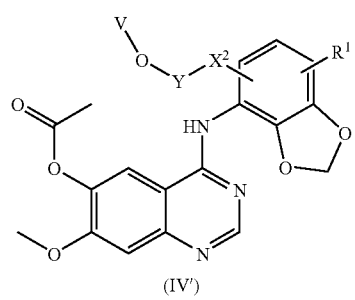

(IV')

V=hydrogen or a protective group such as for example, methylcarbonyl, t-butyl, methyl, ethyl, benzyl or trialkylsilyl groups $X^2$, Y, $R^1$ and $R^2$ are defined as for the compounds of formula (I)

Deprotection of the intermediates of formula (IV') as described in *Protective Groups in Organic Synthesis* by T. W. Greene and P. G. M. Wuts, $3^{rd}$ edition, 1998, followed by ring closure under Mitsunobu conditions give the macrocyclic compounds (1) of the present invention (I), wherein $R^3$ represents methoxy (Scheme 2).

Scheme 2:

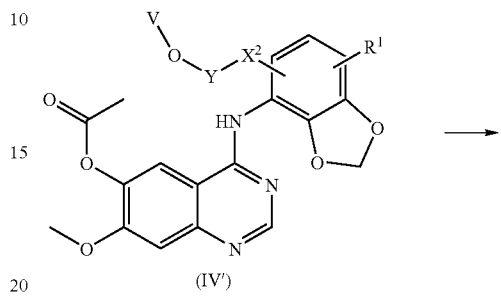

(IV')

↓

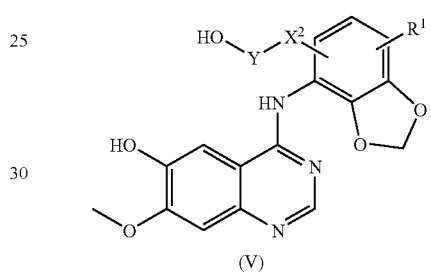

(V)

↓

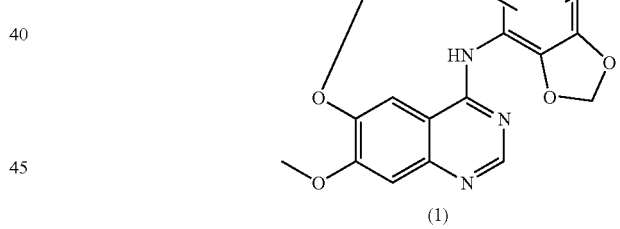

(1)

V=hydrogen or a protective group such as for example, methylcarbonyl, t-butyl, methyl, ethyl, benzyl or trialkylsilyl groups $X^2$, Y, $R^1$ and $R^2$ are defined as for the compounds of formula (I)

Further modification of said methoxy group provides the compounds of the present invention (I), wherein $R^3$ is other than methoxy (Scheme 3). In brief, said macrocyclic compounds of formula (1) are demethylated using art known conditions such as for example by heating with concentrated HI or HBr. Specific examples of this demethylation reaction are provided in the examples A1k); A2i) & A5i) hereinafter. Subsequent alkylation with an appropriate alcohol under art known conditions provides the compounds of the present invention wherein R is other than methyl (3). The alkylation is typically performed under Mitsunobu conditions, such as for example provided in the examples A1l); A2k) & A5j) hereinafter.

Scheme 3:

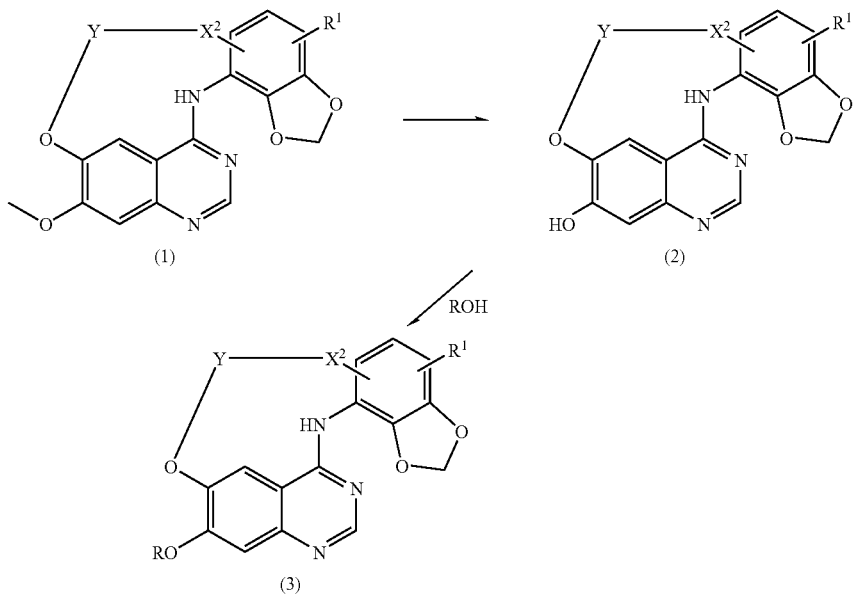

wherein R represents $C_{1-4}$alkyl- or R represents $C_{1-4}$alkyl substituted with one or where possible two or more substituents selected from Het⁴, hydroxy, $C_{1-4}$alkyloxy-, halo, $NR^9R^{10}$, $C_{1-4}$alkyl-O—C(=O)—O—, Ar², $NR^{11}R^{12}$-carbonyl and Het⁵-carbonyl. Ar², Het⁴, Het⁵, Y, X², R¹, R⁹, R¹⁰, R¹¹ and R¹² are defined as for the compounds of formula (I) hereinbefore.

As exemplified hereinafter, a particular group of compounds are those compounds of formula (3) wherein R represents $C_{1-4}$alkyl substituted with $NR^9R^{10}$ or Het⁴ wherein said Het⁴ is attached to the remainder of the molecule through the nitrogen atom. Said compounds of general formula (5), are generally made according to synthesis scheme 4 departing from the compounds of general formula (2).

Scheme 4

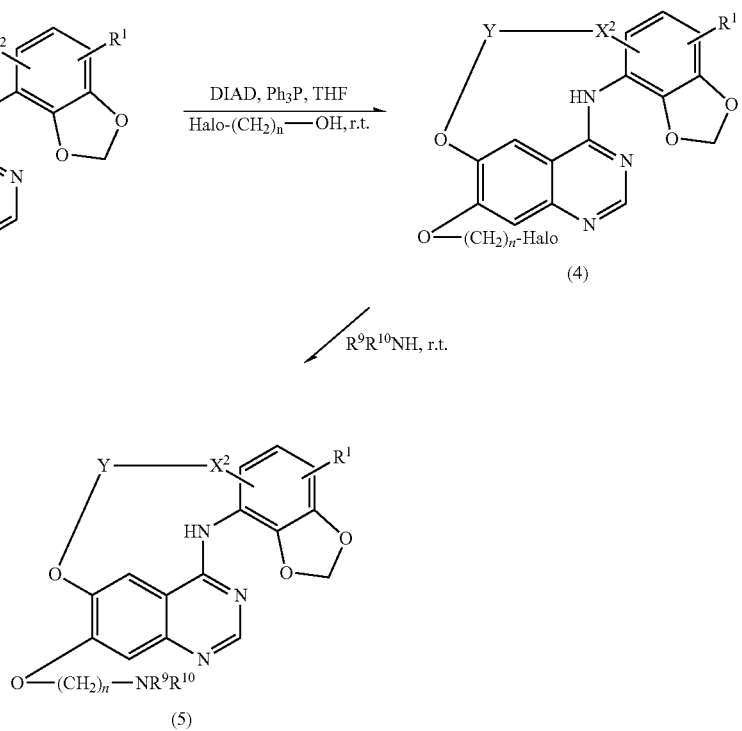

wherein n=1, 2, 3 or 4; Y; $X^2$; $R^1$; $R^9$ and $R^{10}$ are defined as for the compounds of formula (I), or $R^7$ and $R^8$ taken together with the nitrogen atom to which they are attached from a heterocycle wherein said heterocycle is defined as $Het^4$ for the compounds of formula (I) hereinbefore.

Again, in a first step the alcohol (2) was alkylated with an appropriate haloalkylalcohol under Mitsunobu conditions, followed by an amination under art known conditions.

Alternatively to the above, and in particular for those compounds of formula (5) wherein the $C_{1-4}$alkyl moiety is further substituted with hydroxy-, said compounds are made using a nucleophilic addition reaction departing from the oxirane analog 3' (Scheme 5)

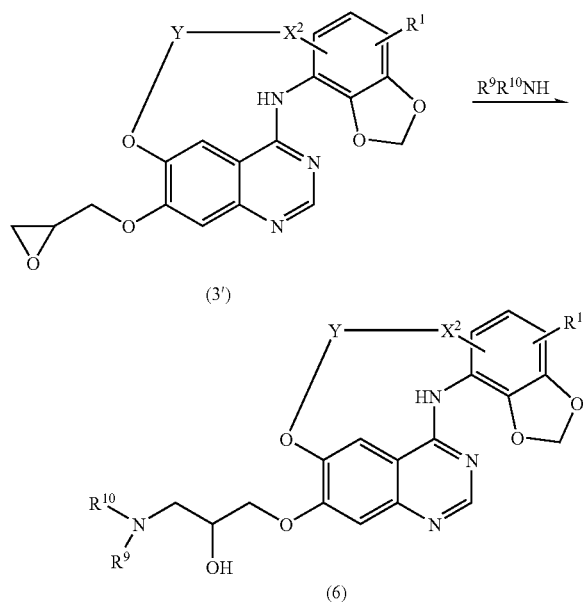

wherein Y; $X^2$; $R^1$; $R^9$ and $R^{10}$ are defined as for the compounds of formula (I), or $R^9$ and $R^{10}$ taken together with the nitrogen atom to which they are attached from a heterocycle wherein said heterocycle is defined as $Het^4$ for the compounds of formula (I) hereinbefore.

This reaction is performed using art known conditions, such as for example provided in the example B1 hereinafter.

The Mitsunobu ring closure as provided in Scheme 2 hereinbefore, is particularly useful for those compounds of formula (I) wherein $X^1$ represents —O—; $X^2$ represents $NR^5$—$C_{1-2}$alkyl-; and —Y— represents —$C_{3-9}$alkyl- hereinafter referred to as the compounds of formula (7). For said compounds, the substituted benzodioxole amine (12) is prepared from the known 4-hydroxy-3-methoxy-2-nitro benzaldehydes (8) wherein $X^3$ is hydrogen of halogen (Scheme 6). Demethylation using art known conditions such as for example provided in example A7a) hereinafter, i.e. using a mixture of suitable solvents like pyridine/$CH_2Cl_2$ in the presence of $AlCl_3$ (anhydrous), provides the dialcohol (9) (Scheme 6a) that after alkylation with an appropriate alkylhalide such as dichloro- or diiodo-methane, provides the benzodioxole derivatives of general formula (10) (Scheme 6b). This alkylation reaction, also known as the Williamson reaction, involves the treatment of the halide with an aroxide ion which is prepared by removal of a proton from the alcohols using for example $K_2CO_3$ in DMF; solid KOH in $Me_2SO$; HgO and $HBF_4$ in $CH_2Cl_2$ or a copper (I) tertiary alkoxide. More specific examples are provided in examples A7b) & A12b) hereinafter.

To introduce the $C_{3-9}$alkyl ethylene linker into the molecule, a reductive amination followed by an optional protection of the free amine in case a primary amine has been used (Scheme 6d), yields the nitrobenzodioxole derivatives of general formula (11) (Scheme 6c). The reductive amination reaction is performed using art known conditions, wherein the aldehyde is treated with an appropriate primary or secondary amine in the presence of hydrogen and a hydrogenation catalyst, or using other reducing agents such as sodium borohydride, ironpentacarbonyl, $NaBH(OAc)_3$ and formic acid in a suitable solvent such as ethanol or dichloroethane. More specific examples of the reductive amination are provided in examples A7c) & A12e) hereinafter. The optional protection of the amine can be done using a suitable protecting group such as, for example, ter-butyloxycarbonyl or benzyloxycarbonyl, as described in *Protective Groups in Organic Synthesis* by T. W. Greene and P. G. M. Wuts, $3^{rd}$ edition, 1998.

Reduction of the nitrobenzodioxole derivatives (11) (Scheme 6e) ultimately yields the benzodioxolo amines of formula (12). This reduction is performed using standard conditions, for example using hydrogenolysis ($H_2$, Pt/C, thiophene, MeOH) or tin(II)chloride ($SnCl_2$, $H_2$, EtOH).

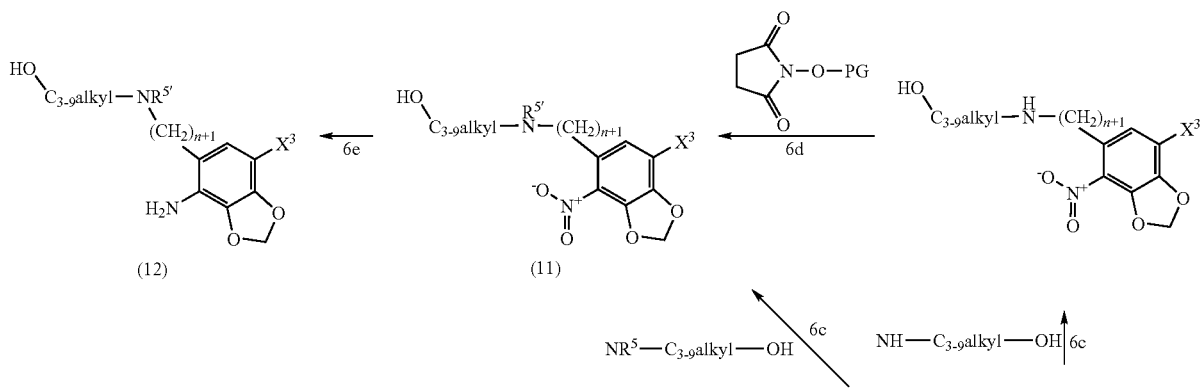

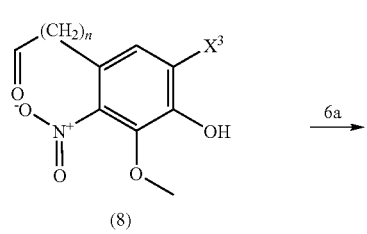 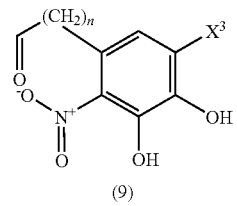 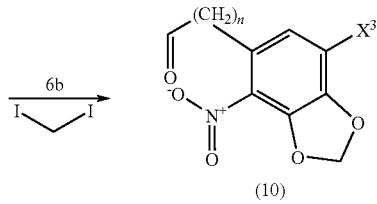

(8) → 6a → (9) → 6b → (10)

wherein n=0 or 1; $X_1$ represents hydrogen or halo; $R^5$ is defined as for the compounds of formula (I) hereinbefore and $R^{5'}$ includes the definition of $R^5$ as defined for the compounds of formula (I) hereinbefore and a protecting group such as for example ter-butyloxycarbonyl or benzyloxycarbonyl.

For those compounds of formula (I) wherein;
the —$X^1YX^2$— linker comprises a diamine or an amide, in particular for those compounds wherein $X^1$ represents —O—; $X^2$ represents $NR^5$—$C_{1-2}$alkyl- and Y represents $C_{1-5}$alkyl-$NR^6$—$C_{1-5}$alkyl-, $C_{1-5}$alkyl-$NR^7$—CO—$C_{1-5}$alkyl-, $C_{1-6}$alkyl-NH—CO—, NH—CO—$C_{1-6}$alkyl-, $C_{1-3}$alkyl-NH—CO-$Het^1$-, $C_{1-6}$alkyl-$NR^8$-$Het^2$-, $C_{1-6}$alkyl-CO—NH or CO—NH—$C_{1-6}$alkyl; hereinafter referred to as the compounds of formula (Ia), an alternative synthesis scheme (Scheme 7) to the Mitsunobu ring closure has been applied.

The intermediates of formula (V) are obtained as described hereinbefore. Formation of the corresponding ether (13a) is done using the appropriate aminated alkylhalide under standard conditions, i.e. using the Williamson Reaction wherein the halide is treated with an aroxide ion, which is prepared by removal of a proton from the alcohols using for example $K_2CO_3$ in DMF; solid KOH in $Me_2SO$; HgO and $HBF_4$ in $CH_2Cl_2$ or a Copper (I) tertiary alkoxide. A more specific example is provided in example A5e) hereinafter. Deprotection followed by ring closure provides the target compounds of formula (Ia). Deprotection is done under standard conditions, such as for example described in *Protective Groups in Organic Synthesis* by T. W. Greene and P. G. M. Wuts, $3^{rd}$ edition, 1998. The ring closure is either a typical amide formation or the replacement of a hydroxy group by an amine.

The amide formation is done under art known conditions, such as for example using coupling agents to proceed in good yield at room temperature or slightly above. Coupling agents are those that are normally used in peptide synthesis such as for example dicyclohexylcarbodiimide; N,N'-carbonyldiimidazole, $POCl_3$, chlorosulfonyl isocyanate, a mixture of $Bu_3P$ and PhCNO and a mixture of DIPEA and HBTU.

The replacement of the hydroxy group with an amine, i.e the conversion of an alcohol into an amine is done under art known conditions, such as for example by treatment with triphenylphosphine dibromide in the presence of triethylamine or by treatment with triphenylphosphine in the presence of bis(1-methylethyl)-diazene-di-carboxylate.

Scheme 7

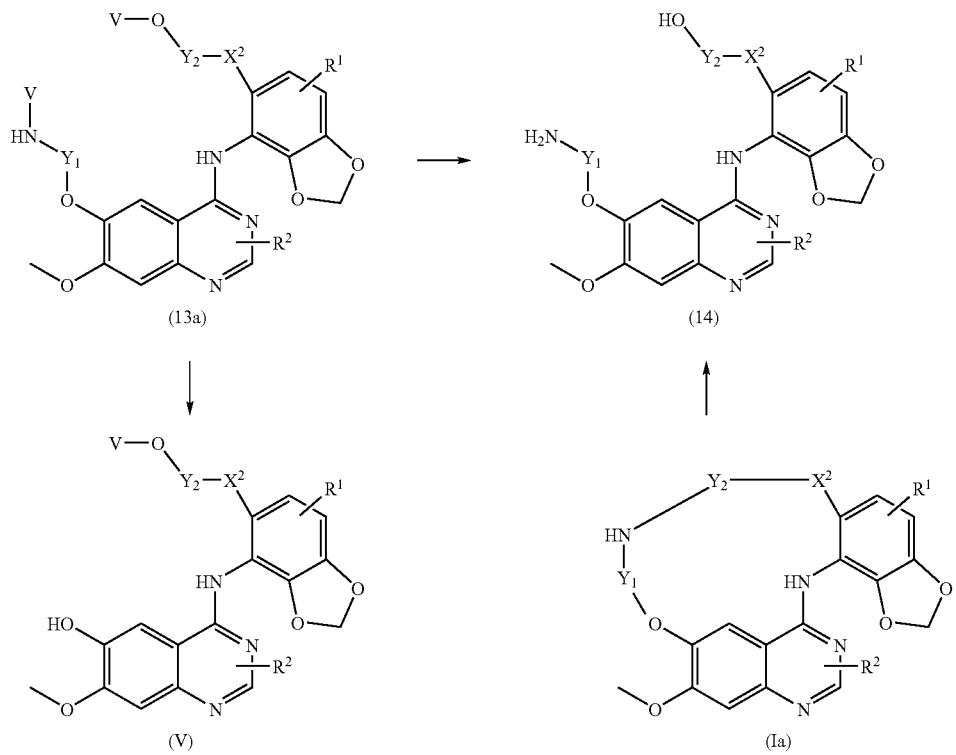

For those compounds of formula (I) wherein the —X$^1$YX$^2$— linker comprises a diamine, in particular for those compounds of formula (I) wherein X$^1$ represents —O—; X$^2$ represents NR$^5$—C$_{1-2}$alkyl- and Y represents C$_{1-5}$alkyl-NR$^6$—C$_{1-5}$alkyl- or C$_{1-6}$alkyl-NR$^8$—Het$^2$- as an alternative to Scheme 7, intermediate (V) can by alkylated under similar conditions as described in Scheme 7 hereinbefore, i.e. using the Williamson reaction with a dihalogenated alkyl instead. In the thus obtained intermediate (15), the deprotected alcohol is first converted into a secondary amine using similar reaction conditions as described in Scheme 7 hereinbefore, followed by a final ring closure that now consists of an alkylation reaction of the secondary amine with the alkylhalide present on the quinazoline moiety. Again, this alkylation reaction is done under standard conditions such as for example in a suitable solvent like CH$_3$CN in the presence of tetrabutylammonium iodide and Cs$_2$CO$_3$. This and other reaction conditions, are provided in more detail in the examples hereinafter.

(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;

(vi) where the compound of formula (I) is obtained as a mixture of (R) and (S) enantiomers, resolving the mixture is necessary to obtain the desired enantiomer.

Compounds of formula (I), N-oxides, addition salts, quaternary amines and stereochemically isomeric forms thereof can be converted into further compounds according to the invention, using procedures known in the art.

It will be appreciated by those skilled in the art, that in the processes described above, the functional groups of intermediate and macrocyclic compounds which are used in a next reaction step, may need to be blocked by protective groups.

Functional groups, which are desirable to protect, include hydroxy, amino and carboxylic acid. Suitable protective Scheme 8

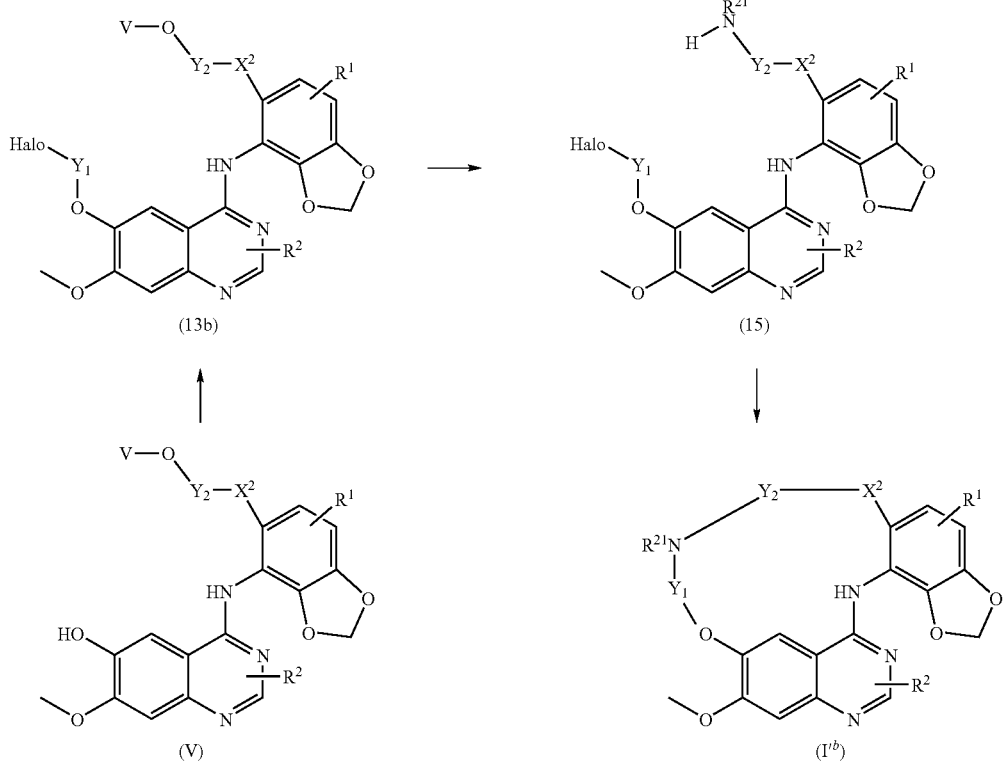

Where necessary or desired, any one or more of the following further steps in any order may be performed:
(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;

groups for hydroxyl, include trialkylsilyl groups (e.g. tert-butyldimethylsilyl, tert-butyldiphenylsilyl or trimethylsilyl), benzyl and tetrahydropyranyl. Suitable protective groups for amino, include tert-butyloxycarbonyl or benzyloxycarbonyl. Suitable protecting groups for carboxylic acid, include C$_{(1-6)}$alkyl or benzyl esters.

The protection and deprotection of functional groups may take place before or after a reaction step.

Additionally, the N-atoms in compounds of formula (I) can be methylated by art-known methods using CH$_3$—I in a suitable solvent such as, for example, 2-propanone, tetrahydrofuran or dimethylformamide.

The compounds of formula (I) can also be converted into each other, following art-known procedures of functional group transformation of which, some examples are mentioned hereinafter.

The compounds of formula (I), may also be converted to the corresponding N-oxide forms following art-known procedures for converting a trivalent nitrogen into its N-oxide form. Said N-oxidation reaction, may generally be carried out by reacting the starting material of formula (I) with 3-phenyl-2-(phenylsulfonyl)-oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like hydrocarbons e.g. toluene, ketones, 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as fractional crystallization and chromatographic techniques, e.g. counter-current distribution, liquid chromatography and the like.

Some of the compounds of formula (I) and some of the intermediates in the present invention, may contain an asymmetric carbon atom. Pure stereochemically isomeric forms of said compounds and said intermediates, can be obtained by the application of art-known procedures. For example, diastereoisomers can be separated by physical methods such as fractional crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, fractional crystallization or chromatographic techniques, e.g. liquid chromatography and the like methods; and finally converting said separated diastereomeric salts or compounds into the corresponding enantiomers. Pure stereochemically isomeric forms, may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates, involves liquid chromatography, in particular liquid chromatography using a chiral stationary phase.

Some of the intermediates and starting materials as used in the reaction procedures mentioned hereinabove, are known compounds and may be commercially available or may be prepared according to art-known procedures.

As described in the experimental part hereinafter, the growth inhibitory effect and anti-tumour activity of the present compounds has been demonstrated in vitro in enzymatic assays on the receptor tyrosine kinases such as for example EGFR, Abl, Fyn, Flt1, Hck or the Src kinase family such as for example Lyn, Yes and c-Src. In an alternative assay, the growth inhibitory effect of the compounds was tested on a number of carcinoma cell lines, in particular the ovarian carcinoma cell line SKOV3 and the squamous carcinoma cell line A431 using art known cytotoxicity assays such as MTT.

Accordingly, the present invention provides the compounds of formula (I) and their pharmaceutically acceptable N-oxides, addition salts, quaternary amines and stereochemically isomeric forms for use in therapy. More particular in the treatment or prevention of cell proliferation mediated diseases. The compounds of formula (I) and their pharmaceutically acceptable N-oxides, addition salts, quaternary amines and the stereochemically isomeric forms may hereinafter be referred to as compounds according to the invention.

The compounds according to the invention, are particularly useful as a selective inhibitor of the motility of tumour cells and as a selective inhibitor of the dissemination and invasiveness of mammalian cancer cells leading to inhibition of metastatic tumour growth. Accordingly, it has been recognised that an inhibitor of such non-receptor tyrosine kinases, should be of value in the treatment of common human cancers such as gastrointestinal cancer, for example colon, rectal and stomach cancer; breast cancer; non-small cell lung cancers, such as adenocarcinomas and squamous cell cancer of the lung; bladder cancer; oesophageal cancer; cancer of the prostate; ovarian cancer; and pancreatic cancer. An inhibitor of a non-receptor tyrosine kinase would also be useful in the prevention and treatment of uncontrolled cellular proliferation which arises from various non-malignant diseases such as bone diseases (for example osteopetrosis, Paget's disease, metastatic disease in bone and tumour-induced hypercalcaemia), inflammatory diseases (for example rheumatoid arthritis and inflammatory bowel disease), fibrotic diseases (for example hepatic cirrhosis and lung fibrosis), glumerulonephritis, multiple sclerosis, psoriasis, hypersensitivity reactions of the skin, blood vessel diseases (for example atherosclerosis and restinosis), allergic asthma, insulin-dependent diabetes, diabetic retinopathy and diabetic nephropathy.

In view of the utility of the compounds according to the invention, a method of treating a cell proliferative disorder such as atherosclerosis, restenosis and cancer is provided, the method comprising administering to an animal in need of such treatment, for example, a mammal including humans, suffering from a cell proliferative disorder, a therapeutically effective amount of a compound according to the present invention.

Said method comprising the systemic or topical administration of an effective amount of a compound according to the invention, to animals, including humans. One skilled in the art will recognize that, a therapeutically effective amount of the Src family of non-receptor tyrosine kinase inhibitors of the present invention, is the amount sufficient to induce the growth inhibitory effect and that this amount varies inter alia, depending on the size, the type of the neoplasia, the concentration of the compound in the therapeutic formulation, and the condition of the patient. Generally, an amount of Src inhibitor to be administered as a therapeutic agent for treating cell proliferative disorder such as atherosclerosis, restenosis and cancer, will be determined on a case by case by an attending physician.

Generally, a suitable dose is one that results in a concentration of the Src inhibitor at the treatment site in the range of 0.5 nM to 200 µM, and more usually 5 nM to 10 µM. To obtain these treatment concentrations, a patient in need of treatment, most likely will be administered between 0.01 mg/kg to 300 mg/kg body weight, in particular from 10 mg/kg to 100 mg/kg body weight. As noted above, the above amounts may vary on a case-by-case basis. In these methods of treatment, the compounds according to the invention are preferably formulated prior to admission. As described herein below, suitable pharmaceutical formulations are prepared by known procedures using well known and readily available ingredients.

Due to their high degree of selectivity as Src inhibitors, the compounds of formula (I) as defined above, are also useful to mark or identify the kinase domain within the receptor tyrosine kinase receptors. To this purpose, the compounds of the present invention can be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}$C-atom or tritium atom.

One particular group, consists of those compounds of formula (I) wherein $R^1$ is a radioactive halogen atom. In principle, any compound of formula (I) containing a halogen atom is prone for radiolabelling by replacing the halogen atom with a suitable isotope. Suitable halogen radioisotopes to this purpose are radioactive iodides, e.g. $^{122}$I, $^{123}$I, $^{125}$I, $^{131}$I; radioactive bromides, e.g. $^{75}$Br, $^{76}$Br, $^{77}$Br and $^{82}$Br, and radioactive fluorides, e.g. $^{18}$F. The introduction of a radioactive halogen atom can be performed by a suitable exchange reaction or by using any one of the procedures as described hereinabove to prepare halogen derivatives of formula (I).

Another interesting form of radiolabelling is by substituting a carbon atom by a $^{11}$C-atom or the substitution of a hydrogen atom by a tritium atom.

Hence, said radiolabelled compounds of formula (I) can be used in a process of specifically marking receptor sites in biological material. Said process comprises the steps of (a) radiolabelling a compound of formula (I), (b) administering this radiolabelled compound to biological material and subsequently (c) detecting the emissions from the radiolabelled compound.

Alternatively, the compounds are labeled with stable isotopes. In this form of labelling, the naturally abundant isotopes of hydrogen, carbon and nitrogen ($^1$H, $^{12}$C and $^{14}$N) are replaced with stable isotopes of these elements ($^2$H [deuterium], $^{13}$C and $^{15}$N, respectively). Labeling with stable isotopes is used for two principal purposes:

Incorporation of stable isotopes into proteins, carbohydrates and nucleic acids facilitates their structural determination at the atomic level.

Metabolic studies exploiting the increased mass of compounds labeled with stable isotopes The term biological material is meant to comprise every kind of material which has a biological origin. More in particular, this term refers to tissue samples, plasma or body fluids but also to animals, specially warm-blooded animals, or parts of animals such as organs.

When used in in vivo assays, the radiolabelled compounds are administered in an appropriate composition to an animal and the location of said radiolabelled compounds is detected using imaging techniques, such as, for instance, Single Photon Emission Computerized Tomography (SPECT) or Positron Emission Tomography (PET) and the like. In this manner, the distribution to the particular receptor sites throughout the body can be detected and organs containing said receptor sites can be visualized by the imaging techniques mentioned hereinabove. This process of imaging an organ by administering a radiolabelled compound of formula (I) and detecting the emissions from the radioactive compound also constitutes a part of the present invention.

In yet a further aspect, the present invention provides the use of the compounds according to the invention in the manufacture of a medicament for treating any of the aforementioned cell proliferative disorders or indications.

The amount of a compound according to the present invention, also referred to here as the active ingredient, which is required to achieve a therapeutic effect will, of course, vary with the particular compound, the route of administration, the age and condition of the recipient, and the particular disorder or disease being treated. A suitable daily dose would be from 0.01 mg/kg to 300 mg/kg body weight, in particular from 10 mg/kg to 100 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case, solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause any significant deleterious effects on the skin. Said additives may facilitate the administration to the skin and/or may aid the preparation of the desired compositions. These compositions may be administered in various ways, e.g., as a transdermal patch, as a spot-on or as an ointment.

It is especially advantageous to formulate the aforementioned pharmaceutical compositions, in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Experimental Part

Hereinafter, the term

'THF' means tetrahydrofuran, 'DMF' means N,N-dimethylformamide, 'EtOAc' means ethyl acetate, 'MgSO$_4$' means magnesium sulphate, 'NaBH(OAc)$_3$' means sodium triacetoxyborohydride, 'CH$_2$Cl$_2$' means dichloromethane, 'Na$_2$SO$_4$' means sodium sulphate, 'CH$_3$OH' means methanol, 'DMA' means dimethylacetamide, 'NaBH$_4$' means sodium tetrahydroborate(1-), 'NaHCO$_3$' means carbonic acid monosodium salt, 'DIAD' means bis(1-methylethyl) ester diazenedicarboxylic acid, 'Et$_3$N' means triethylamine, 'DIPEA' means N-ethyl-N-(1-methylethyl)-2-propanamine, 'K$_2$CO$_3$' means potassium carbonate, 'DIPE' means diisopropyl ether, 'EtOH' means ethanol, 'HBTU' means 1-[bis(dimethylamino)methylene]-1H-benzotriazoliumhexafluorophosphate(1-)3-oxide, "HCTU" means 1-[bis(dimethylamino)methylene]-5-chloro-1H-benzotriazoliumhexafluorophosphate(1-) 3-oxide, 'Cs$_2$CO$_3$' means cesium carbonate, 'Et$_2$O' means diethyl ether, 'CHCl$_3$' means chloroform, 'AlCl$_3$' means aluminum chloride, 'NaOCH$_3$' means methanol, sodium salt, 'NaH$_3$PO$_4$' means phosphoric acid, monosodium salt, 'HCl' means monohydrochloride.

A. Preparation of the Compounds of the Present Invention and Their Intermediates Example A1 a) Preparation of Compound A1

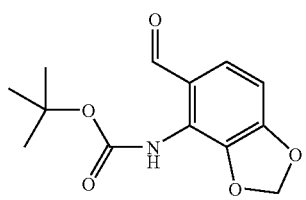 [SMILES: CC(C)(C)OC(=O)Nc1c(C=O)ccc2c1OCO2]

Methyllithium (0.0389 mol) was added dropwise at −78° C. to a solution of (5-bromo-1,3-benzodioxol-4-yl)-1,1-dimethylethyl ester carbamic acid (0.0389 mol) in THF (150 ml) under N$_2$ flow. The mixture was stirred for 15 minutes. Butyllithium (0.0778 mol) was added dropwise. The mixture was stirred for 30 minutes. A solution of DMF (0.389 mol) in THF (50 ml) was added at −78° C. The mixture was stirred for 1 hour, poured onto ice at −78° C. and extracted with EtOAc. The organic layer was separated, dried (MgSO$_4$), filtered and the solvent was evaporated, yielding 16 g of compound A1.

b) Preparation of Compound A2

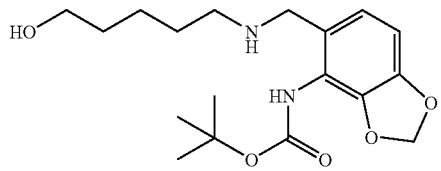 [SMILES: CC(C)(C)OC(=O)Nc1c(CNCCCCCO)ccc2c1OCO2]

Compound A1 (37.7 mmol) and 5-amino-1-pentanol (75.6 mmol) were dissolved in 1,2-dichloroethane (160 ml) and stirred at room temperature for 45 minutes. The mixture was cooled to 0° C. and acetic acid (4.35 ml) was added within 5 minutes. NaBH(OAc)$_3$ (75.5 mmol) was added in portions and stirring at 0° C. was continued for 30 minutes. The mixture was stirred at room temperature for 17 hours, poured onto a saturated aqueous NaHCO$_3$ solution and extracted twice with CH$_2$Cl$_2$. The combined organic layers were dried (Na$_2$SO$_4$), filtered and the solvent was evaporated, yielding 15 g (light oil) of compound A2, used without purification in the next step.

c) Preparation of Copound A3

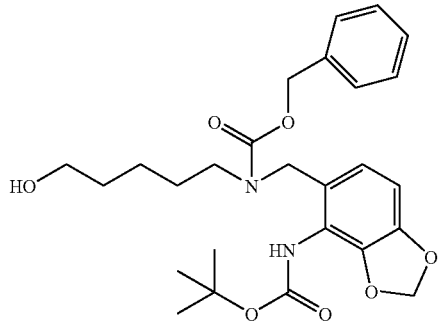 [SMILES: CC(C)(C)OC(=O)Nc1c(CN(CCCCCO)C(=O)OCc2ccccc2)ccc2c1OCO2]

A solution of crude compound A2 (2.26 mmol) in dry CH$_2$Cl$_2$ (10 ml) was cooled to 0° C. 1-[[(Phenylmethoxy)carbonyl]oxy]-2,5-pyrrolidinedione (2.49 mmol) was added in portions. The mixture was stirred for 30 minutes at 0° C. then for one hour at room temperature. The reaction mixture was partitioned between CH$_2$Cl$_2$ and water. The separated organic layer was dried (Na$_2$SO$_4$), filtered and the solvent evaporated. The residue was purified by flash column chromatography over silica gel (eluent: EtOAc/hexane 1:1 to 2:1). The product fractions were collected and the solvent was evaporated, yielding 0.900 g (81.8%, colourless foam) of compound A3.

Analytical HPLC: Method 2 (see part 'Compound identification', method 2), Rt=4.68 (89%). APCI-MS: 487 ([M+H]$^+$), 387 ([M+H-Boc]$^+$), 150 (100)

d) Preparation of Compound A4

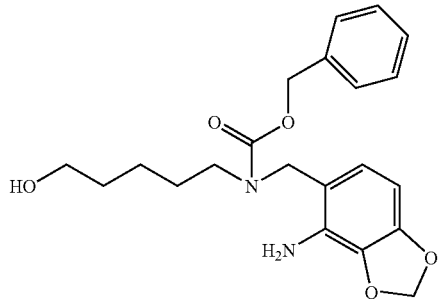 [SMILES: Nc1c(CN(CCCCCO)C(=O)OCc2ccccc2)ccc2c1OCO2]

At 0° C. a solution of compound A3 (3.90 mmol) in CH₂Cl₂ (7.5 ml) was treated with a HCl solution (4M in dioxane) (37 ml). The mixture was allowed to warm to room temperature and stirred for approximately 2 hours, then poured onto a mixture of ice and water. This mixture was extracted with EtOAc. The organic phase was separated, dried (MgSO₄), filtered and concentrated, yielding 1.68 g of compound A4, used without any purification in the next step.

e) Preparation of Compound A5

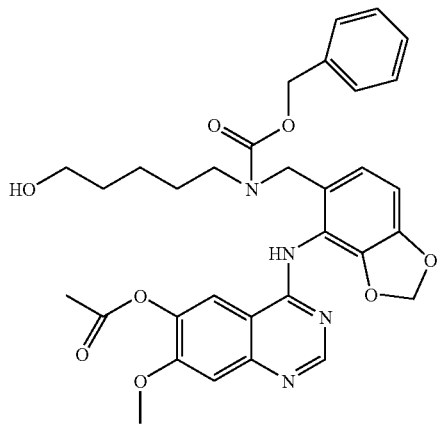 [SMILES: COc1cc2ncnc(Nc3c(CN(CCCCCO)C(=O)OCc4ccccc4)ccc4c3OCO4)c2cc1OC(C)=O]

A solution of crude compound A4 (26.2 mmol) in acetonitrile (130 ml) was treated with 4-chloro-7-methoxy-6-quinazolinol acetate (ester) (26.2 mmol). The mixture was heated to 85° C. for 1.5 hours. The mixture was cooled to room temperature. The solvent was evaporated, the residue was dried in vacuum (18 g of green oil and foam) and was then purified by flash column chromatography over silica gel (eluent: CH₂Cl₂/CH₃OH 100:0 to 95:5). The product fractions were collected and the solvent was evaporated, yielding 14.0 g (89%) of compound A5.

Analytical HPLC: Method 2, Rt=3.71 (98%). APCI-MS: 603 (100, [M+H]⁺)

f) Preparation of Compound A6

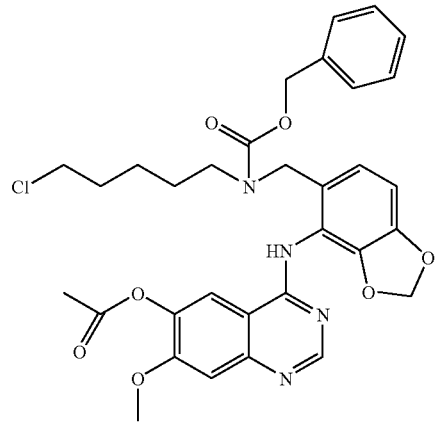 [SMILES: COc1cc2ncnc(Nc3c(CN(CCCCCCl)C(=O)OCc4ccccc4)ccc4c3OCO4)c2cc1OC(C)=O]

A solution of compound A5 (0.166 mmol) in dry DMA (1 ml) was treated with methanesulfonyl chloride (0.83 mmol) and heated for 3 hours at 90-95° C. The residue was partitioned between EtOAc and a saturated aqueous NaHCO₃ solution. The organic layer was separated, washed with water, followed by a saturated aqueous NaCl solution, dried (Na₂SO₄), filtered and the solvent was evaporated. The residue was purified by flash column chromatography over silica gel (eluent: EtOAc). The product fractions were collected and the solvent was evaporated, yielding 0.041 g (40%, colourless foam) of compound A6.

APCI-MS: 621 (100, [M+H]⁺) (measured according to the MS method described in general procedure C from the part 'compound identification')

g) Preparation of Compound A7

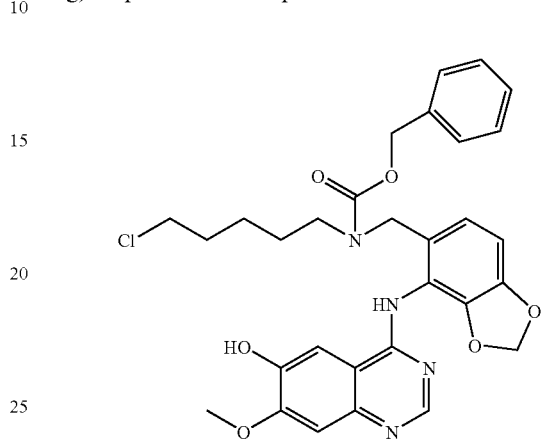

A solution of crude compound A6 (0.83 mmol) in CH₃OH (5 ml) was treated with a concentrated aqueous HCl solution (0.21 ml) and the reaction mixture was heated to 60° C. for 6 hours. The solvent was evaporated. The residue was partitioned between EtOAc and a saturated aqueous NaHCO₃ solution. The organic layer was separated, washed with water and saturated aqueous NaCl solution, then dried (Na₂SO₄), filtered and the solvent was evaporated, yielding 0.440 g (94%) of compound A7.

h) Preparation of Compound A8

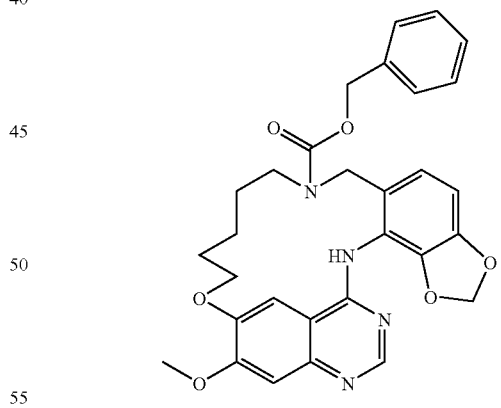

A solution of compound A7 (0.35 mmol) in DMA (10 ml) was added at 65° C. within 6 hours to a mixture of Cs₂CO₃ (0.00107 mmol) in DMA (4 ml). The reaction mixture was partitioned between EtOAc and ice/water. The organic layer was separated, washed with a saturated aqueous NaCl solution, dried (Na₂SO₄), filtered and the solvent was evaporated. The residue was purified by flash column chromatography over silica gel (SI-60 (230-400 MESH; eluent: hexane/EtOAc 100:0 to 0:100, then CH₂Cl₂/CH₃OH 100:0 to 96:4)). The product fractions were collected and the solvent was evaporated, yielding 0.167 g of compound A8.

Analytical HPLC: Method 11, Rt=3.66 (98%). APCI-MS: 543 (100, [M+H]+).

i) Preparation of Compound A9 and Compound A10

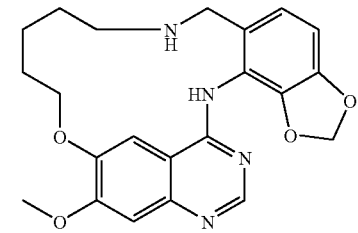

Compound A9

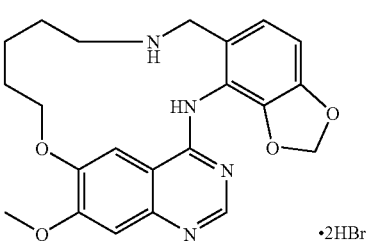

Compound A10

·2HBr

A mixture of compound A8 (0.21 mmol) and a 48% aqueous HBr solution (2 ml) was stirred for 15 minutes at 80° C. After addition of 2-propanol (1 ml), stirring was continued at 80° C. for 20 minutes. The solvents were evaporated. The residue was partitioned between EtOAc and a saturated aqueous NaHCO$_3$ solution. The organic layer was separated, washed with a saturated aqueous NaCl solution, dried (Na$_2$SO$_4$), filtered and the solvent was evaporated. The residue was purified by flash column chromatography over silica gel (eluent: CH$_2$Cl$_2$/CH$_3$OH 100:0 to 95:5). The product fractions were collected and the solvent was evaporated, yielding 0.042 g (48%, light powder) of compound A9.

Analytical HPLC: Method 1, Rt=2.94 (97%). APCI-MS: 409 (100, [M+H]+).

A suspension of compound A9 (0.05 mmol) in 2-propanol (2 ml) was treated with a 48% aqueous HBr solution (0.2 ml) and evaporated. The residue was coevaporated twice from 2-propanol. It was then was suspended in 2-propanol/Et$_2$O 1:1, filtered and dried in vacuo, yielding 0.027 g (42% overall; light powder) of compound A10 as a hydrobromide salt (0.2HBr).

Analytical HPLC: Method 2, Rt=2.70 (99%). APCI-MS: 409 (100, [M+H]+)

j) Preparation of Compound A11

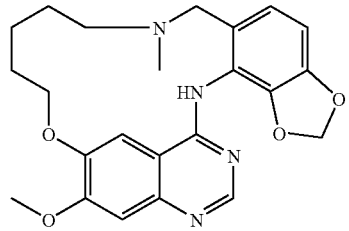 [SMILES: COc1cc2ncnc3c2cc1OCCCCCN(C)Cc1ccc2c(c1N3)OCO2]

A mixture of compound A9 (0.50 mmol), formaldehyde (0.030 g, 1.0 mmol) and NaOCH$_3$ (0.135 g, 2.5 mmol) was treated with CH$_3$OH (4 ml) and THF (2 ml). The solution was stirred for 24 hours at room temperature. NaBH$_4$ (0.038 g, 1.0 mmol) was added and stirring was continued for 5 hours. The mixture was distributed between CH$_2$Cl$_2$ and a saturated aqueous NaHCO$_3$ solution. The organic layer was separated, dried (Na$_2$SO$_4$), filtered and the solvent was evaporated, yielding 0.215 g (quantitative yield) of compound A11.

M.P.>230° C., dec. Analytical HPLC: Method 1, Rt=3.04 (95%). APCI-MS: 423 (100, [M+H]+). $^1$H-NMR (DMSO-d6): 9.44 (s, NH), 8.42 (s, 1 H), 7.22 (s, 1 H), 7.14 (s, 1 H), 6.77 (s, 2 H), 6.03 (s, 2 H), 4.42 (br. t, OCH2), 3.93 (s, OCH3), 3.41 (br. s, 2H), ca. 2.5 (2 H), 1.97 (s, NCH3), 1.77 (br. m, 4 H), 1.48 (br. m, 2 H).

k) Preparation of Compound A12

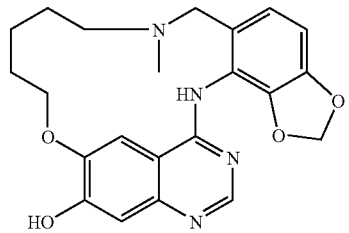 [SMILES: CN1CCCCCOc2cc3c(ncnc3cc2O)Nc2c(ccc3c2OCO3)C1]

A mixture of compound A11 (0.62 mmol), lithium chloride (6.16 mmol), sodium sulfide (Na$_2$S) nonahydrate (6.16 mmol) in DMF (5 ml) was heated in a microwave device to 150° C. for 2.5 hours. The reaction mixture was partitioned between CH$_2$Cl$_2$ and a saturated aqueous NaHCO$_3$ solution and water. The separated organic layer was dried (Na$_2$SO$_4$), filtered and the solvent evaporated. The residue was purified by flash column chromatography over silica gel (CH$_2$Cl$_2$/CH$_3$OH 100:0 to 92:8). The product fractions were collected and the solvent was evaporated. The residue (0.116 g yellow powder) was suspended in Et$_2$O, sonicated (for example in an ultrasonic bath) for 10 minutes, filtered, and dried in vacuo. A yellow powder (0.090 g) was obtained which was purified by flash column chromatography over silica gel (eluent: CH$_2$Cl$_2$/CH$_3$OH 100:0 to 92:8). The product fractions were collected and the solvent was evaporated, yielding 0.074 g (29.4%, yellow solid) of compound A12.

M.P.>230° C., dec. Analytical HPLC: Method 1, Rt=1.22 (99%). APCI-MS: 409 (100, [M+H]+). $^1$H-NMR (DMSO-d6): 10.30 (br. s, OH), 9.39 (s, NH), 8.35 (s, 1 H), 7.11 (s, 1 H), 7.08 (s, 1 H), 6.76 (s, 2 H), 6.02 (s, 2 H), 4.42 (br. t, OCH2), 3.41 (br. s, 2 H), ca. 2.5 (2 H), 1.97 (s, NCH3), 1.79 (br. m, 4 H), 1.49 (br. m, 2 H).

l) Preparation of Compound A13

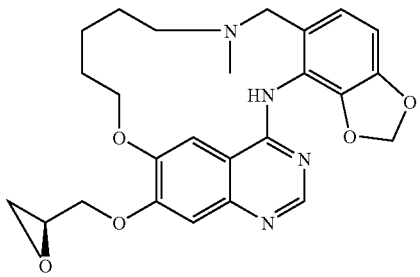 [SMILES: CN1CCCCCOc2cc3c(ncnc3cc2OC[C@@H]2CO2)Nc2c(ccc3c2OCO3)C1]

A mixture of compound A12 (0.16 mmol) and triphenylphosphine (0.24 mmol) was dried (in vacuo) and treated with THF (2 ml). (2R)-oxiranemethanol (0.17 mmol) was added. A solution of bis(1-methylethyl)ester diazenedicarboxylic acid (0.17 mmol) in THF (1.3 ml) was slowly added. The mixture was stirred at room temperature for 1½ hours, then additional triphenylphosphine (0.24 mmol), (2R)-Oxiranemethanol (0.00017 mol), and bis(1-methylethyl)ester diazenedicarboxylic acid (0.17 mol) were added. Stirring was continued for 1½ hours and the solvents were evaporated. The residue was purified by flash column chromatography over silica gel (eluent: $CH_2Cl_2/CH_3OH$ from 100:0 to 95:5). The product fractions were collected and the solvent was evaporated, yielding 0.094 g of compound A13 (S-configuration).

Example A2 a) Preparation of Compound A14

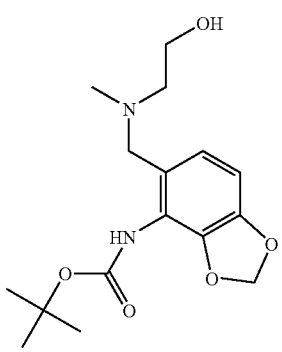 [SMILES: CN(CCO)Cc1ccc2c(c1NC(=O)OC(C)(C)C)OCO2]

To compound A1 (37.7 mmol) dissolved in 1,2-dichloroethane (160 ml) was added 2-(methylamino)ethanol (75.4 mmol) and acetic acid (17.5 mmol). The solution was stirred at room temperature for 1 hour then cooled to 0° C. NaBH(OAc)$_3$ (75.5 mmol) was added portionwise, the reaction mixture was allowed to warm to room temperature and stirring was continued for 18 hours. The mixture was partitioned between $CH_2Cl_2$ and a saturated aqueous $NaHCO_3$ solution. The organic layer was dried ($Na_2SO_4$) and the solvent was concentrated in vacuo. This afforded a white solid which was dried in vacuo, yielding 12.07 g (99%) of compound A14.

Analytical HPLC: Method 1, Rt=3.00 (10 0%). APCI-MS: 325 (100, [M+H]$^+$).

b) Preparation of Compound A15

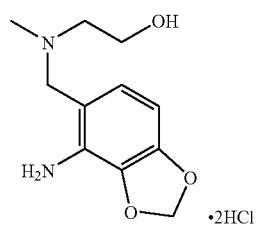 [SMILES: CN(CCO)Cc1ccc2c(c1N)OCO2 ; "·2HCl"]

At 0° C., a HCl solution (4M in dioxane) (7.5 ml) was added to a solution of compound A14 (1.54 mmol) in dry $CH_2Cl_2$ (5 ml). The mixture was stirred for one hour at 0° C., then for one hour at room temperature. The solvents were evaporated and the residue was treated with $Et_2O$ (10 ml), sonicated for 10 minutes, stirred for 30 minutes, and filtered. The solid was dried in vacuo, yielding 460 mg (quantitative, white powder) of compound A15 as a hydrochloride salt (0.2HCl).

Analytical HPLC: Method 1, Rt=1.72 (96%). APCI-MS: 225 ([M+H]$^+$), 150 (100).

c) Preparation of Compound A16

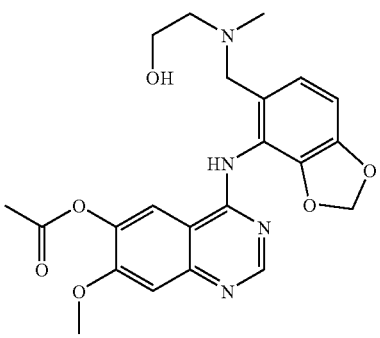 [SMILES: COc1cc2ncnc(Nc3c(CN(C)CCO)ccc4c3OCO4)c2cc1OC(C)=O]

Under an inert atmosphere, compound A15 (21.9 mmol) and 4-chloro-7-methoxy-6-quinazolinol acetate (ester) (22.0 mmol) were suspended in dry acetonitrile (170 ml) and heated to reflux for 90 minutes (after 60 minutes a clear, orange solution occurred). The solution was cooled and poured onto a mixture of $CH_2Cl_2$ and a sat. aq. $NaHCO_3$ solution. The organic phase was separated, the aqueous phase extracted with $CH_2Cl_2$. The organic phases were washed (sat. aq. NaCl soln.), dried ($Na_2SO_4$), filtered, and concentrated. The crude product was evaporated from $CH_2Cl_2$ and treated with $Et_2O$/hexane 1:1 (100 ml), sonicated and stirred to give a fine solid which was filtered and dried in vacuo, yielding 9.6 g (99%) of compound A16.

Analytical HPLC: Method 1, Rt=2.76 (92%). APCI-MS: 441 (100, [M+H]$^+$).

d) Preparation of Compound A17

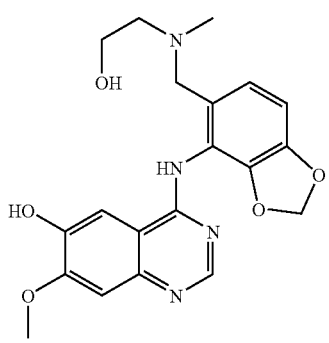 [SMILES: COc1cc2ncnc(Nc3c(CN(C)CCO)ccc4c3OCO4)c2cc1O]

A 32% aqueous HCl solution (3 ml) was slowly added to a suspension of compound A16 (4.54 mmol) in $CH_3OH$ (30 ml). The resulting brown solution was stirred for 2.5 hours at 65° C. The mixture was partitioned between $CH_2Cl_2$ and a saturated aqueous $NaHCO_3$ solution. The organic layer was dried ($Na_2SO_4$) and the solvent was concentrated in vacuo, yielding 1.62 g (89.5%, colourless powder) of compound A17.

Analytical HPLC: Method 1, Rt=2.56 (95%). APCI-MS: 399 (100, [M+H]$^+$).

e) Preparation of Compound A18

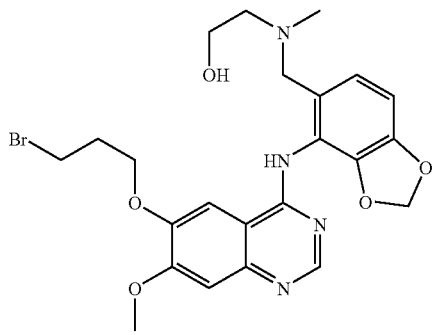 [SMILES: COc1cc2ncnc(Nc3c(CN(C)CCO)ccc4c3OCO4)c2cc1OCCCBr]

A mixture of compound A17 (4.84 mmol) and K$_2$CO$_3$ (9.69 mmol) was dried in vacuo for one hour, then dissolved in dry DMF (37 ml) and stirred at room temperature for one hour. 1,3-Dibromopropane (9.69 mmol) was added dropwise within 5 minutes and stirring of the mixture was continued for 15 hours. The mixture was partitioned between EtOAc and a half-saturated aqueous NaHCO$_3$ solution. The organic layer was dried (Na$_2$SO$_4$) and the solvent was concentrated in vacuo. The obtained residue was partitioned between water and a saturated aqueous NaCl solution. The organic layer was dried (Na$_2$SO$_4$) and the solvent was concentrated in vacuo, followed by purification by flash column chromatography over silica gel Si-60 (230-400 mesh) (eluent: CH$_2$Cl$_2$/CH$_3$OH 97:3 then CH$_2$Cl$_2$/CH$_3$OH 97:3 with 0.5% saturated aqueous NH$_3$ solution to CH$_2$Cl$_2$/CH$_3$OH 95:5 with 0.5% saturated aqueous NH$_3$ solution), yielding 1.12 g (44.4%, yellow foam) of compound A18.

Analytical HPLC: Method 2, Rt=2.91 (86%). APCI-MS: 519/521 (100, [M+H]$^+$).

f) Preparation of Compound A19

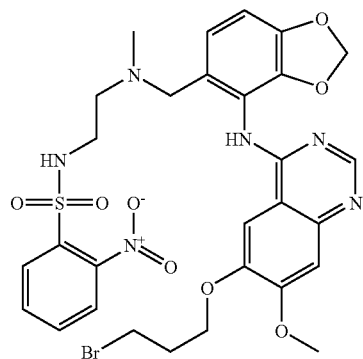 [SMILES: COc1cc2ncnc(Nc3c(CN(C)CCNS(=O)(=O)c4ccccc4[N+](=O)[O-])ccc4c3OCO4)c2cc1OCCCBr]

A mixture of compound A18 (2.0 mmol), 2-nitrobenzenesulfonamide (6.0 mmol), and triphenylphosphine (6.2 mmol) was dried in vacuo for 15 minutes and dissolved under an inert atmosphere in dry THF (20 ml). DIAD (6.0 mmol) was added dropwise. The solution was stirred for 2 hours at room temperature. A precipitate was formed. The solvents were evaporated and the residue was purified by flash column chromatography over silica gel (Si-60 (230-400 mesh) (eluent: EtOAc, CH$_2$Cl$_2$/CH$_3$OH 100:0 to 96:4)). The product fractions were collected and the solvent was evaporated, yielding 1.02 g (72.6%, yellow foam) of compound A19.

Analytical HPLC: Method 2, Rt=3.33 (79%). APCI-MS: 703/705 (100, [M+H]$^+$).

g) Preparation of Compound A20

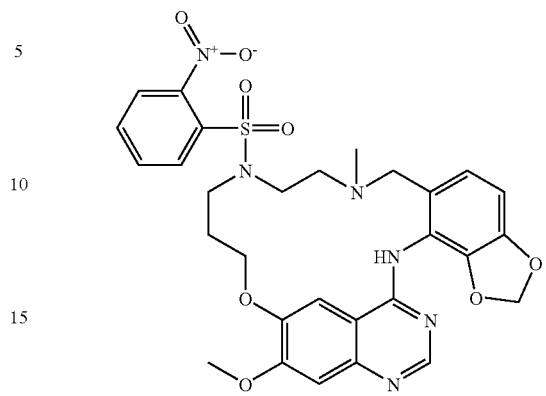

A mixture of Cs$_2$CO$_3$ (6.8 mmol) and tetrabutylammonium iodide (2.8 mmol) was dried in vacuo for 15 minutes and under an inert atmosphere was treated with dry acetonitrile (105 ml). A solution of compound A19 (1.4 mmol) in acetonitrile (20 ml) was added dropwise over 10 minutes. The mixture was stirred for 15 hours and concentrated. The concentrate was partitioned between EtOAc and water. The organic layer was dried (Na$_2$SO$_4$) and the solvent was concentrated in vacuo. The crude product was purified by flash column chromatography over silica gel (Si-60 (230-400 mesh) (eluent: CH$_2$Cl$_2$/CH$_3$OH 100:0 to 95:5)) to afford the product, still contaminated with some tetrabutylammonium iodide. The material was dissolved in EtOAc and washed with water twice, yielding 0.62 g (72.7%, light powder) of compound A20.

Analytical HPLC: Method 2, Rt=3.32 (93%). APCI-MS: 623 (100, [M+H]$^+$).

h) Preparation of Compound A21 and A22

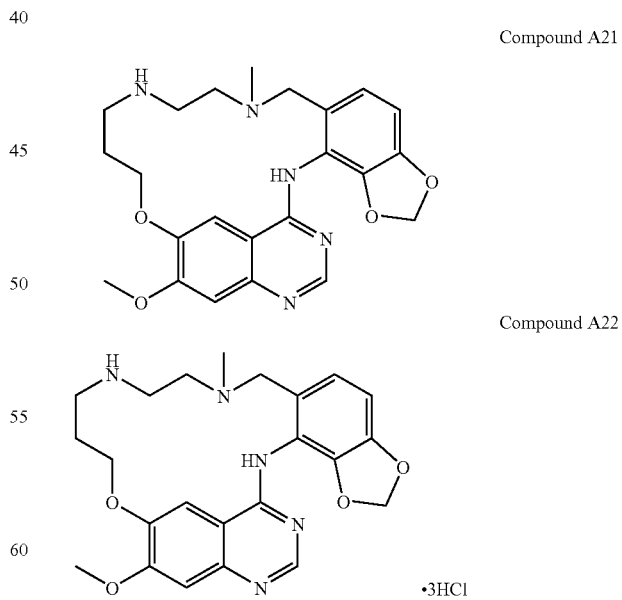

A mixture of Cs$_2$CO$_3$ (2.7 mmol) and compound A20 (0.9 mmol) was treated with dry DMF (35 ml). Thiophenol (1.1 mmol) was added and the mixture was stirred at room temperature for 15 hours. The concentrate was partitioned between EtOAc and water. The organic layer was separated, dried (Na$_2$SO$_4$), filtered and concentrated. Purification by flash column chromatography over silica gel (Si-60 (230-400 mesh) (eluent: CH$_2$Cl$_2$/CH$_3$OH 100:0 to 95:5)), yielded 365 mg (91.7%) of compound A21.

Analytical HPLC: Method 2, Rt=2.67 (99%). APCI-MS: 438 (100, [M+H]$^+$). $^1$H-NMR (DMSO-d6): 10.52 (br. s, NH), 8.43 (s, 1 H), 8.17 (s, 1 H), 7.18 (s, 1 H), 6.75 (d, J=7.9, 1 H), 6.69 (d, J=7.8, 1 H), 5.96 (s, 2 H), 4.45 (br. t, OCH2), 3.92 (s, OCH3), 3.58 (br. s, 2H), 2.69 (br. s, 2 H), 2.52 (br. s, 2 H), 2.39 (br. s, 2 H), 2.25 (s, NCH3), 1.80 (br. m, 3 H).

A sample of compound A21 (0.16 mmol) was taken up in 2-propanol (3 ml) treated with ca. 0.2 ml 32% aqueous HCl solution and the solvent was evaporated. This treatment was repeated twice. The residue was then coevaporated twice from 2-propanol (2 ml) and Et$_2$O (2 ml). It was then suspended in Et$_2$O and filtered. The solid was washed (Et$_2$O/hexane 1:1) and dried i.v to give 75 mg (86.2%) of compound A22 as a hydrochloride salt (0.3HCl).

Analytical HPLC: Method 2, Rt=2.69 (100%). APCI-MS: 438 (100, [M+H]$^+$).

i) Preparation of Compound A23

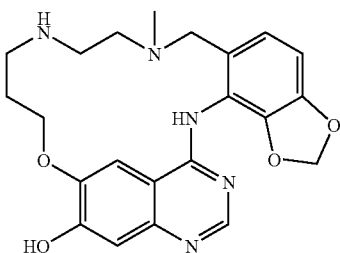 [SMILES: CN1CCNCCCOc2cc3c(ncnc3cc2O)Nc2c(ccc3c2OCO3)C1]

A mixture of compound A21 (0.571 mmol), lithium chloride (5.71 mmol) and sodium sulfide (Na$_2$S) nonahydrate (5.7 mmol) was treated with DMF (5 ml) and heated in a microwave device to 150° C. for 15 minutes. The residue was partitioned between EtOAc, CH$_2$Cl$_2$, and a saturated aqueous NaHCO$_3$ solution. The separated organic layer was dried (Na$_2$SO$_4$), filtered and the solvent evaporated. The residue was purified by flash column chromatography over silica gel (eluent: CH$_2$Cl$_2$/CH$_3$OH 100:0 to 90:10, then CH$_2$Cl$_2$/CH$_3$OH 90:10 with 1% conc. aq. NH$_3$ soln.). The product fractions were collected and the solvent was evaporated, yielding 0.142 g (58%, yellow solid) of compound A23.

j) Preparation of Compound A24 and A25

Compound A24

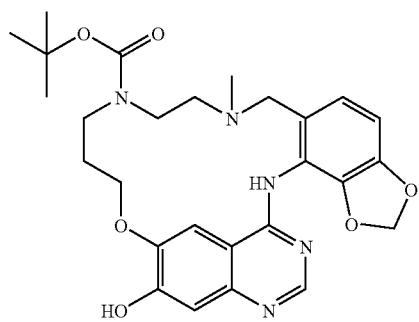

Compound A25

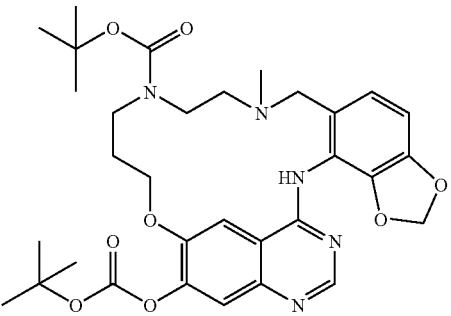

A solution of compound A23 (1.44 mmol) in dry THF (17 ml) was treated with Et$_3$N (1.58 mmol). A precipitate occurred. Additional dry THF (5 ml) was added. A solution of Boc-anhydride (1.58 mmol) in dry THF (8 ml) was added dropwise at 0° C. The mixture was stirred at 0° C. for 30 minutes, then at room temperature for 1 hour. Additional Boc-anhydride (63 mg) was added and stirring was continued for 1 hour. The concentrate was partitioned between EtOAc and a saturated aqueous NaHCO$_3$ solution. The organic layer was dried (Na$_2$SO$_4$) and the solvent was concentrated in vacuo. Purification by flash column chromatography over silica gel (Si-60 (230-400 mesh) (eluent: CH$_2$Cl$_2$/CH$_3$OH 100:0 to 95:5)), yielded 498 mg (66%; yellow foam) of compound A24 and 144 mg (16%; yellow powder) of compound A25.

Compound A24: Analytical HPLC: Method 2, Rt=2.98 (99%). APCI-MS: 524 (100, [M+H]$^+$).

Compound A25: Analytical HPLC: Method 2, Rt=3.93 (100%). APCI-MS: 624 (100, [M+H]$^+$).

k) Preparation of Compound A26

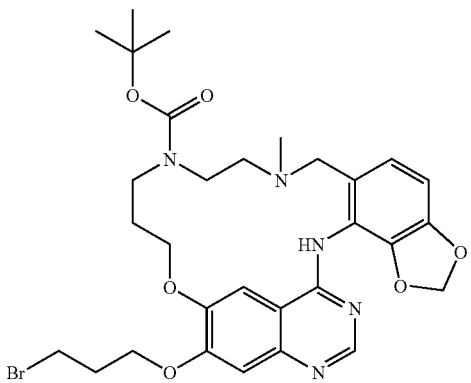 [SMILES: CN1CCN(C(=O)OC(C)(C)C)CCCOc2cc3c(ncnc3cc2OCCCBr)Nc2c(ccc3c2OCO3)C1]

A mixture of compound A24 (0.15 mmol) and triphenylphosphine (0.31 mmol) was dried in vacuo for 30 minutes. Under an inert atmosphere, dry THF (3 ml) and 3-bromo-1-propanol (0.24 mmol) were added. A solution of DIAD (0.24 mmol) in THF (1 ml) was added dropwise. The solution was stirred at room temperature for 2 hours and the solvents were evaporated, yielding compound A26.

l) Preparation of Compound A27

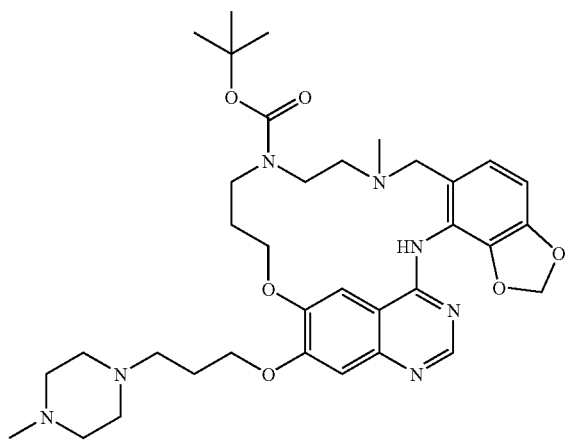 [SMILES: CN1CCN(CCCOc2cc3ncnc4c3cc2OCCCN(C(=O)OC(C)(C)C)CCN(C)Cc2ccc3c(c2N4)OCO3)CC1]

Compound A26 (0.124 mmol) was dissolved in dry acetonitrile (4 ml). 1-Methylpiperazine (4.47 mmol) was added and the reaction mixture was stirred overnight at ambient temperature. The mixture was treated with a saturated aqueous $NaHCO_3$ solution, then extracted twice with $CHCl_3$. The organic layer was washed with a saturated aqueous $NaHCO_3$ solution, dried ($Na_2SO_4$), filtered and the solvent was evaporated. The residue was purified by column chromatography over silica gel (eluent: $CH_2Cl_2/CH_3OH$ from 100/0 to 90/10 to $CH_2Cl_2/(CH_3OH/1\% NH_3)$ 90/10). The product fractions were collected and the solvent was evaporated, yielding 0.075 g (yellow foam; 91.5% yield over two steps) of compound A27.

Example A3 a) Preparation of Compound A28

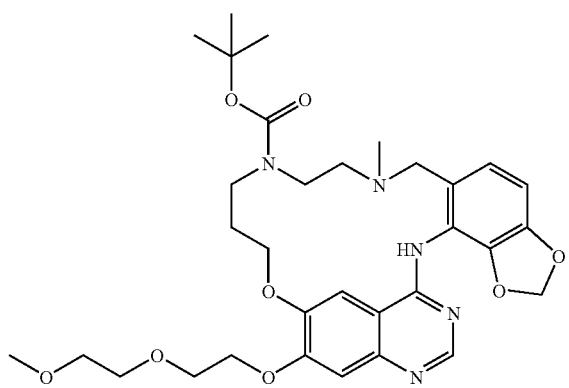 [SMILES: COCCOCCOc1cc2ncnc3c2cc1OCCCN(C(=O)OC(C)(C)C)CCN(C)Cc1ccc2c(c1N3)OCO2]

Compound A24 (0.115 mmol) and triphenylphosphine (0.241 mmol) were combined and dried for 30 minutes using a vacuum pump. Dry THF (2 ml) was added, followed by 2-(2-methoxyethoxy)ethanol (0.183 mmol). A solution of DIAD (0.183 mmol) in dry THF (1 ml) was added dropwise. The resultant reaction solution was stirred for 2 hours at room temperature. The solvent was evaporated. The residue was purified by column chromatography over silica gel (eluent: $CH_2Cl_2/CH_3OH$ from 100/0 to 96/4), yielding 0.062 g (86%, beige foam) of compound A28.

Example A4 a) Preparation of Compound A29

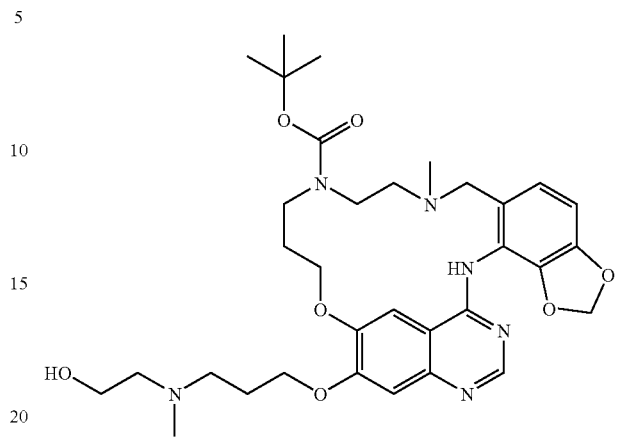

Compound A26 (0.124 mmol), 2-(methylamino)ethanol (4.47 mmol) and dry acetonitrile (4 ml) were introduced into a sealed tube. The reaction mixture was heated to 60° C., then stirred overnight at 60° C. The reaction mixture was cooled, then taken up in $CHCl_3$ and washed twice with a saturated aqueous $NaHCO_3$ solution. The separated organic layer was dried ($Na_2SO_4$), filtered and the solvent evaporated. The residue was purified by column chromatography over silica gel (eluent: $CH_2Cl_2/CH_3OH$ from 100/0 to 90/10 to $CH_2Cl_2/$ $(CH_3OH/1\% NH_3)$ 90/10), yielding 0.069 g of compound A29.

Example A5 a) Preparation of Compound A30

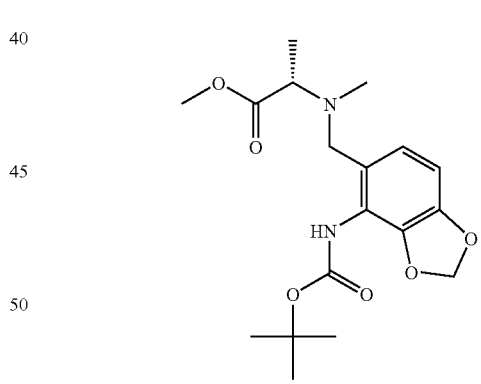

To a suspension of N-methyl-L-alanine methyl ester (45.2 mmol) in THF (240 ml) was added DIPEA (90.5 mmol), compound A1 (30.1 mmol) and $NaBH(OAc)_3$ (60.3 mmol) portionwise. The reaction mixture was stirred at room temperature overnight, diluted with a saturated aqueous $NaHCO_3$ solution and extracted with EtOAc. The combined organic extracts were washed with brine, dried ($Na_2SO_4$), filtered and concentrated under reduced pressure. The residue was purified by silica gel chromatography (eluent: hexanes/EtOAc 2:1), yielding 9.5 g (86%) of compound A30 (S-configuration) as a white solid.

Analytical HPLC: Method 1, Rt=3.47 (100%). APCI-MS: 367 (100, $[M+H]^+$).

b) Preparation of Compound A31

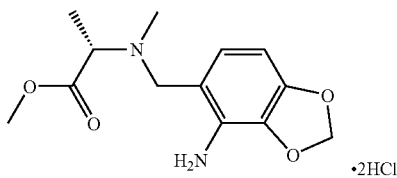 [SMILES: COC(=O)[C@H](C)N(C)Cc1ccc2c(c1N)OCO2 ; "·2HCl"]

To a solution of compound A30 (8.22 mmol) in anhydrous CH$_2$Cl$_2$ (30 ml) at 0° C. was added a HCl solution (4M in dioxane) (48 ml). After 1.5 hours, the reaction mixture was concentrated under reduced pressure. The residue was taken up in Et$_2$O, filtered and washed with Et$_2$O. The solid was then collected and dried in vacuum, yielding 3.62 g (quantitative, containing dioxane) of compound A31 (S-configuration, light powder) as a hydrochloride salt (0.2HCl).

Analytical HPLC: Method 1, Rt=3.02 (98%).

c) Preparation of Compound A32

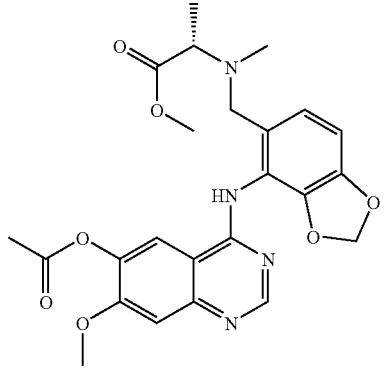 [SMILES: COC(=O)[C@H](C)N(C)Cc1ccc2c(c1Nc1ncnc3cc(OC)c(OC(C)=O)cc13)OCO2]

Compound A31 (1.36 mmol) and 6-acetoxy-4-chloro-7-methoxy quinazoline (1.36 mmol) were dried in vacuum for 15 minutes. Acetonitrile (15 ml) was added. The reaction mixture was heated to reflux for 40 minutes, then allowed to cool to room temperature, diluted with a saturated aqueous NaHCO$_3$ solution and extracted with EtOAc. The combined organic extracts were dried (Na$_2$SO$_4$), filtered, concentrated under reduced pressure and purified by silica gel chromatography (eluent: EtOAc). The product fractions were collected and the solvent was evaporated, yielding 0.498 g (61%; white foam; S-configuration) of compound A32.

Analytical HPLC: Method 1, Rt=3.02 (95%). APCI-MS: 483 (100, [M+H]$^+$).

d) Preparation of Compound A33

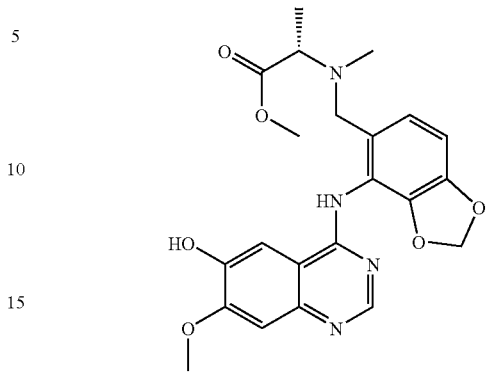

To a solution of compound A32 (11.0 mmol) in CH$_3$OH (55 ml) was added a 32% HCl solution. (10.4 ml). The reaction mixture was stirred at 50° C. for 3 hours and then concentrated under reduced pressure. The residue was taken up with a saturated aqueous NaHCO$_3$ solution and extracted with EtOAc. The combined organic extracts were washed with water, brine, dried (Na$_2$SO$_4$), filtered and concentrated under reduced pressure, yielding 5.04 g (quantitative yield; S-configuration) of compound A33 as a light foam, which was used without further purification.

Analytical HPLC: Method 1, Rt=2.79 (99%). APCI-MS: 441 (100, [M+H]$^+$).

e) Preparation of Compound A34

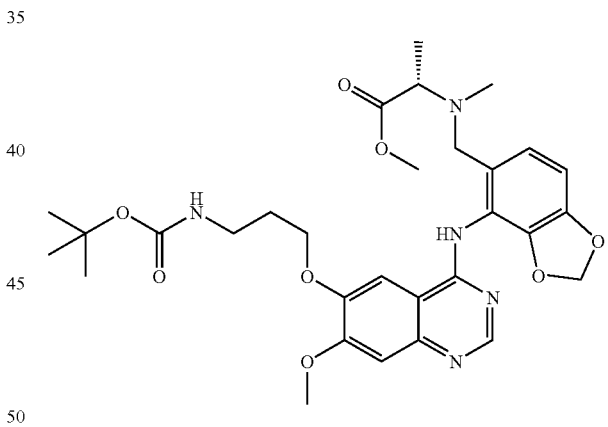

To a solution of compound A33 (10.4 mmol) in dry DMF (95 ml) was added anhydrous K$_2$CO$_3$ (15.5 mmol). The reaction mixture was stirred at room temperature for 15 minutes. Tert-butyl (3-bromopropyl)carbamate (11.4 mmol) was then added. The reaction mixture was then stirred at 50° C. After 6 hours, additional tert-butyl (3-bromopropyl)carbamate (0.5 g, 2.10 mmol) was added. After 5 hours the mixture was filtered. The residue was rinsed with EtOAc. The filtrate was washed with water, brine, dried over Na$_2$SO$_4$, filtered, concentrated under reduced pressure, and the residue was purified by silica gel chromatography (eluent: CH$_2$Cl$_2$/CH$_3$OH 100:0 to 95:5), yielding 4.549 g (80%; S-configuration) of compound A34 as a colourless foam.

Analytical HPLC: Method 1, Rt=3.41 (100%). APCI-MS: 599 (100, [M+H]$^+$).

f) Preparation of Compound A35

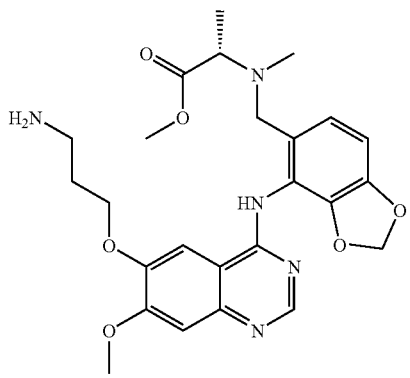 [SMILES: COC(=O)[C@H](C)N(C)Cc1ccc2c(c1Nc1ncnc3cc(OC)c(OCCCN)cc13)OCO2]

To a solution of compound A34 (300 mg, 0.50 mmol) in anhydrous $CH_2Cl_2$ (10 ml) at 0° C. was added trifluoroacetic acid (10 ml, 0.13 mol). After 1 hour, the reaction mixture was concentrated under reduced pressure. The residual trifluoroacetic acid was removed by coevaporation with $CH_2Cl_2$. The residue was taken up in water, made alkaline to pH 8-9 by addition of saturated aqueous $NaHCO_3$ solution, extracted several times with EtOAc then $CH_2Cl_2$. The combined organic extracts were dried ($Na_2SO_4$), filtered and concentrated under reduced pressure, yielding 0.293 g (quantitative yield; S-configuration; used in next reaction step, without further purification) of compound A35.

Analytical HPLC: Method 1, Rt=2.69 (97%). APCI-MS: 498 (100, $[M+H]^+$).

g) Preparation of Compound A36

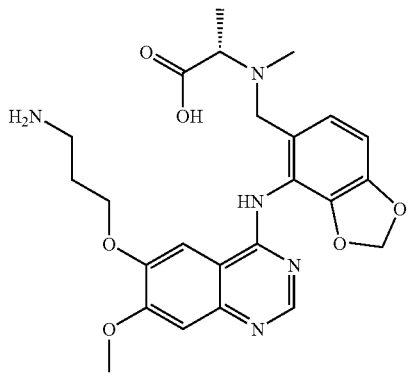 [SMILES: COc1cc2ncnc(Nc3c(CN(C)[C@@H](C)C(=O)O)ccc4c3OCO4)c2cc1OCCCN]

Compound A35 as a trifluoroacetic acid salt (1.67 mmol) was dissolved in a mixture of $CH_3OH$ (15 ml) and water (1.5 ml). The solution was cooled to 0° C. An aqueous lithium hydroxide solution (1.0 M) (17 mmol) was added and the mixture was allowed to warm to room temperature while stirring. The reaction mixture was stirred for 26 hours, then concentrated to half its initial volume and a few drops of $NaH_2PO_4$ were added until pH=8. The layers were separated. The aqueous phase was extracted with $CH_2Cl_2/CH_3OH$ 95/5 (16×100 ml). The combined organic layers were dried ($Na_2SO_4$), filtered and the solvent was evaporated, yielding 0.950 g (quantitative yield; S-configuration; used in next reaction step, without further purification) of compound A36.

Analytical HPLC: Method 1, Rt=2.64 (100%). APCI-MS: 484 (100, $[M+H]^+$).

h) Preparation of Compound A37 and A38

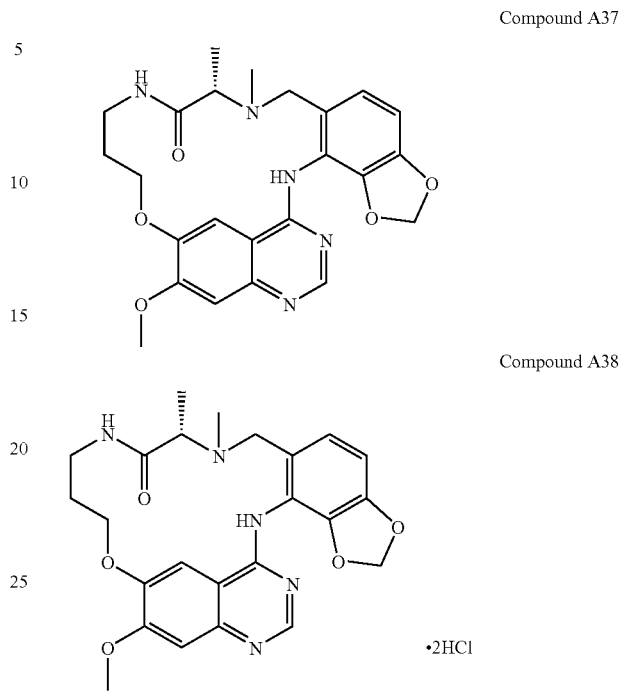

Compound A37

Compound A38

·2HCl

To a solution of crude compound A36 (0.21 mmol) in anhydrous DMF (20 ml) was added a solution of HBTU (0.62 mmol) and DIPEA (1.05 mmol) in anhydrous DMF (20 ml), over a 5.5 hour period time, via a syringe pump. The reaction mixture was then further stirred for 10 hours and concentrated under reduced pressure. The residue was taken up in $CH_3OH$ and filtered. The filtrate was concentrated under reduced pressure and purified by silica gel chromatography ($CHCl_3$/$CH_3OH$ 100:0 to 99:1) yielding 47 mg (49%; S-configuration) of compound A37.

Analytical HPLC: Method 1, Rt=2.90 (100%). APCI-MS: 466 (100, $[M+H]^+$). $^1$H-NMR (CDCl3): d 8.58 (s, 1H), 7.17 (s, 1H), 7.14 (br. s, 1H), 6.78 (br. s, 1H), 6.69 (d, J=7.8, 1 H), 6.61 (d, J=7.8, 1 H), 5.97 (d, J=3.3, 2 H), 4.33 (br. s, 2H), 3.94 (s, OCH3), 3.67 (br. s, 2H), 3.47 (br. s, 3H), 2.18 (s, NCH3), 2.09 (m, 2H), 1.25 (d, J=6.6, 3 H).

Compound A37 was converted into the HCl salt by treatment with 2-propanol (8 ml) and a conc. aq. HCl solution (0.1 ml), yielding 36 mg of compound A38 (S-configuration) as a hydrochloride salt (0.2HCl).

Analytical HPLC: Method 1, Rt=2.87 (100%). APCI-MS: 466 (100, $[M+H]^+$).

i) Preparation of Compound A39 and A40

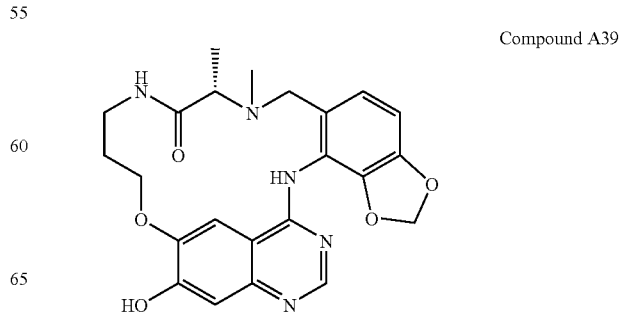

Compound A39 k) Preparation of Compound A42

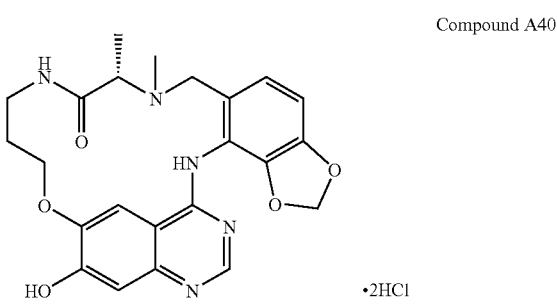

Compound A40 ·2HCl

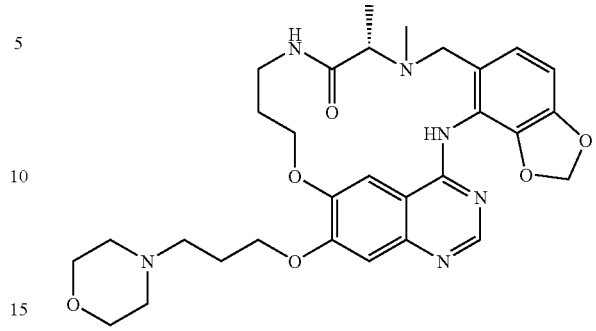

In a vial was introduced sodium sulfide (Na₂S) nonahydrate (2.68 mmol), compound A37 (0.27 mmol), lithium chloride (2.67 mmol) and anhydrous DMF (2.2 ml). The vial was then sealed, set into a microwave device and stirred at 150° C. for 15 minutes. After cooling to room temperature, the reaction mixture was diluted with a saturated aqueous NaHCO₃ solution and extracted with EtOAc. The combined organic extracts were dried (Na₂SO₄), filtered, concentrated under reduced pressure and purified by silica gel chromatography (eluent: CHCl₃/hexanes/CH₃OH from 5:5:0 to 5:5:1) yielding 40 mg (33%, S-configuration) of compound A39.

Compound A39 (35 mg) was converted into the HCl salt by treatment with 2-propanol and conc. aq. HCl solution (0.1 ml), yielding 33 mg (S-configuration) of compound A40 as a hydrochloride salt (0.2HCl)

Analytical HPLC: Method 1, Rt=2.78 (100%). APCI-MS: 452 (100, [M+H]⁺).

j) Preparation of Compound A41

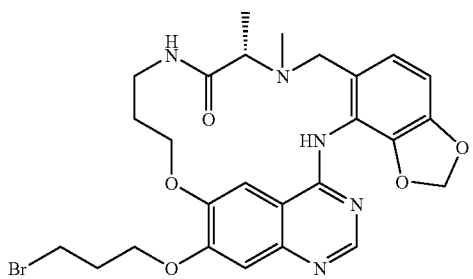 [SMILES: C[C@H]1C(=O)NCCCOc2cc3c(ncnc3cc2OCCCBr)Nc2c(ccc3c2OCO3)CN1C]

A mixture of compound A39 (0.22 mmol) and triphenylphosphine (0.46 mmol) were dried in vacuum for 30 minutes and dissolved in dry THF (2 ml). 3-Bromo-1-propanol (31 ml, 0.35 mmol) was added. A solution of DIPEA (0.35 mmol) in THF (2 ml) was slowly added. The mixture was stirred for 2 hours at room temperature and the solvent was evaporated. The residue was filtered through silica gel (eluent: CH₂Cl₂/CH₃OH 100:0 to 93:7). The product fractions were collected and the solvent was evaporated, yielding compound A41 (S-configuration) as impure compound which was used without any further purification.

To a suspension of crude compound A41 (0.22 mmol) in anhydrous, dry acetonitrile (7 ml) was added morpholine (7.29 mmol). The reaction mixture was stirred at room temperature for 89 hours, then diluted with a saturated aqueous NaHCO₃ solution and extracted with EtOAc. The combined organic extracts were dried (Na₂SO₄), filtered, concentrated under reduced pressure. The residue was purified by silica gel chromatography (CH₂Cl₂/CH₃OH from 10:0 to 9:1). The product fractions were collected and the solvent was evaporated, yielding 0.115 g (90% over the two steps; S-configuration; off-white foam) of compound A42.

Analytical HPLC: Method 1, Rt=2.60 (96%). APCI-MS: 579 (100, [M+H]⁺).

Example A6 a) Preparation of Compound A43

Compound A39 (0.177 mmol) and triphenylphosphine (0.372 mmol) were combined, then dried using a vacuum pump. Under an inert atmosphere, dry THF (2 ml) was added. The suspension was stirred. 2-(2-Methoxyethoxy)ethanol (0.283 mmol) was added. A solution of DIPEA (0.283 mmol) in dry THF (1 ml) was added dropwise. The resultant reaction solution was stirred for 2.5 hours at room temperature. The solvent was evaporated, then dried in vacuo for one hour. The residue (0.300 g) was purified by flash column chromatography over silica gel (eluent: CH₂Cl₂/CH₃OH from 100:0, over 99:1, 98:2, 97:3 to 95:5). The product fractions were collected and the solvent was evaporated, yielding 0.074 g (76%; S-configuration) of compound A43.

Example A7 a) Preparation of Compound A44

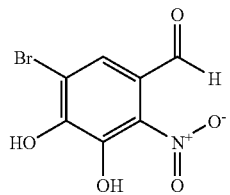

To a suspension of anhydrous AlCl₃ (9.45 mmol) in anhydrous, dry CH₂Cl₂ (5 ml), was added portionwise 5-bromo-4-hydroxy-3-methoxy-2-nitrobenzaldehyde (3.62 mmol). The reaction mixture was cooled to 0° C. and pyridine (15.9 mmol) was added dropwise. The reaction mixture was then allowed to warm to room temperature, stirred overnight, poured into a mixture of water (50 ml) and concentrated aqueous HCl solution (3.9 ml), stirred at 55° C. for one hour and cooled again to 0° C. The precipitate was filtered, washed with water, collected, and dried in vacuo, yielding 0.755 g (79%, as a yellow powder) of compound A44.

Analytical HPLC: Method 2, Rt=3.56 (98%). ¹H-NMR (DMSO-d6): ca 10.0 (very br s, OH), 9.68 (s, CHO), 7.80 (s, 1 H).

b) Preparation of Compound A45

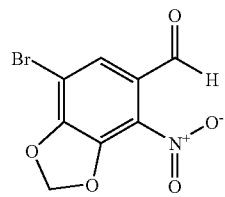 [SMILES: O=Cc1cc(Br)c2c(c1[N+](=O)[O-])OCO2]

To a solution of compound A44 in anhydrous DMF (10 ml) was added diiodomethane (3.81 mmol). Sodium hydride (55% in mineral oil, 4.0 mmol) was added portionwise. The reaction mixture was heated to 80° C. and stirred overnight. After cooling to room temperature, the reaction mixture was diluted with an aqueous 1 M HCl solution and extracted with EtOAc. The combined organic extracts were dried (Na₂SO₄), filtered, concentrated under reduced pressure. The residue was purified by silica gel chromatography (eluent: EtOAc/hexanes 0:100 to 30:70). The product fractions were collected and the solvent was evaporated, yielding 0.097 g (19%, as an orange powder) of compound A45.

Analytical HPLC: Method 10, Rt=3.35 (90%). APCI-MS 273/275 (100, [M+H]). ¹H-NMR (DMSO-d6): 9.98 (s, CHO), 7.79 (s, 1 H), 6.54 (s, 2 H).

c) Preparation of Compound A46

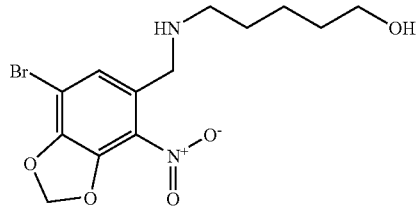 [SMILES: O=[N+]([O-])c1c(CNCCCCCO)cc(Br)c2c1OCO2]

5-Amino-1-pentanol (2.81 mmol) was added to a solution of compound A45 (1.36 mmol) in 1,2-dichloroethane (14.4 ml). The mixture was stirred for 15 minutes and cooled to 0° C. Glacial acetic acid (2.8 mmol) was added in one portion and NaBH(OAc)₃ (2.73 mmol) was added portionwise. The mixture was stirred at room temperature for 6 hours. The residue was partitioned between CH₂Cl₂ and a saturated aqueous NaHCO₃ solution. The organic layer was separated, washed with a saturated aqueous NaHCO₃ solution, dried (Na₂SO₄), filtered and the solvent was evaporated under reduced pressure, yielding 0.490 g (quantitative yield; used in next reaction step, without further purification) of compound A46.

d) Preparation of Compound A47

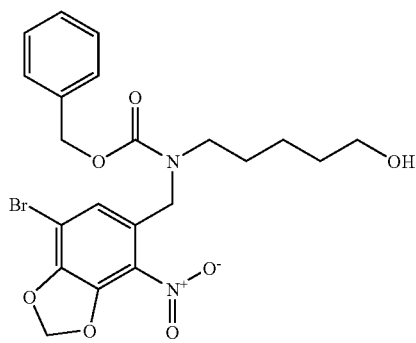 [SMILES: O=C(OCc1ccccc1)N(CCCCCO)Cc1cc(Br)c2c(c1[N+](=O)[O-])OCO2]

To a solution of the crude amine compound A46 (1.36 mmol) in anhydrous anhydrous CH₂Cl₂ (19 ml) at 0° C. was added portionwise 1-[[(phenylmethoxy)carbonyl]oxy]-2,5-pyrrolidinedione (1.88 mmol). The reaction mixture was allowed to warm to room temperature, stirred for 4 hours, diluted with CH₂Cl₂, washed with water, dried (Na₂SO₄), filtered, and concentrated under reduced pressure. The crude product was purified by silica gel chromatography (eluent: EtOAc/hexanes 1:1 then 6:4). The product fractions were collected and the solvent was evaporated, yielding 0.500 g (74%) of compound A47.

Analytical HPLC: Method 10, Rt=4.49 (96%). APCI-MS 495/497 (100, [M+H]⁺)

e) Preparation of Compound A48

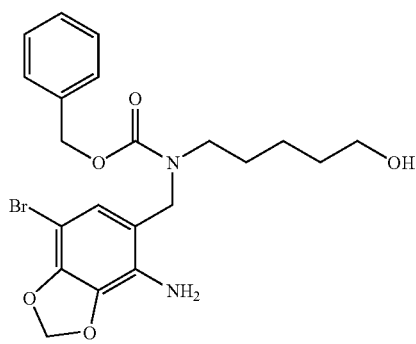 [SMILES: Nc1c(CN(CCCCCO)C(=O)OCc2ccccc2)cc(Br)c2c1OCO2]

A solution of compound A47 (0.1 mmol) in THF (1.4 ml, containing 0.1 mol equivalent of Et₃N) was hydrogenated for 2 hours in the presence of a solution of thiophene (4% in DIPE, 0.050 ml), vanadium (V) oxide (5.7 mg) and Pt/C (5%) (50 mg). The reaction mixture was then filtered through Celite. The filter residue was rinsed with CH₂Cl₂. The filtrate was concentrated under reduced pressure, yielding 0.045 g (97%, used directly without any further purification) of compound A48. APCI-MS 465/467 (100, [M+H]$^+$) (measured according to the MS method described in general procedure C from the part 'compound identification')

f) Preparation of Compound A49

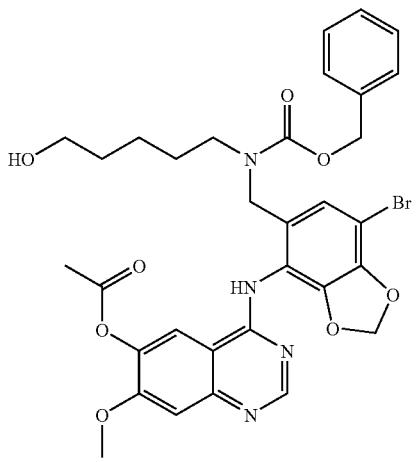 [SMILES: COc1cc2ncnc(Nc3c(CN(CCCCCO)C(=O)OCc4ccccc4)cc(Br)c4c3OCO4)c2cc1OC(C)=O]

To a solution of compound A48 (1.05 mmol) in 2-propanol (10.7 ml) was added 4-chloro-7-methoxy-6-quinazolinol acetate (ester) (1.26 mmol). The reaction mixture was heated to reflux. After 3 and 4 hours, additional 4-chloro-7-methoxy-6-quinazolinol acetate (ester) (53 mg and 80 mg, respectively) was added. After 5 hours, the mixture was allowed to cool to room temperature and concentrated under reduced pressure. The crude product was purified by silica gel chromatography (eluent: CH$_2$Cl$_2$/CH$_3$OH 100:0 to 98:2). The product fractions were collected and the solvent was evaporated, yielding 0.492 g (69%) of compound A49.

Analytical HPLC: Method 10, Rt=3.56 (92%). APCI-MS 681/683 (100, [M+H]$^+$).

g) Preparation of Compound A50

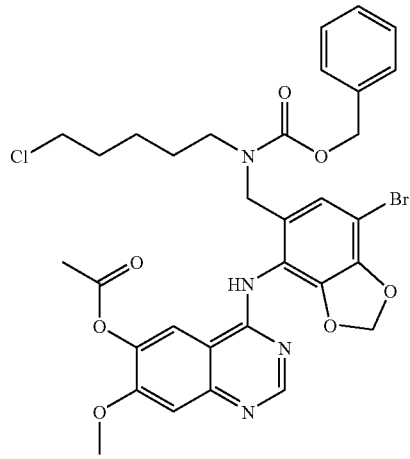 [SMILES: COc1cc2ncnc(Nc3c(CN(CCCCCCl)C(=O)OCc4ccccc4)cc(Br)c4c3OCO4)c2cc1OC(C)=O]

To a solution of compound A49 (0.44 mmol) in anhydrous DMA (4 ml) was added methanesulfonyl chloride (2.46 mmol). The reaction mixture was placed into a preheated oil bath at 95° C. and stirred for 3.5 hours. After cooling to ambient temperature, the reaction mixture was diluted with EtOAc, washed with saturated aqueous NaHCO$_3$ solution, water, brine, dried (Na$_2$SO$_4$), filtered and concentrated under reduced pressure, yielding 0.319 g (quantitative yield, which was used directly for the next step.) of compound A50.

APCI-MS 699/701/703 (100, [M+H]$^+$) (measured according to the MS method described in general procedure C from the part 'compound identification')

h) Preparation of Compound A51

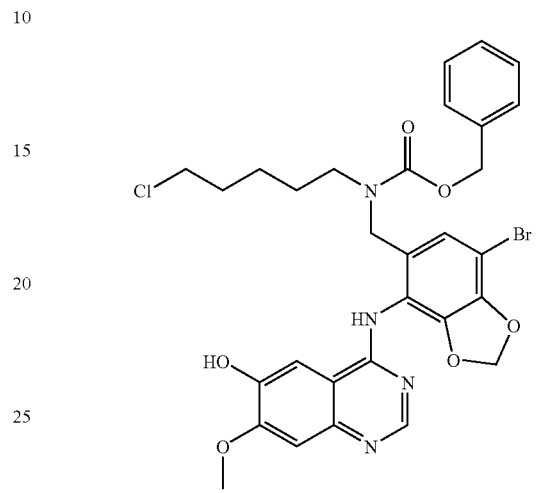

To a solution of the crude compound A50 (0.44 mmol) in CH$_3$OH (2 ml) was added a 32% HCl solution (0.84 mmol; 0.083 ml). The reaction mixture was stirred at 50° C. for 6.5 hours and at room temperature overnight. The solvent was evaporated under reduced pressure. The residue was taken up with a saturated aqueous NaHCO$_3$ solution and extracted with EtOAc. The combined organic extracts were washed with water and brine, then dried over Na$_2$SO$_4$, filtered, and concentrated under reduced pressure, yielding 0.283 g (98% yield, which was used directly for the next step) of compound A51.

Analytical HPLC: Method 1, Rt=4.48 (93%). APCI-MS: 657/659/661 (100, [M+H]$^+$).

i) Preparation of Compound A52

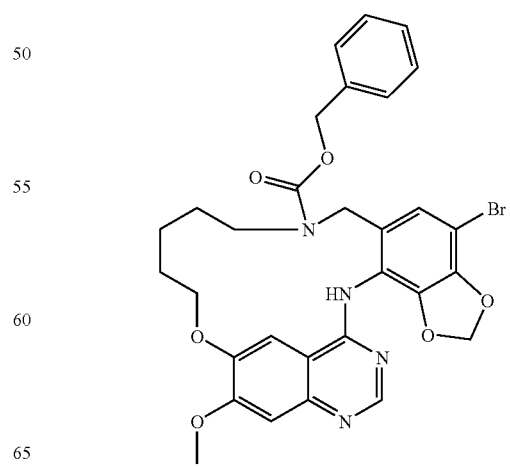

To a suspension of $Cs_2CO_3$ (2.57 mmol) in anhydrous DMA (10.6 ml) was slowly added (over 3.25 hours, using a syringe pump) at 65° C., a solution of compound A51 (0.343 mmol) in anhydrous DMA (4.2 ml). The reaction mixture was then further stirred at 65° C. for 12 hours, allowed to cool to room temperature, poured into a mixture of ice-water and extracted with EtOAc. The combined organic extracts were washed several times with water, brine, dried ($Na_2SO_4$), filtered, and concentrated under reduced pressure. The crude product was purified by silica gel chromatography (eluent: $CH_2Cl_2/CH_3OH$ 100:0 to 97:3). The product fractions were collected and the solvent was evaporated, yielding 0.107 g (50%, as a pale yellow powder) of compound A52.

APCI-MS 621/623 (100, [M+H]$^+$) (measured according to the MS method described in general procedure C from the part 'compound identification')

Example A8 a) Preparation of Compond A53

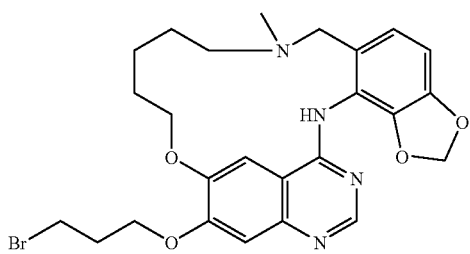 [SMILES: CN1CCCCCOc2cc3c(ncnc3cc2OCCCBr)Nc2c(ccc3c2OCO3)C1]

A mixture of compound A12 (0.73 mmol) and triphenylphosphine (1.54 mmol) was dried under vacuum for 10 minutes and treated with dry THF (14 ml). 3-Bromo-1-propanol (1.17 mmol) was added. A solution of DIPEA (1.17 mmol) in dry THF (6 ml) was added dropwise. The mixture was stirred at room temperature for 2 hours. Extra bromo-1-propanol (0.59 mmol), triphenylphosphine (0.77 mmol) and DIPEA (0.59 mmol) were added. Stirring was continued for 1.75 hours. The solvents were evaporated. The residue was purified by flash column chromatography over silica gel (eluent: $CH_2Cl_2/CH_3OH$ 100:0 to 97:3). The product fractions were collected and the solvent was evaporated. The solid residue was suspended in $CH_2Cl_2$/EtOAc and filtered. The solid was dried in vacuum, yielding 0.230 g (59.2%) of compound A53.

APCI-MS: 528/530 (100, [M+H]$^+$) (measured according to the MS method described in general procedure C from the part 'compound identification').

Example A9 a) Preparation of Compound A54

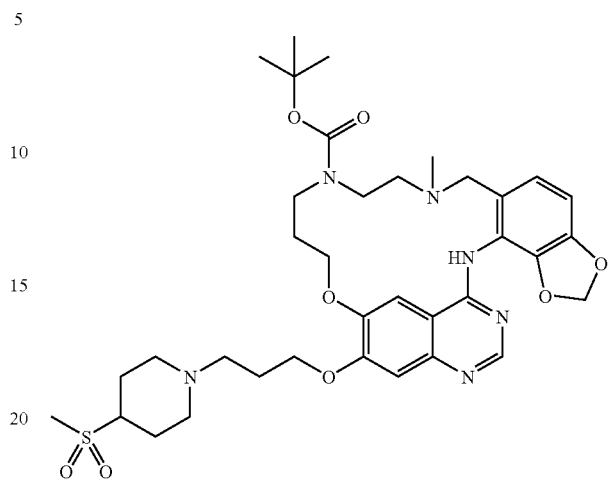

A mixture of compound A26 (0.124 mmol), 4-(methylsulfonyl)piperidine hydrochloride (0.298 mmol) and N-ethyl-N-(1-methylethyl)-2-propanamine (0.372 mmol) in acetonitrile (4 ml) was stirred overnight at 50° C. in a sealed tube. More 4-(methylsulfonyl)piperidine hydrochloride (0.298 mmol) and N-ethyl-N-(1-methylethyl)-2-propanamine (0.372 mmol) were added and the reaction mixture was stirred overnight at 50° C. This mixture was partitioned between a saturated aqueous $NaHCO_3$ solution and $CHCl_3$ (2×). The organic layer was separated, dried ($Na_2SO_4$), filtered and the solvent was evaporated. The residue was purified by column chromatography over silica gel (eluent: $CH_2Cl_2/CH_3OH$ from 100:0 to 95:5). The product fractions were collected and the solvent was evaporated, yielding 0.052 g (71%, yellow foam) of compound A54.

Example A 10 a) Preparation of Compound A55

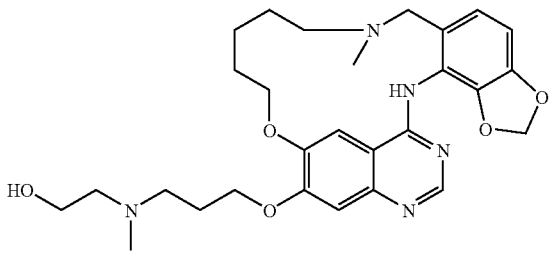 [SMILES: CN(CCO)CCCOc1cc2ncnc3c2cc1OCCCCCN(C)Cc1ccc2c(c1N3)OCO2]

A large excess of 2-(methylamino)ethanol (8.575 mmol) was added to a mixture of compound A53 (0.245 mmol) in dry acetonitrile (8 ml). The reaction mixture was stirred overnight at room temperature. Then the mixture was heated to 75° C. and it was stirred again overnight. The mixture was extracted with $CHCl_3$. The separated organic layer was washed with a saturated $NaHCO_3$ solution, dried ($Na_2SO_4$), filtered and the solvent was evaporated. The residue was purified by flash column chromatography over silica gel (eluent: $CH_2Cl_2$, $CH_2Cl_2/(CH_3OH/NH_3)$). The product fractions were collected and the solvent was evaporated, yielding 0.120 g (93.5%) of compound A55.

Example A11 a) Preparation of Compound A56

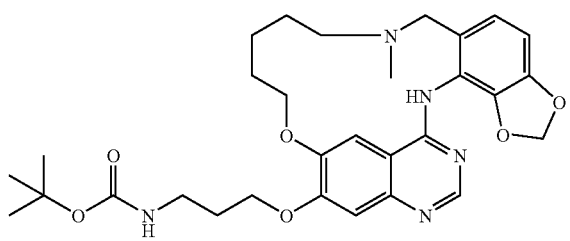 [SMILES: CN1CCCCCOc2cc3c(ncnc3cc2OCCCNC(=O)OC(C)(C)C)Nc2c(ccc3c2OCO3)C1]

A mixture of compound A12 (100 mg, 0.25 mmol) and triphenylphosphine (135 mg, 0.52 mmol) was dried i.v. for 10 minutes and treated with dry THF (5 ml). (3-Hydroxypropyl)-1,1-dimethylethyl ester carbamic acid (69 mg, 0.39 mmol) was added. A solution of DIAD (0.076 ml, 0.39 mmol) in dry THF (2 ml) was added slowly. The mixture was stirred at room temperature for 16 hours. The solvents were evaporated, the residue was dried i.v. and purified by preparative high-performance liquid chromatography (eluent: hexane/EtOAc/CH$_3$OH gradient). The product fractions were collected and the solvent was evaporated, yielding 0.105 g (76%) of compound A56.

M.P.: 210-213° C. Analytical HPLC: Method 2, Rt=3.40 (97%). APCI-MS: 566 (100 [M+H]$^+$).

b) Preparation of Compound A57

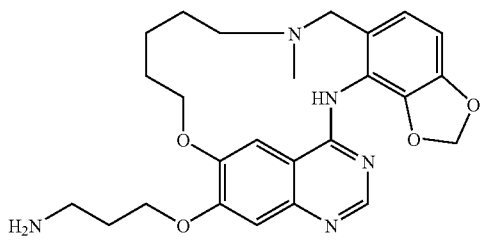 [SMILES: CN1CCCCCOc2cc3c(ncnc3cc2OCCCN)Nc2c(ccc3c2OCO3)C1]

A suspension of compound A56 (90 mg, 0.16 mmol) in dry CH$_2$Cl$_2$ (3 ml) was treated with TFA (3 ml) and allowed to stir at room temperature for 3 hours. The residue was partitioned between CHCl$_3$ and a saturated aqueous NaHCO$_3$. The organic layer was separated, dried (Na$_2$SO$_4$), filtered and the solvent was evaporated, yielding 0.074 g (quantitative) of compound A57. M.P.: dec>190° C. Analytical HPLC: Method 1, Rt=2.77 (98%). APCI-MS: 466 (100 [M+H]$^+$).

c) Preparation of Compound A58

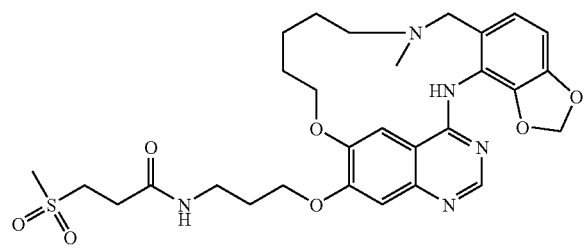 [SMILES: CN1CCCCCOc2cc3c(ncnc3cc2OCCCNC(=O)CCS(C)(=O)=O)Nc2c(ccc3c2OCO3)C1]

DIPEA (0.000560 mol) was added to a suspension of compound A57 (0.000140 mol), 3-(methylsulfonyl)propanoic acid (0.154 mmol), 6-chloro-1-hydroxy-1H-benzotriazole (0.168 mmol) and HCTU (0.168 mmol) in dry DMF (1 ml). The reaction mixture was stirred overnight and was then extracted with ethyl acetate. The separated organic layer was washed with a NaHCO$_3$ solution (semi-saturated), H$_2$O and brine. The organic layer was then dried (Na$_2$SO$_4$), filtered and the solvent was evaporated. The residue was purified by flash column chromatography over silica gel (eluent: CH$_2$Cl$_2$/CH$_3$OH), yielding 0.051 g (61%) of compound A58.

Example A12 a) Preparation of Compound A59

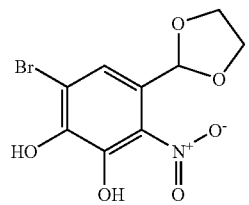 [SMILES: O=[N+]([O-])c1c(C2OCCO2)cc(Br)c(O)c1O]

A mixture of compound A44 (0.08350 mol) and Dowex® resin (21.3 g) in toluene (870 ml) was stirred at room temperature. 1,2-Ethanediol (0.83495 mol) was added and the reaction mixture was stirred and refluxed overnight under argon atmosphere. The reaction mixture was filtered. The residue was washed with methanol. The filtrate was evaporated. The brown oily residue was extracted with EtOAc. The separated organic layer was dried, washed with water (2×), once with brine, then dried (Na$_2$SO$_4$), filtered and the solvent was evaporated, yielding 25.9 g of compound A59.

b) Preparation of Compound A60

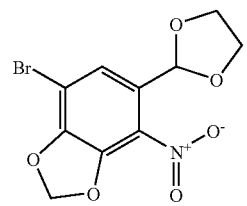 [SMILES: O=[N+]([O-])c1c(C2OCCO2)cc(Br)c2c1OCO2]

To a solution of catechol compound A59 (25.9 g, 84.6 mmol) and copper (II) oxide (2.42 g, 30.5 mmol) in anhydrous DMF (660 ml) was added diiodomethane (34 ml, 0.43 mol). Sodium hydride (60% in mineral oil, 8.5 g, 0.19 mol) was added portionwise. The reaction mixture was then stirred at 80° C. for 13 hours, allowed to cool to ambient temperature, poured into water and extracted with EtOAc. The combined organic extracts were washed with brine, dried (Na$_2$SO$_4$), filtered, concentrated under reduced pressure, and purified by silica gel chromatography (EtOAc/hexanes 0:100 to 40:60) to afford 13.1 g (49% over the two steps), of compound A60 as a yellow powder.

$C_{10}H_8BrNO_6$ (318.1). $^1$H-NMR (DMSO-d6): 7.27 (s, 1 H), 6.38 (s, 2 H), 6.21 (s, 1 H), 3.92 (m, 4 H).

c) Preparation of Compound A61

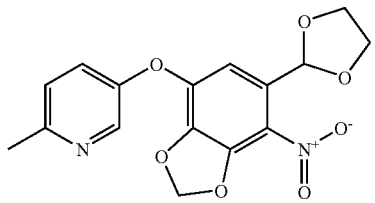 [SMILES: Cc1ccc(Oc2cc(C3OCCO3)c([N+](=O)[O-])c3c2OCO3)cn1]

A mixture of compound A60 (9.43 mmol), 6-methyl-3-pyridinol (18.86 mmol), Cu-powder (9.43 mmol) and $Cs_2CO_3$ (14.13 mmol) in dry DMF (50 ml) was stirred for 5 hours at 90° C. Heating was stopped and the mixture was extracted with EtOAc. The separated organic layer was washed with a half-saturated aqueous NaCl solution, once with brine, dried ($Na_2SO_4$), filtered and the solvent was evaporated. The residue (brown oil) was purified by column chromatography over silica gel (eluent: hexane/EtOAc 7/3 to 1/1). The product fractions were collected and the solvent was evaporated, yielding 1.78 g (27%) of compound A61.

d) Preparation of Compound A62

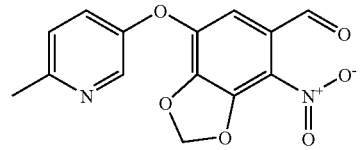 [SMILES: Cc1ccc(Oc2cc(C=O)c([N+](=O)[O-])c3c2OCO3)cn1]

A mixture of compound A61 (6.7 mmol) in $CH_2Cl_2$ (90 ml) and $H_2O$ (30 ml) was stirred. TFA (30 ml) was added. The reaction mixture was stirred over the weekend at 40° C. The solvent was evaporated. The aqueous concentrate was partitioned between EtOAc (500 ml) and a 10% aqueous $K_2CO_3$ solution (400 ml). The biphasic mixture was stirred vigorously. $K_2CO_3$ powder was added portionwise until alkaline. The organic layer was separated, washed with a 10% aqueous $K_2CO_3$ solution, dried ($Na_2SO_4$), filtered and the solvent was evaporated, then co-evaporated with $Et_2O$, yielding 1.92 g (94.5%) of compound A62.

e) Preparation of Compound A63

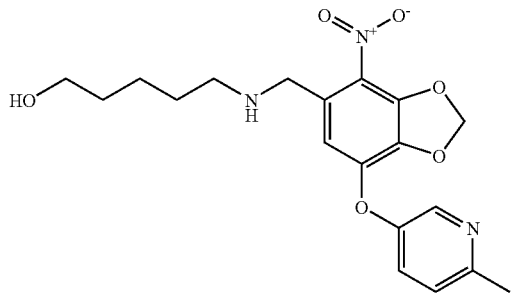 [SMILES: Cc1ccc(Oc2cc(CNCCCCCO)c([N+](=O)[O-])c3c2OCO3)cn1]

Compound A62 (7.18 mmol) was dissolved in 1,2-dichloroethane (87 ml). 5-Amino-1-pentanol (14.36 mmol) was added and the mixture was stirred for 15 minutes at room temperature. The mixture was then cooled to 0° C. and acetic acid (14.36 mmol) was added. $NaBH(OAc)_3$ (14.36 mmol) was added portionwise and the resultant reaction mixture was stirred for 15 minutes at 0° C. The mixture was allowed to warm to room temperature and stirring was continued overnight. The reaction mixture was partitioned between (2×) $CH_2Cl_2$ and a saturated aqueous $NaHCO_3$ solution. The organic layer was separated, dried ($Na_2SO_4$), filtered and the solvent was evaporated, yielding 2.85 g (yellow oil; used in next reaction step, without further purification) of compound A63.

f) Preparation of Compound A64

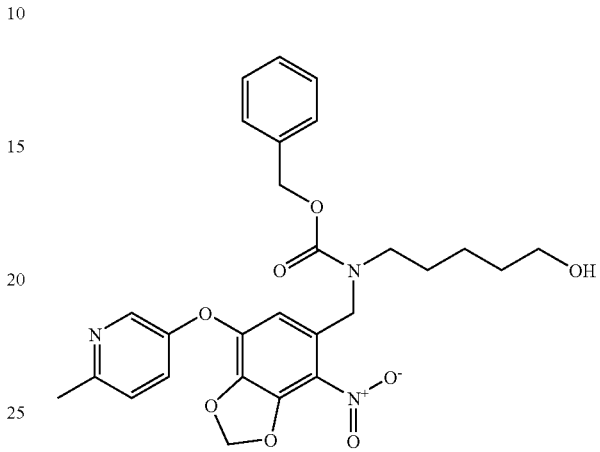

Compound A63 (7.18 mmol) was dissolved in dry $CH_2Cl_2$ (87 ml). The solution was cooled on an ice-bath. 1-[[(Phenylmethoxy)carbonyl]oxy]-2,5-pyrrolidinedione (7.90 mmol) was added portionwise. The reaction mixture was stirred for 30 minutes at 0° C., then for 3 hours at room temperature. The reaction mixture was extracted twice with $CH_2Cl_2$, washed with water, dried ($Na_2SO_4$), filtered and the solvent was evaporated to give a residue which was then purified by column chromatography over silica gel (eluent: hexane/EtOAc 70/30 to 100/0). The product fractions were collected and the solvent was evaporated, yielding 4.85 g of compound A64.

g) Preparation of Compound A65

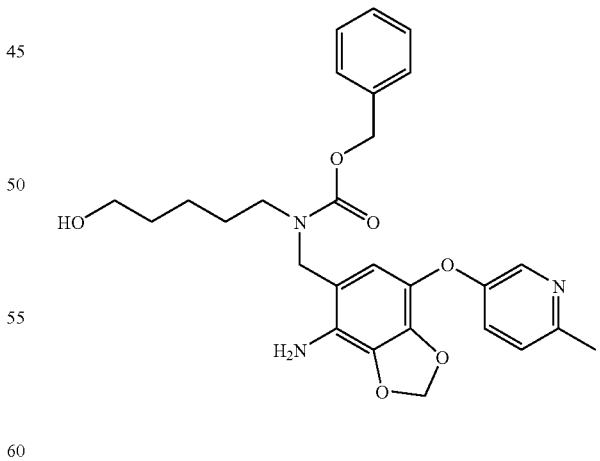

A solution of compound A64 (3.820 mmol) in $CH_3OH$ (80 ml) was hydrogenated for 4 hours with Pt/C (5%) (0.3 g) as a catalyst. After uptake of $H_2$ (3 equiv.), the catalyst was filtered off over $Na_2SO_4$ and Celite, and the filtrate was evaporated, yielding 1.97 g (brown oil, used in next reaction step, without further purification) of compound A65.

h) Preparation of Compound A66

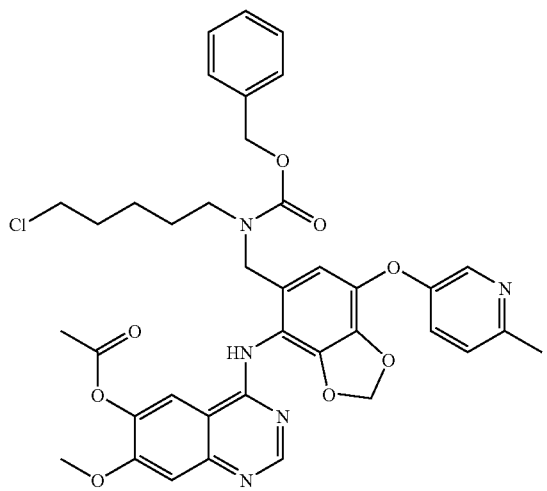 [SMILES: COc1cc2ncnc(Nc3c(CN(CCCCCCl)C(=O)OCc4ccccc4)cc(Oc4ccc(C)nc4)c4c3OCO4)c2cc1OC(C)=O]

Compound A65 (2.818 mmol) was dissolved in DMA (26 ml). Methanesulfonyl chloride (15.78 mmol) was added. The reaction mixture was stirred for 4 hours at 95° C. The reaction mixture was shaken with a mixture of EtOAc (700 ml) and a saturated aqueous NaHCO₃ solution (150 ml). The organic layer was separated and washed with an additional 150 ml of saturated aqueous NaHCO₃ solution (150 ml). The separated organic layer was washed with water (5×100 ml), once with brine (100 ml), then dried (Na₂SO₄), filtered and the solvent was evaporated, yielding 2.01 g (used in next reaction step, without further purification) of compound A66.

i) Preparation of Compound A67

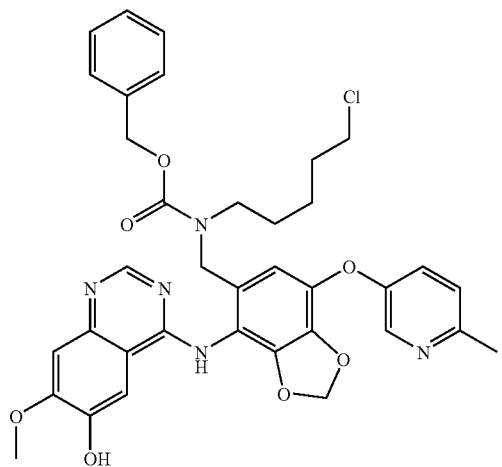 [SMILES: COc1cc2ncnc(Nc3c(CN(CCCCCCl)C(=O)OCc4ccccc4)cc(Oc4ccc(C)nc4)c4c3OCO4)c2cc1O]

Compound A66 (2.8 mmol) was dissolved in CH₃OH (16 ml) and then a 32% HCl solution (0.66 ml) was added. The reaction mixture was heated to 50° C. and stirred overnight. The solvent was evaporated and the residue was extracted with EtOAc (3×) and washed with a saturated aqueous NaHCO₃ solution. The separated organic layer was washed with H₂O and brine, dried (Na₂SO₄), filtered and the solvent was evaporated, yielding 1.9 g (used in the next reaction step, without further purification) of compound A67.

j) Preparation of Compound A68

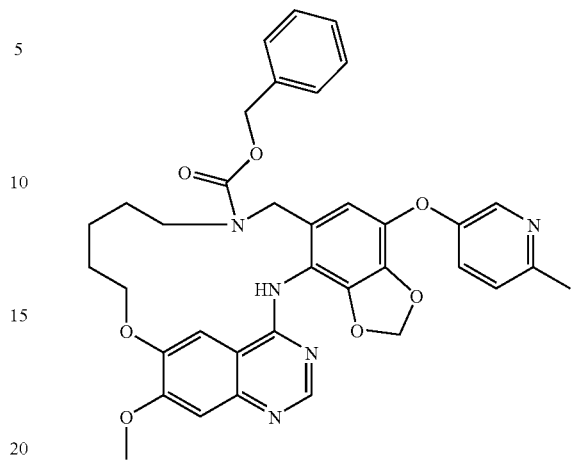

Cs₂CO₃ (21.42 mmol) was suspended in thiobismethane (85 ml) and the suspension was heated to 60° C. under an inert atmosphere. A solution of compound A67 (2.818 mmol) in thiobismethane (40 ml) was added dropwise via a syringe over a 3.5 hours period. The reaction mixture was stirred overnight at 60° C. The reaction mixture was poured onto ice-water (1 L). This mixture was extracted with EtOAc (3×400 ml). The separated organic layer was washed with water (4×200 ml), brine (1×200 ml), dried (Na₂SO₄), filtered and the solvent was evaporated. The residue was purified by column chromatography over silica gel (eluent: CH₂Cl₂/CH₃OH from 100/0 to 96/4). The product fractions were collected and the solvent was evaporated, yielding 1.09 g (60%) of compound A68.

Example B1

Preparation of Compound B1

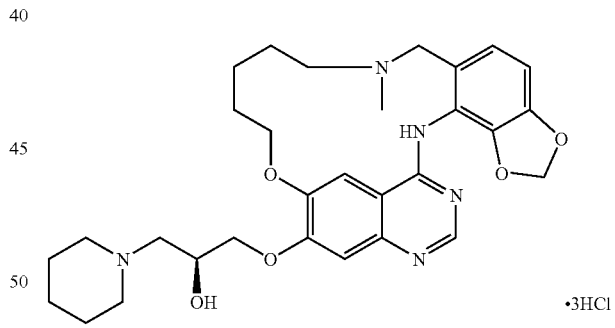

A solution of compound A13 (0.16 mmol) in CH₂Cl₂ (1 ml) and 2-propanol (5 ml) was treated with piperidine (1.6 mmol). The mixture was heated to 70° C. for 18 hours. The solvents were evaporated. The residue was purified by flash column chromatography over silica gel (eluent: CH₂Cl₂/CH₃OH 100:0 to 95:5). The product fractions were collected and the solvent was evaporated. A part (0.06 mmol) of this residue was treated with 2-propanol (3 ml)/conc. aqueous HCl solution (0.1 ml), filtered off and dried, yielding 0.038 g (93%) of compound B1 as a hydrochloride salt (S-configuration; 0.3HCl).

Analytical HPLC: Method 1, Rt=2.80 (98%). APCI-MS: 550 (100 [M+H]⁺)

The following compounds were prepared by analogy to Compound B1.

TABLE F-1

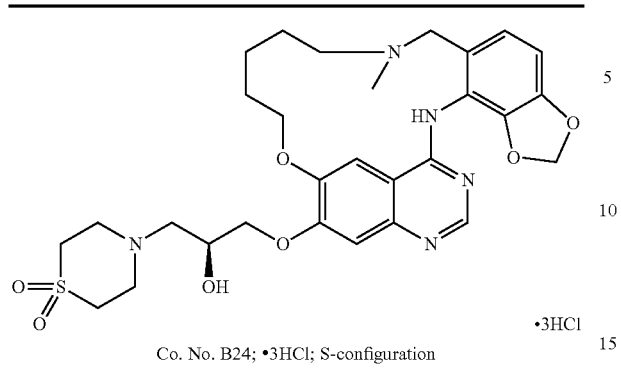

Co. No. B24; •3HCl; S-configuration

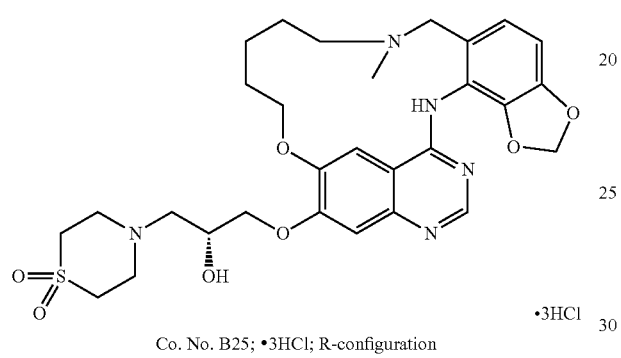

Co. No. B25; •3HCl; R-configuration

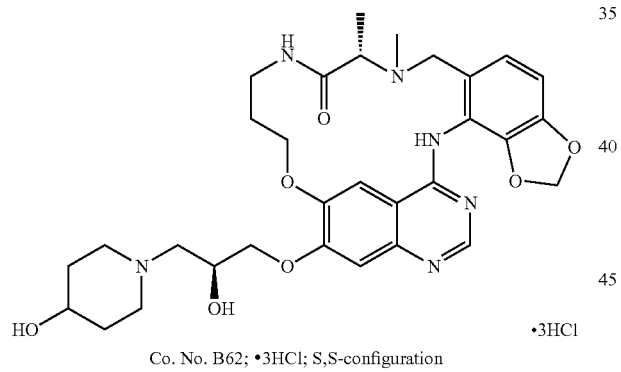

Co. No. B62; •3HCl; S,S-configuration

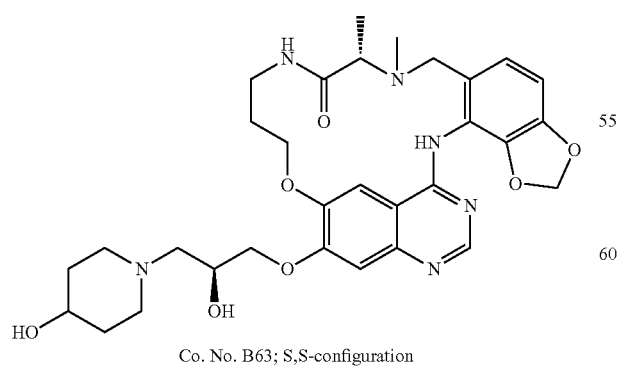

Co. No. B63; S,S-configuration

Example B2

Preparation of Compound B2

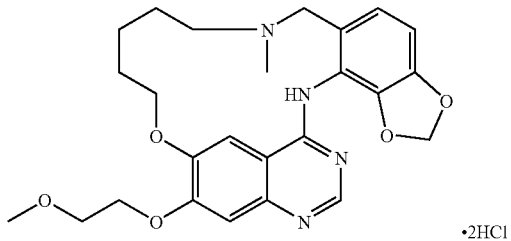 [SMILES: COCCOc1cc2ncnc3c2cc1OCCCCCN(C)Cc1ccc2c(c1N3)OCO2 ; "·2HCl"]

Co. No. B2; •2HCl

A mixture of compound A12 (0.10 mmol) and triphenylphosphine (0.14 mmol) was treated with THF (2 ml) and with 2-methoxyethanol (0.68 mmol). A solution of bis(1-methylethyl)ester diazenedicarboxylic acid (0.11 mmol) in THF (0.5 ml) was added slowly. The mixture was stirred over 3 hours at room temperature, then additional triphenylphosphine (19 mg, 0.07 mmol) and bis(1-methylethyl)ester diazenedicarboxylic acid (0.06 mmol) were added and stirring was continued for 3 hours. The residue was partitioned between water and $CH_2Cl_2$. The separated organic layer was dried ($Na_2SO_4$), filtered and the solvent evaporated. The residue (brown oil, 154 mg) was purified by flash column chromatography over silica gel (eluent: $CH_3Cl$/EtOH 99:1 to 95:5). The product fractions were collected and the solvent was evaporated, yielding 0.027 g (60.5%, light powder) of compound B2 as a hydrochloride salt (0.2HCl).

Analytical HPLC: Method 1, Rt=1.52 (98%). APCI-MS: 467 (100 [M+H]$^+$)

The following compounds were prepared by analogy to Compound B2.

TABLE F-2

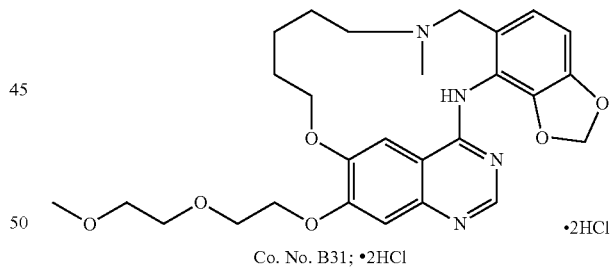

Co. No. B31; •2HCl

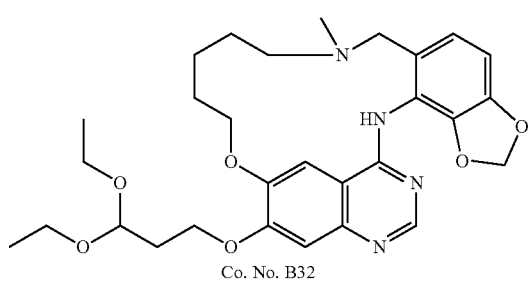

Co. No. B32

TABLE F-2-continued

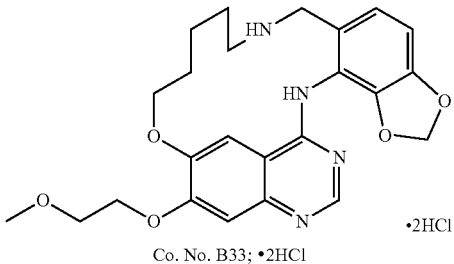

Co. No. B33; •2HCl

Example B3

Preparation of Compound B3

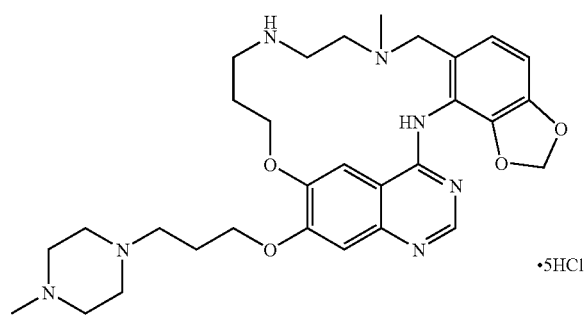 [SMILES: CN1CCN(CCCOc2cc3ncnc4c3cc2OCCCNCCN(C)Cc2ccc3c(c2N4)OCO3)CC1 ; "·5HCl"]

A mixture of compound A27 (0.104 mmol) in Et$_2$O (q.s.) was stirred and cooled to 0° C. in an ice-bath under N$_2$ atmosphere. HCl (4N in dioxane) (3 ml) was added and the mixture was stirred for 15 minutes in the ice-bath, then for 2 hours at room temperature. The solvent was evaporated. Et$_2$O was added. The mixture was stirred for 30 minutes at room temperature. The precipitate was filtered off, washed with Et$_2$O and dried, yielding 0.073 g (93.6%) of compound B3 as a hydrochloride salt (0.5HCl).

The following compounds were prepared by analogy to Compound B3.

TABLE F-3

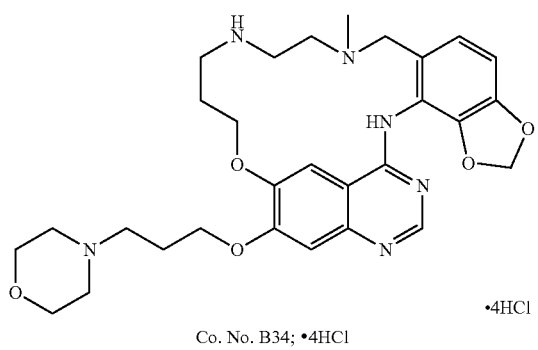

Co. No. B34; •4HCl

Example B4

Preparation of Compound B4

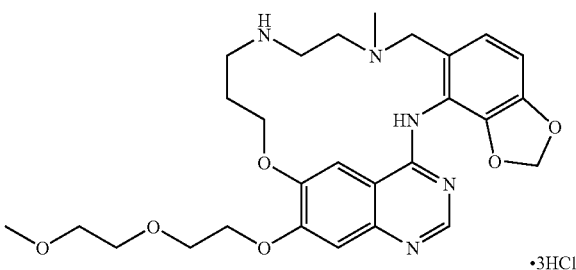 [SMILES: COCCOCCOc1cc2ncnc3c2cc1OCCCNCCN(C)Cc1ccc2c(c1N3)OCO2 ; "·3HCl"]

A mixture of compound A28 (0.089 mmol) in Et$_2$O (q.s.) was stirred and cooled in an ice-bath under N$_2$ atmosphere. HCl (4N in dioxane) (3 ml) was added and the mixture was stirred for 15 minutes at 0° C., then for 30 minutes at room temperature. The solvent was evaporated. Et$_2$O was added and the mixture was stirred for another 30 minutes at room temperature. The precipitate was filtered off, washed with Et$_2$O and dried, yielding 0.042 g (73.7%) of compound B4 as a hydrochloride salt (0.3HCl).

Example B5

Preparation of Compound B5

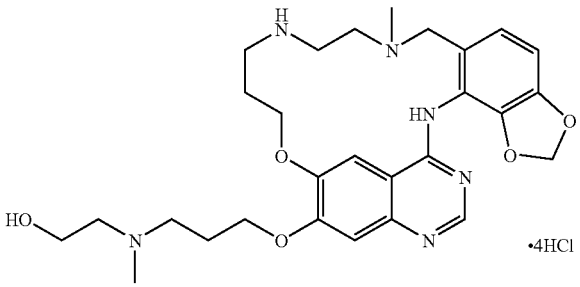 [SMILES: CN(CCO)CCCOc1cc2ncnc3c2cc1OCCCNCCN(C)Cc1ccc2c(c1N3)OCO2 ; "·4HCl"]

A mixture of compound A29 (0.000097 mol) in Et$_2$O (q.s.) was stirred and cooled on an ice-bath under N$_2$ atmosphere. HCl (4N in dioxane) (3 ml) was added and the mixture was stirred for 15 minutes on the ice-bath, then for 2 hours at room temperature. The solvent was evaporated. Et$_2$O was added and the mixture was stirred for another 30 minutes at room temperature. The precipitate was filtered off, washed with Et$_2$O and dried, yielding 0.072 g (quantitative yield; used in next reaction step without further purification) of compound B5 as a hydrochloride salt (0.4HCl).

The following compounds were prepared by analogy to Compound B5.

TABLE F-4

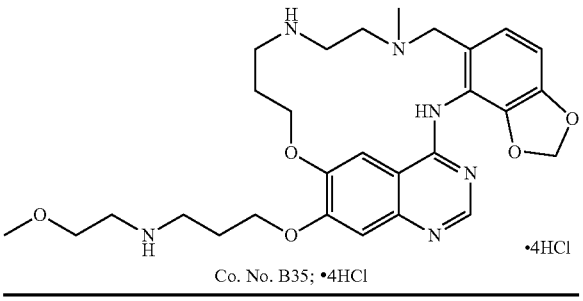

Co. No. B35; •4HCl

Example B6

Preparation of Compound B6

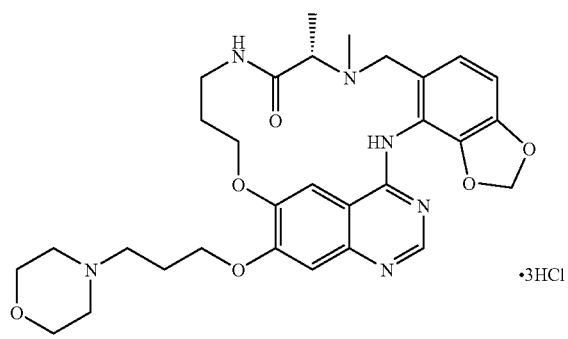 [SMILES: C[C@H]1C(=O)NCCCOc2cc3c(ncnc3cc2OCCCN2CCOCC2)Nc2c(ccc3c2OCO3)CN1C ; "·3HCl"]
•3HCl

To a suspension of compound A42 (0.16 mmol) in 2-propanol (3 ml) was added a 32% aqueous HCl solution (0.1 ml). The mixture was then concentrated to dryness under reduced pressure, redissolved in a mixture of 2-propanol/32% aqueous HCl solution (3:0.1 ml) and reconcentrated. The residual amounts of aqueous HCl were removed by coevaporation with 2-propanol (×3) and Et$_2$O (×1). The residue was taken up in Et$_2$O, filtered and washed with Et$_2$O. The solid was then collected and dried, yielding 0.098 g (91%, as a light powder) of compound B6 as a hydrochloride salt (0.3HCl; S-configuration).

M.P.: dec.>198° C. Analytical HPLC: Method 1, Rt=2.71 (96%). APCI-MS: 579 (100, [M+H]$^+$)

The HCl-salts in Table F-5 were prepared by analogy to Compound B6. The free bases in Table F-5 were prepared by analogy to compound A42 (compound A42 is the free base of compound B6).

TABLE F-5

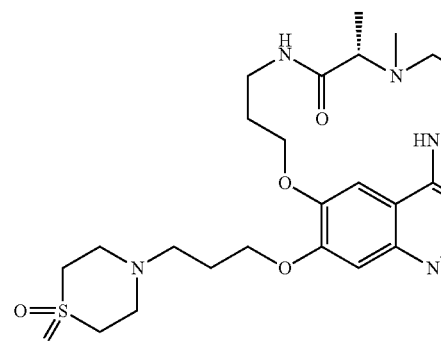
•3HCl

Co. No. B36; •3HCl; S-configuration

TABLE F-5-continued

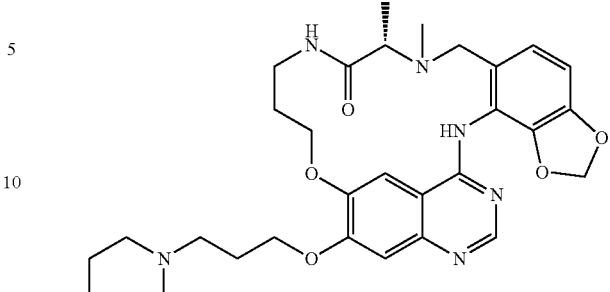

Co. No. B37; S-configuration

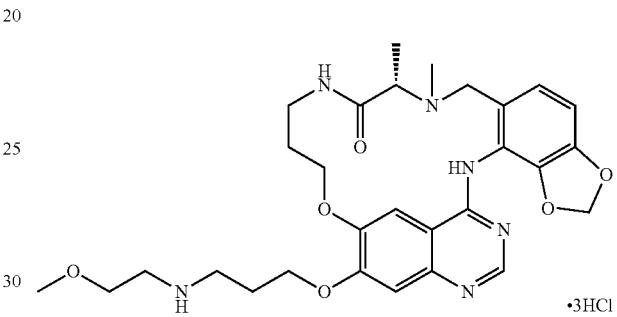
•3HCl

Co. No. B38; •3HCl; S-configuration

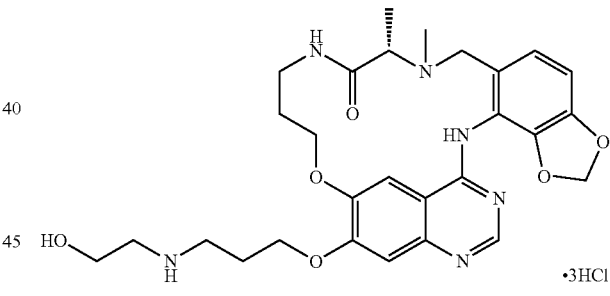
•3HCl

Co. No. B39; •3HCl; S-configuration

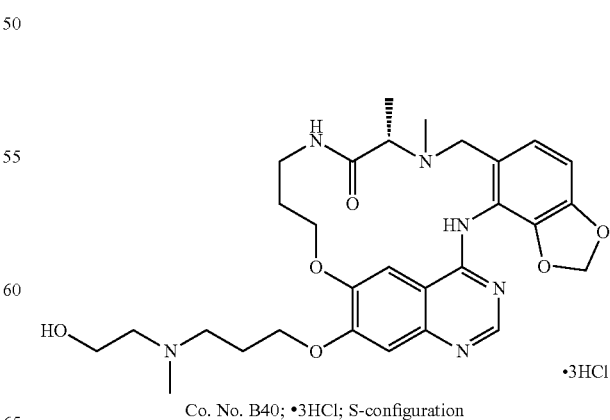
•3HCl

Co. No. B40; •3HCl; S-configuration

Example B7

Preparation of Compound B7

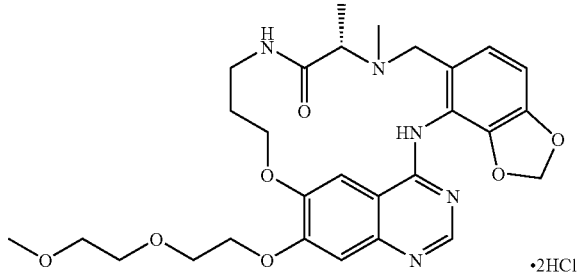 [SMILES: COCCOCCOc1cc2ncnc3c2cc1OCCCNC(=O)[C@H](C)N(C)Cc1ccc2c(c1N3)OCO2 ; "·2HCl"]
•2HCl

To a suspension of compound A43 (0.126 mmol) in 2-propanol (3 ml) was added a 32% concentrated aqueous HCl solution (20 drops). The mixture was then concentrated to dryness under reduced pressure, redissolved in a mixture of 2-propanol/32% aqueous HCl solution (3:0.1 ml) and reconcentrated. The residual amounts of aqueous HCl were removed by coevaporation with 2-propanol (×3) and Et$_2$O (×1). The residue was taken up in Et$_2$O, filtered and washed with Et$_2$O. The solid was then collected and dried, yielding 0.070 g (89%, as a light powder) of compound B7 as a hydrochloride salt (0.2HCl; S-configuration).

The HCl-salts in Table F-6 were prepared by analogy to Compound B7. The free bases in Table F-6 were prepared by analogy to compound A43 (compound A43 is the free base of compound B7).

TABLE F-6

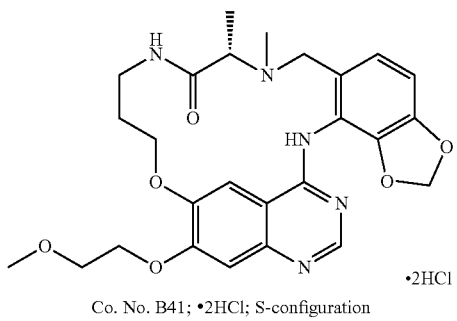
•2HCl
Co. No. B41; •2HCl; S-configuration

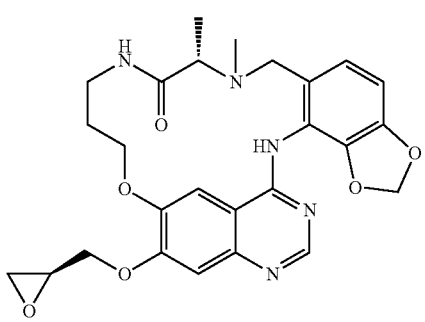 [SMILES: C[C@H]1C(=O)NCCCOc2cc3c(ncnc3cc2OC[C@@H]2CO2)Nc2c(ccc3c2OCO3)CN1C]
Co. No. B42; S,S-configuration

Example B8

Preparation of Compound B8

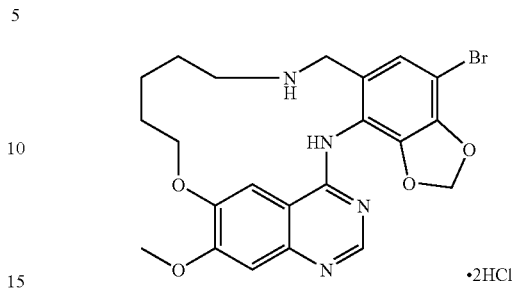
•2HCl

Debenzylation of compound A52 was achieved by adding 48% HBr solution (0.0142 mol) to compound A52 (0.171 mmol). The reaction mixture was stirred for 25 minutes at 80° C., then the mixture was allowed to cool to room temperature and the solvent was evaporated. 2-Propanol was added in order to coevaporate HBr. The residue was diluted with EtOAc, then washed with a saturated aqueous NaHCO$_3$ solution (×2), brine (×1), dried (Na$_2$SO$_4$), filtered and the solvent was evaporated. The residue (61 mg) was purified by column chromatography over silica gel (eluent: CH$_2$Cl$_2$/CH$_3$OH 100/0, 99/1, 98/2, 97/3 and 95/5). The purest product fractions were collected and the solvent was evaporated.

Salt formation was subsequently done by resuspending the residue (0.028 g) in 2-propanol (6 ml) and converted into the hydrochloride salt (0.2HCl) with a 32% aqueous HCl solution (10 drops). The solvent was evaporated under reduced pressure. The resultant powder was resuspended in 2-propanol and treated again with a 32% HCl solution (10 drops). The solvent was evaporated under reduced pressure. The residue was triturated under Et$_2$O. The solvent was evaporated. The residue was triturated under Et$_2$O, filtered off, washed three times with Et$_2$O, filtered off and dried, yielding 0.0285 g of compound B8 as a hydrochloride salt (0.2HCl)

The following compounds were prepared by analogy to Compound B8.

TABLE F-7

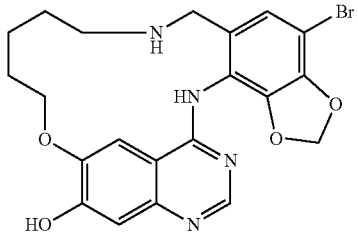 [SMILES: Oc1cc2ncnc3c2cc1OCCCCCNCc1cc(Br)c2c(c1N3)OCO2]
Co. No. B44

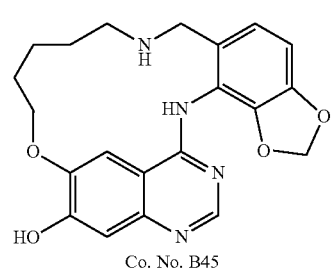
Co. No. B45

TABLE F-7-continued
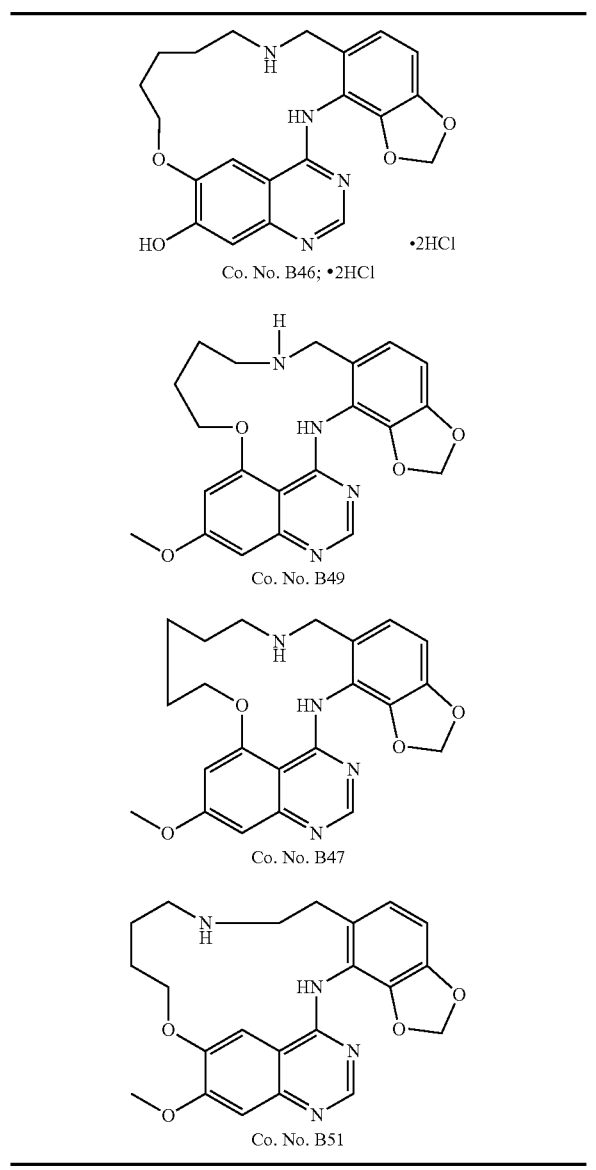
Compound B50
was prepared by analogy to compound A52.
But for the debenzylation reaction, the following compounds were prepared by analogy to Compound B8.
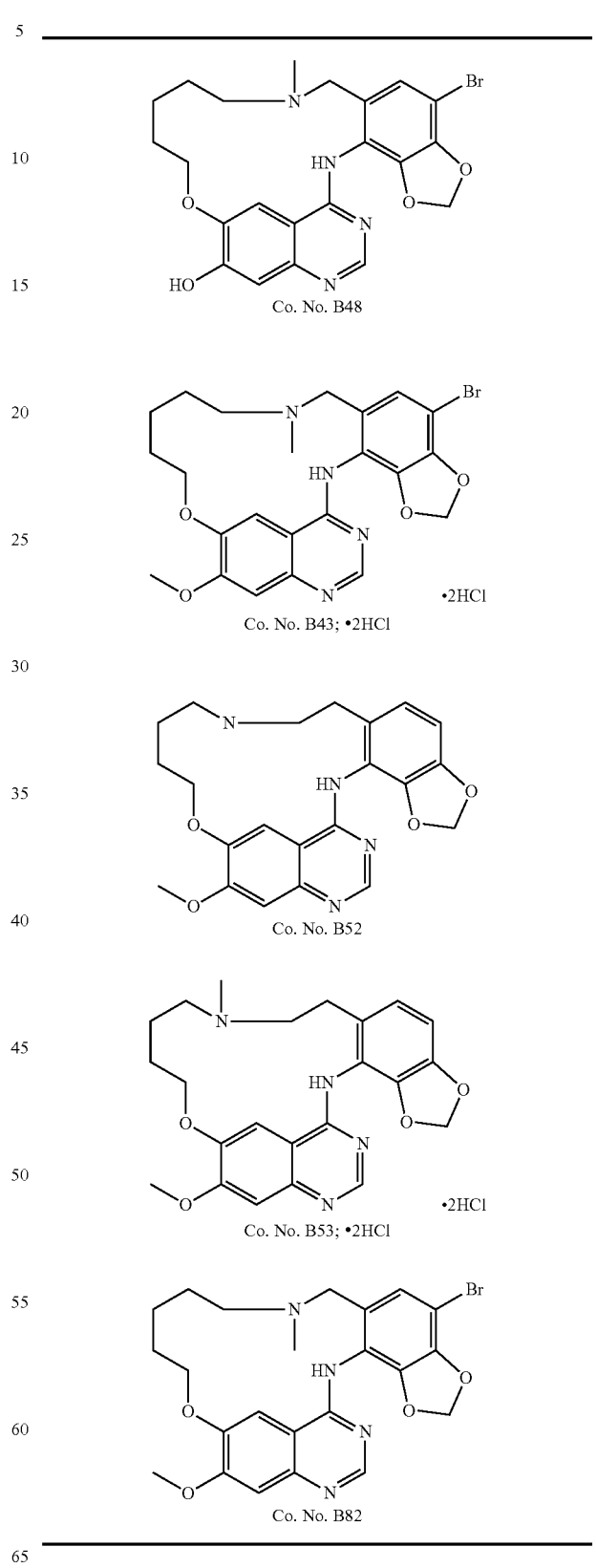

Example B9

Preparation of Compound B9 and B10

Compound B9

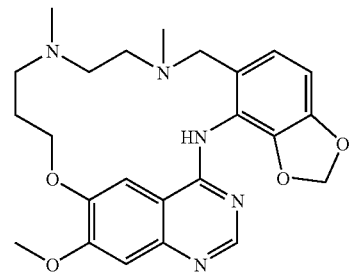

Compound B10

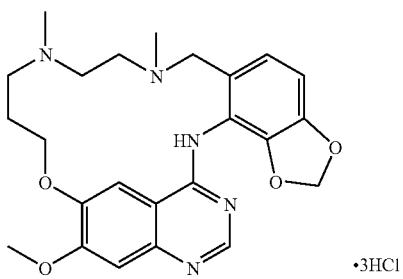
·3HCl

A mixture of compound A21 (0.23 mmol) and paraformaldehyde (4.6 mmol) was dissolved in CH₃OH (16 ml) and acetic acid (26 51, 0.46 mmol). Under N₂, Pt/C (5%) (94 mg) was added and the mixture was hydrogenated under normal pressure at room temperature for 15 hours. The mixture was filtered trough a pad of celite and Na₂SO₄. The residue was washed (CH₃OH, then CH₃OH/CH₂Cl₂ 1:1). The filtrate was concentrated and the residue was worked-up (distribution of the residue between an organic solvent and aqueous solution, as indicated: CH₂Cl₂, saturated aqueous NaHCO₃ solution). The organic layer was dried (Na₂SO₄) and the solvent was evaporated yielding a white powder (94 mg) which was suspended in Et₂O/hexane 1:1. The product was filtered off, washed (Et₂O/hexane 1:1), and dried in vacuo, yielding 86 mg (83%) of compound B9.

Analytical HPLC: Method 2, Rt=2.62 (99%). APCI-MS: 452 (100, [M+H]⁺). ¹H-NMR (DMSO-d6): 11.2 (br. s, NH), 8.50 (s, 1 H), 7.99 (s, 1 H), 7.26 (s, 1 H), 6.82 (d, J=7.9, 1 H), 6.74 (d, J=7.8, 1 H), 6.03 (s, 2 H), 4.45 (br. t, OCH2), 3.98 (s, OCH3), 3.68 (br. s, 2H), 2.65 (br. s, 2 H), 2.44 (s, NCH3), 2.44-2.41 (br. m, 4 H), 2.00 (s, NCH3), 1.84 (br. m, 2 H).

A sample of compound B9 (0.16 mmol) was taken up in 2-propanol (3 ml) treated with 0.2 ml of a 32% aqueous HCl solution and evaporated. This treatment was repeated twice. The residue was then coevaporated twice from 2-propanol (2 ml) and Et₂O (2 ml). The residue was suspended in Et₂O and filtered. The solid was washed (Et₂O) and dried in vacuo, yielding 85 mg (79%) of compound B10 as a hydrochloride salt (0.3HCl).

Analytical HPLC: Method 2, Rt=2.61 (100%). APCI-MS: 452 (100, [M+H]⁺)

Example B10

Preparation of Compound B11

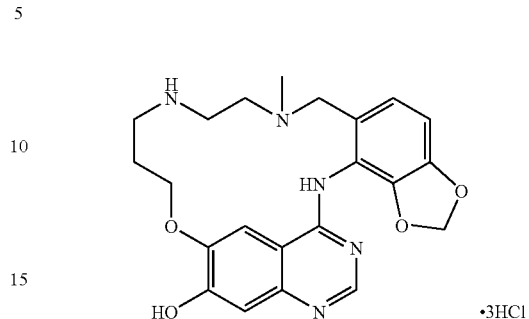
·3HCl

Compound A23 (0.142 mmol) was suspended in 2-propanol (3 ml). A 32% HCl solution (10 drops) was added dropwise at room temperature. The solvent was evaporated under vacuo. The residue was resuspended in 2-propanol (3 ml). A 32% HCl solution (10 drops) was added. The solvent was evaporated. 2-Propanol was added and coevaporated (2×). Et₂O was added and coevaporated (2×). The concentrate was filtered and the filter residue was washed with Et₂O, then dried, yielding 0.068 g (90.6%, yellow powder) of compound B11 as a hydrochloride salt (0.3HCl).

Example B11

Preparation of Compound B12

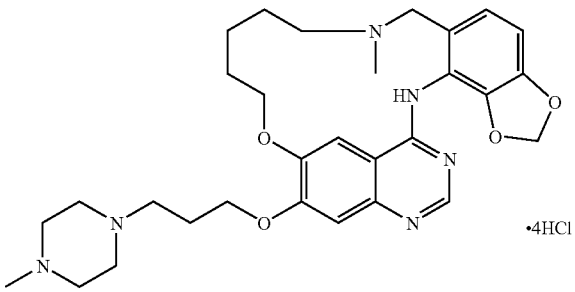 [SMILES: CN1CCN(CCCOc2cc3ncnc4c3cc2OCCCCCN(C)Cc2ccc3c(c2N4)OCO3)CC1 ; "·4HCl"]
·4HCl

Compound A53 (0.245 mmol) was suspended in acetonitrile (10 ml). 1-Methylpiperazine (9.01 mmol) was added and the reaction mixture was stirred for 18 hours at room temperature. An aqueous NaHCO₃ solution was added. This mixture was extracted with CHCl₃ (3×). The combined organic layers were dried (Na₂SO₄), filtered and the solvent evaporated. The residue was purified by flash column chromatography over silica gel (eluent: CH₂Cl₂/CH₃OH from 100/0 over 95/5 over CH₂Cl₂/CH₃OH/NH₄OH 94/5/1 to 90/9/1). The product fractions were collected and the solvent was evaporated. The residue was washed in Et₂O, filtered off and dried. This fraction (0.080 g) was dissolved in 2-propanol and converted into the hydrochloride salt (0.4HCl) with HCl/2-propanol. Following treatment with 2-propanol and Et₂O and coevaporation, the residue was suspended in Et₂O, filtered off, washed with Et₂O, then dried in vacuo, yielding 0.095 g of compound B12 as a hydrochloride salt (0.4HCl).

The following compounds were prepared by analogy to Compound B12.
TABLE F-8
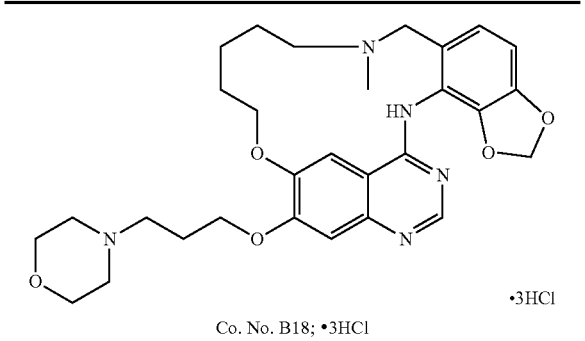
Co. No. B18; •3HCl
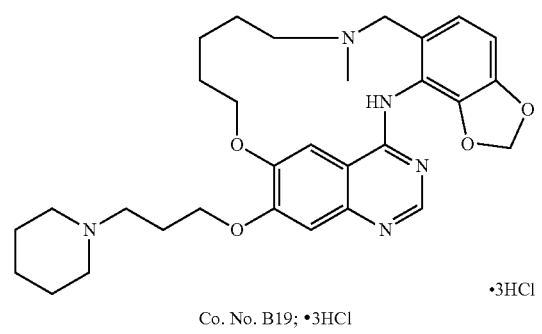
Co. No. B19; •3HCl
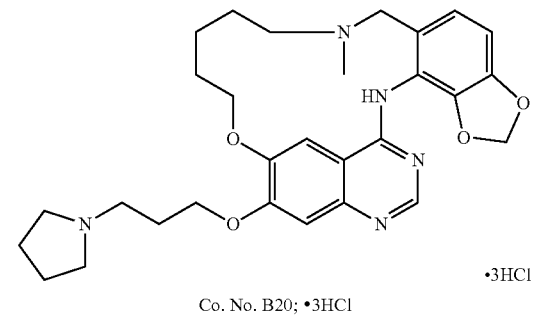
Co. No. B20; •3HCl
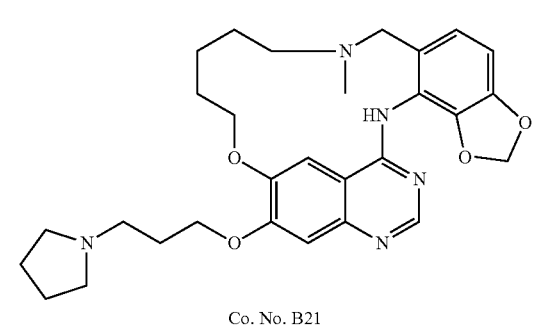
Co. No. B21
TABLE F-8-continued
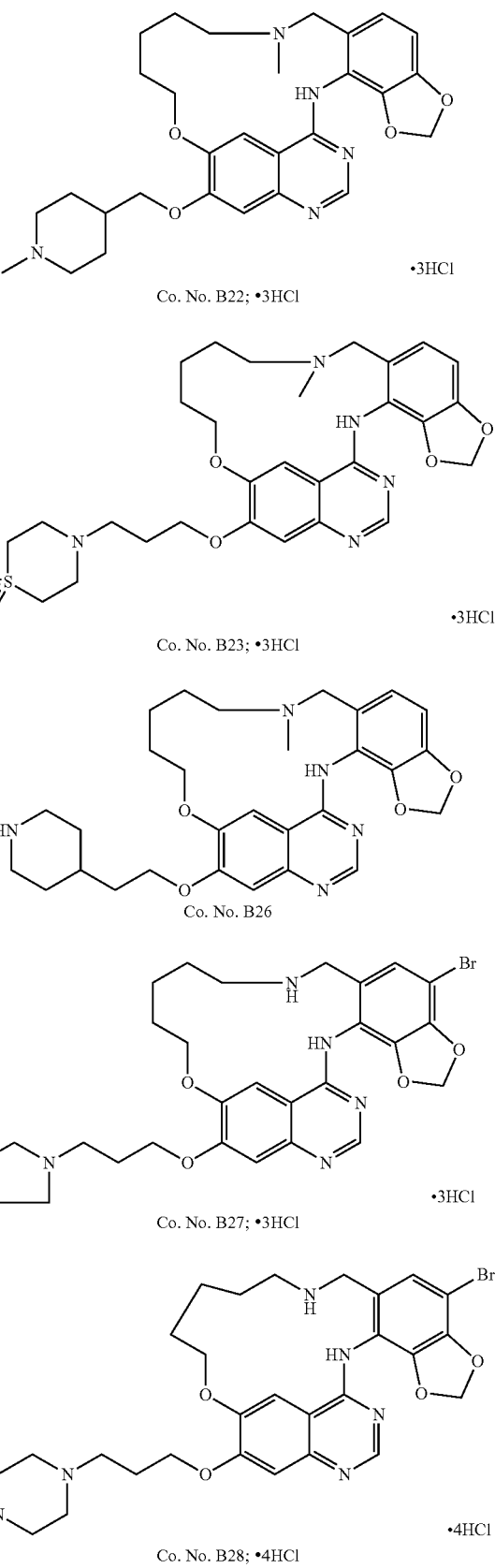
Co. No. B22; •3HCl
Co. No. B23; •3HCl
Co. No. B26
Co. No. B27; •3HCl
Co. No. B28; •4HCl TABLE F-8-continued
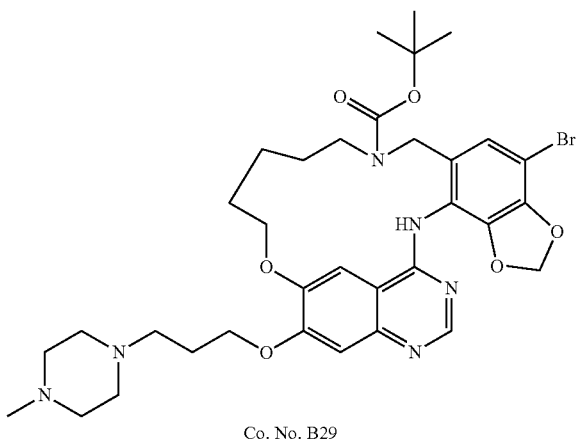
Co. No. B29
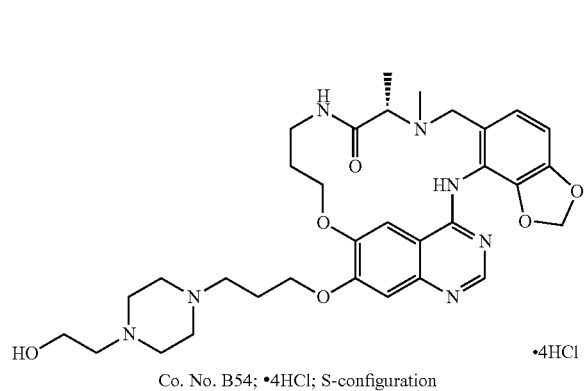
Co. No. B54; •4HCl; S-configuration
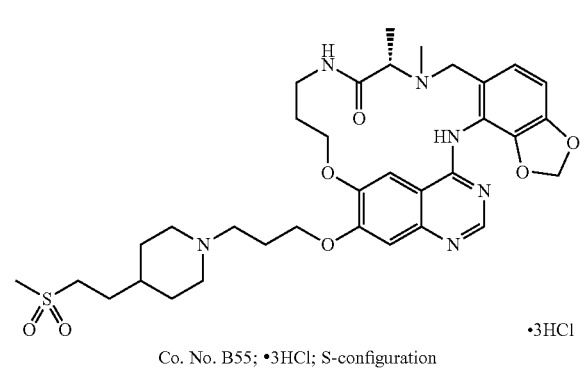
Co. No. B55; •3HCl; S-configuration
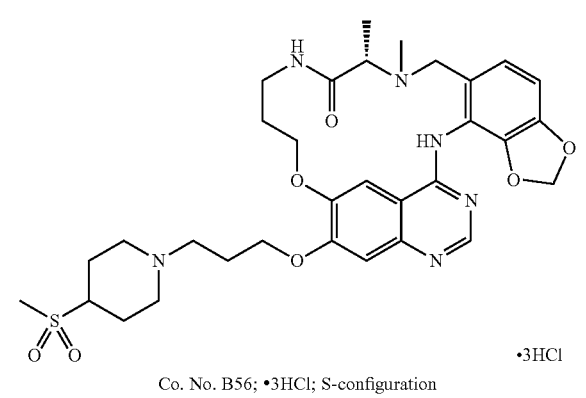
Co. No. B56; •3HCl; S-configuration
TABLE F-8-continued
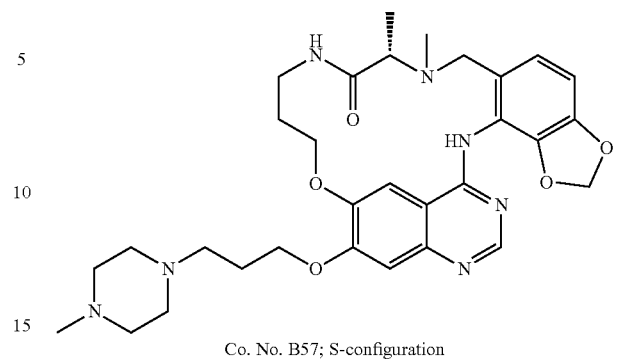
Co. No. B57; S-configuration
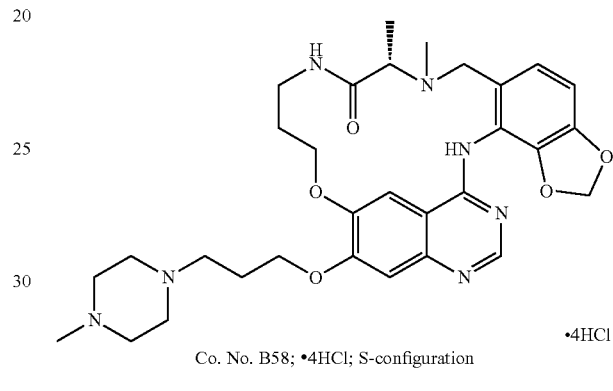
Co. No. B58; •4HCl; S-configuration
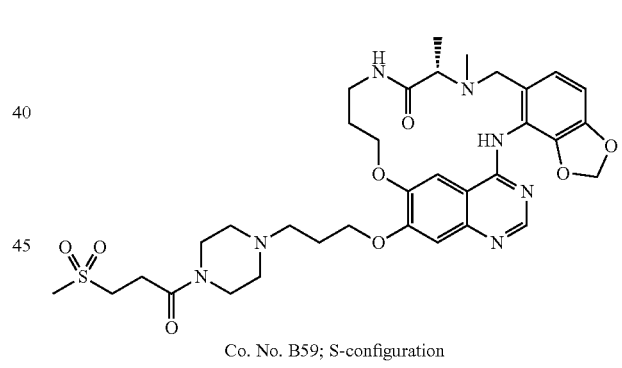
Co. No. B59; S-configuration
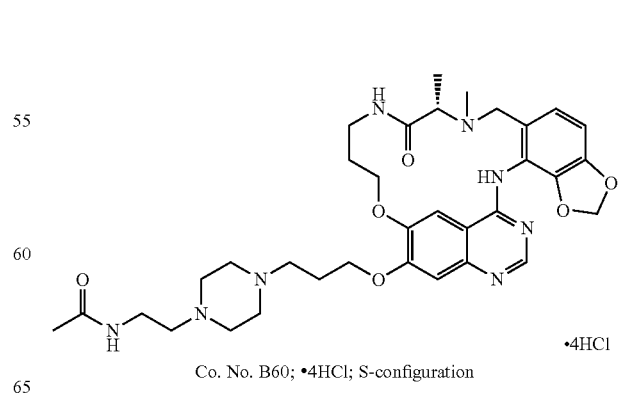
Co. No. B60; •4HCl; S-configuration TABLE F-8-continued

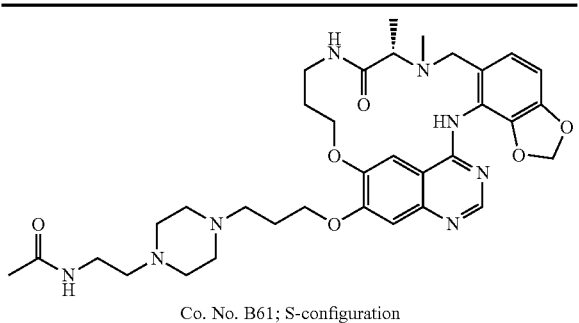

Co. No. B61; S-configuration

Example B12

Preparation of Compound B13

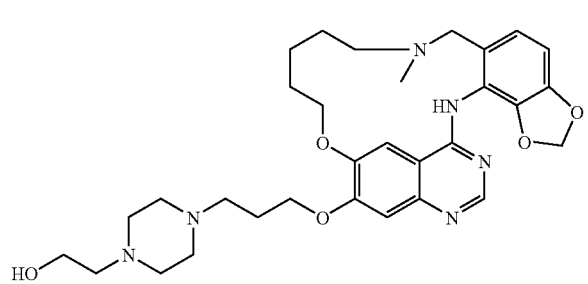 [SMILES: CN1CCCCCOc2cc3c(ncnc3cc2OCCCN2CCN(CCO)CC2)Nc2c(ccc3c2OCO3)C1]

1-piperazine ethanol (0.98 mmol) was added to a solution of compound A53 (0.15 mmol) in dry acetonitrile (8 ml). The solution was stirred at room temperature for 15 hours. Additional 1-piperazine ethanol (128 mg, 0.98 mmol) and acetonitrile (4 ml) were added and stirring was continued for 24 hours. The mixture was treated with $CH_2Cl_2$ and filtered. The filtrate was evaporated. The residue was partitioned between $CHCl_3$ and a saturated aqueous $NaHCO_3$ solution. The organic layer was separated, washed with a saturated aqueous NaCl solution, dried ($Na_2SO_4$), filtered and the solvent was evaporated. The residue (0.350 g) was purified by flash column chromatography over silica gel (eluent: $CH_2Cl_2$/$CH_3OH$/conc. aq. $NH_3$ 10:1:0.1). The product fractions were collected and the solvent was evaporated, yielding 0.070 g (84.3%) of compound B13.

Analytical HPLC: Method 1, Rt=2.78 (90%). APCI-MS: 579 ([M+H]$^+$), 153 (100).

The following compounds were prepared by analogy to Compound B13.

TABLE F-9

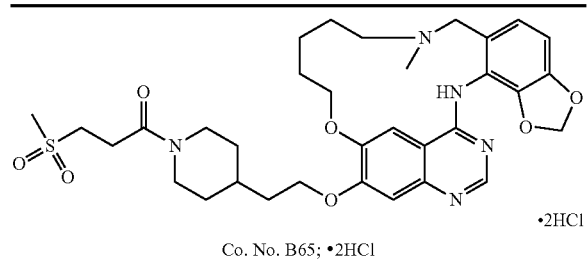

Co. No. B65; •2HCl

TABLE F-9-continued

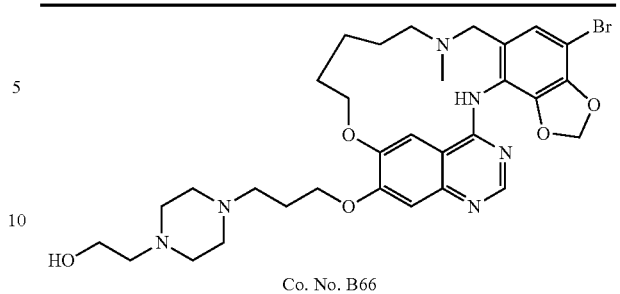

Co. No. B66

Example B13

Preparation of Compound B14

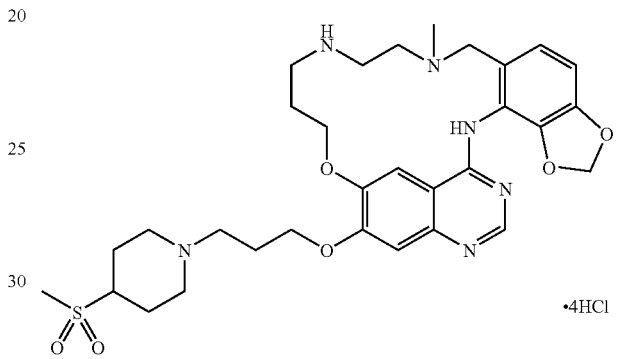

•4HCl

A mixture of compound A54 (0.063 mmol) in $Et_2O$ was stirred and cooled on an ice-bath. A HCl solution (4M in dioxane) (3 ml) was added and the reaction mixture was stirred for 30 minutes while maintaining the temperature at 0° C. Then, the reaction mixture was stirred for 2 hours at room temperature. The solvent was evaporated. The residue was triturated under $Et_2O$, filtered off, washed with $Et_2O$, then dried, yielding 0.066 g (quantitative yield; used in next reaction step, without further purification) of compound B14 as a hydrochloride salt (0.4HCl).

Example B14

Preparation of Compound B15

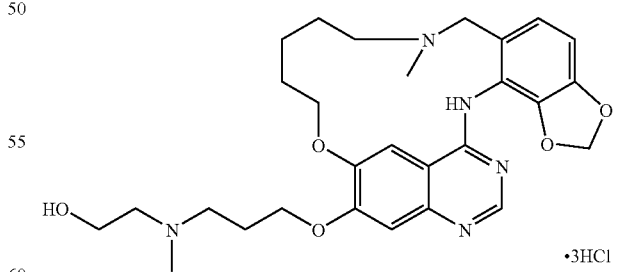

•3HCl

In a 10-ml round-bottom flask, a solution of compound A55 (0.187 mmol) in 2-propanol (3 ml) was treated with a 32% HCl solution (10 drops). The solvent was evaporated. The residue was dissolved in 2-propanol (3 ml) and treated again with a 32% HCl solution (10 drops). The solvent was evaporated. The residue was dissolved in 2-propanol (3 ml)

and the solvent was evaporated. The residue was suspended in Et₂O (3 ml), filtered off over a fritted glass filter, washed with Et₂O (3 ml), then dried, yielding 0.107 g (90%) of compound B15 as a hydrochloride salt (0.3HCl).

The HCl-salts in Table F-10 were prepared by analogy to Compound B15. The free bases in Table F-10 were prepared by analogy to compound A55 (compound A55 is the free base of compound B15).

TABLE F-10

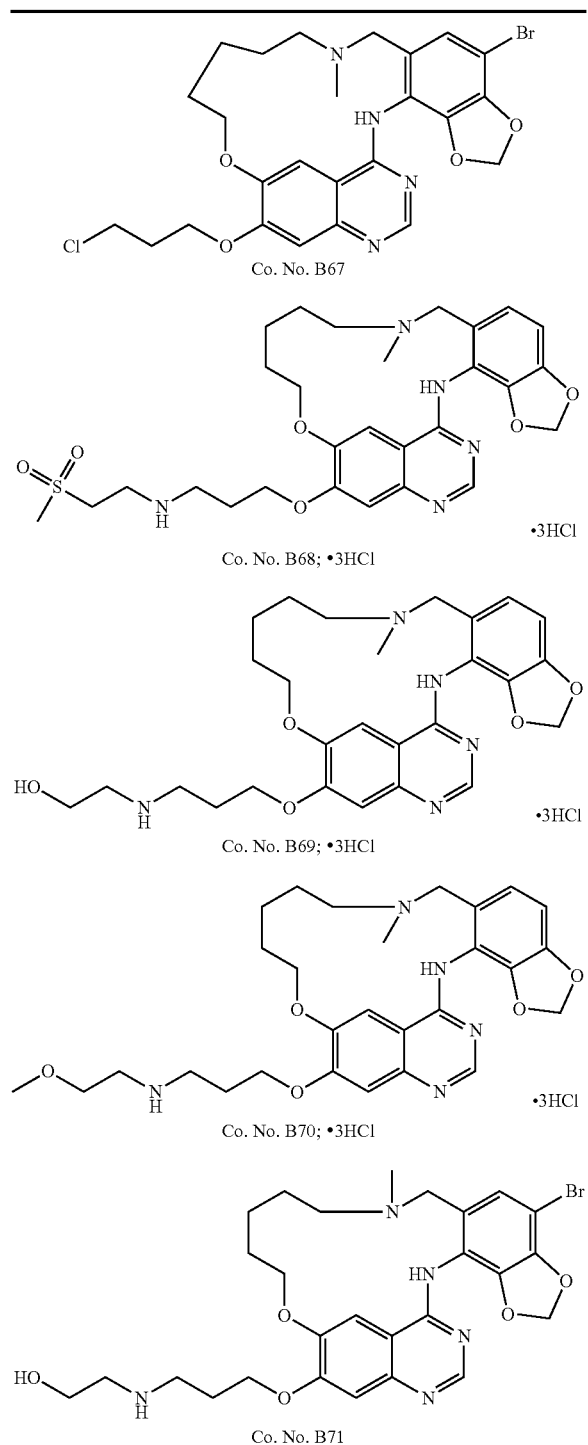

TABLE F-10-continued

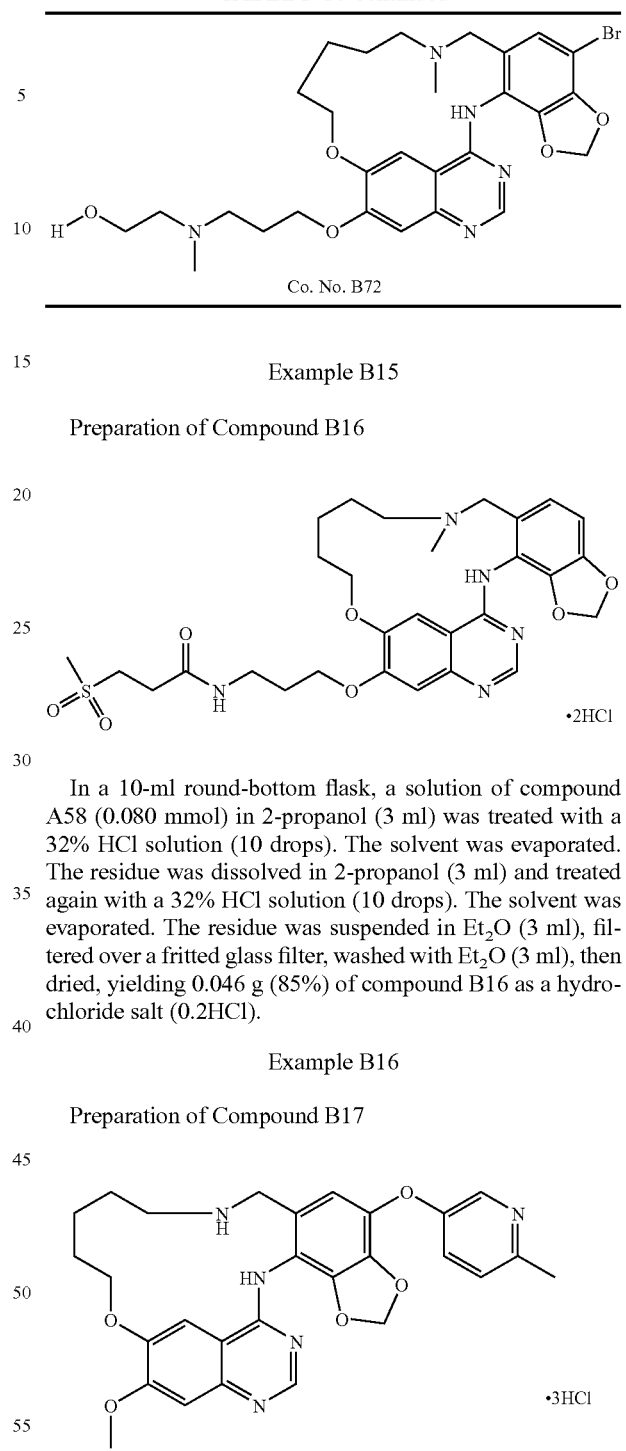

Example B15

Preparation of Compound B16

In a 10-ml round-bottom flask, a solution of compound A58 (0.080 mmol) in 2-propanol (3 ml) was treated with a 32% HCl solution (10 drops). The solvent was evaporated. The residue was dissolved in 2-propanol (3 ml) and treated again with a 32% HCl solution (10 drops). The solvent was evaporated. The residue was suspended in Et₂O (3 ml), filtered over a fritted glass filter, washed with Et₂O (3 ml), then dried, yielding 0.046 g (85%) of compound B16 as a hydrochloride salt (0.2HCl).

Example B16

Preparation of Compound B17

A mixture of compound A68 (0.32 mmol) in CH₃OH (11.2 ml) and CH₂Cl₂ (1.6 ml) was hydrogenated with 10% Pd/C (0.190 g) as a catalyst. After uptake of H₂ (1 equiv), the catalyst was filtered through a pad of Na₂SO₄ and Celite, and the filtrate was evaporated under reduced pressure. The residue was purified by short column chromatography over silica gel (eluent: CH₂Cl₂/CH₃OH from 100/0, over 99/1, 98/2 and 97/3 to 95/5). The product fractions were collected and the solvent was evaporated. The residue (0.074 g) was suspended in 2-propanol (15 ml). Ten drops of a 32% HCl solution were added to obtain a homogeneous solution. The solvent was evaporated. The solid was suspended in 2-propanol again and the suspension was treated with a 32% HCl solution. The solvent was evaporated under reduced pressure. Et₂O was added and the mixture was subjected to ultrasonic conditions. The solvent was evaporated. The residue was taken up into Et₂O, then filtered off, resuspended in Et₂O (×3), filtered off and dried under reduced pressure overnight, yielding 0.0785 g of compound B17 as a hydrochloride salt (0.3HCl).

Example B17

Preparation of Compund B30

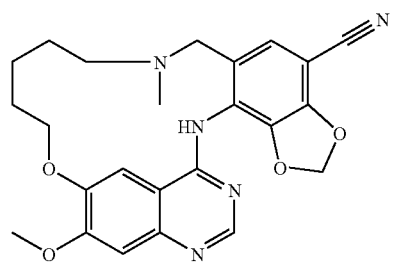 [SMILES: COc1cc2ncnc3c2cc1OCCCCCN(C)Cc1cc(C#N)c2c(c1N3)OCO2]

A mixture of compound B82 (0.080 g, 0.00016 mol), zinc cyanide (Zn(CN)₂) (0.017 g, 0.000145 mol), Zn (0.002 g, powder), DPPF (1,1'-bis(diphenylphosphino)ferrocene) (0.017 g, 0.000031 mol) and tris(dibenzylideneacetone)dipalladium (Pd₂(dba)₃) (0.017 g, 0.000016 mol) was dried in vacuo for 5 minutes and treated under argon with dry, degassed DMA (2.5 ml; absolute). The reaction mixture was stirred for 1 minute and then the mixture was heated in a microwave device for 30 minutes to 150° C. The residue was partitioned between EtOAc and a half-saturated aqueous NaHCO₃ solution. The organic layer was separated, washed with H₂O and brine, dried (Na₂SO₄), filtered and the solvent was evaporated. The residue (brown powder; 0.098 g) was suspended in CH₃OH/Et₂O 1/1 (2 ml) and filtered. The solid was washed first with CH₃OH/Et₂O and then with Et₂O, and was then dried in vacuo. Yield: 0.055 g of compound B30 (77%).

The following compounds were prepared by analogy to the procedure described in Example A5 h)

TABLE F-11

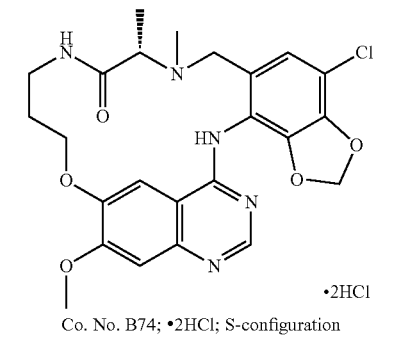

Co. No. B74; •2HCl; S-configuration

TABLE F-11-continued

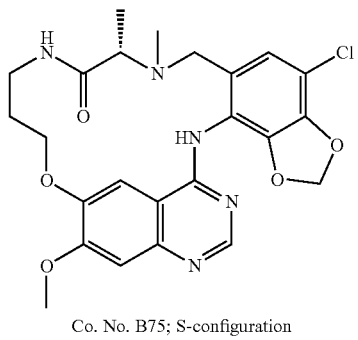

Co. No. B75; S-configuration

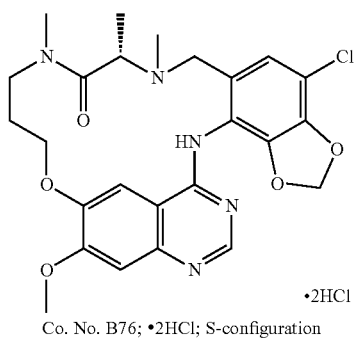

Co. No. B76; •2HCl; S-configuration

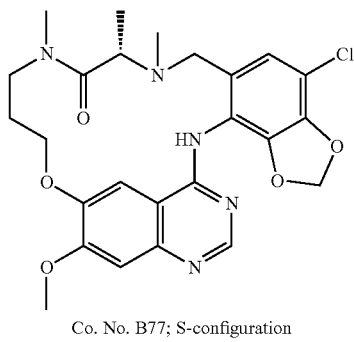

Co. No. B77; S-configuration

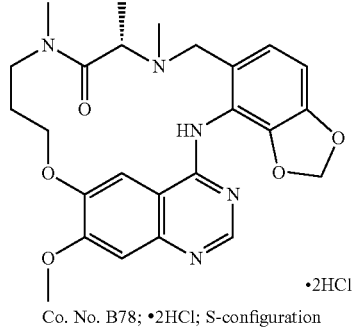

Co. No. B78; •2HCl; S-configuration

TABLE F-11-continued

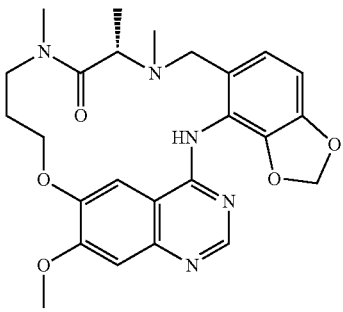 [SMILES: COc1cc2ncnc3c2cc1OCCCN(C)C(=O)[C@H](C)N(C)Cc1ccc2c(c1N3)OCO2]

Co. No. B79; S-configuration

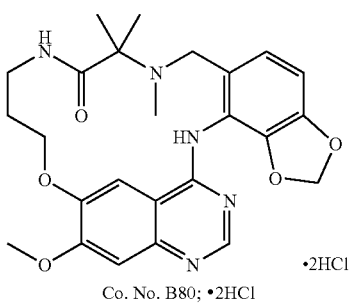

Co. No. B80; •2HCl

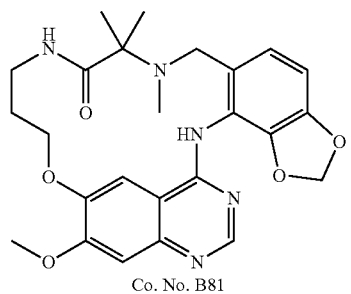

Co. No. B81

B. Compound Identification
LCMS-Methods:
General Procedure A:

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure B:

The HPLC measurement was performed using Alliance HT 2795 (Waters) system comprising a quaternary pump with degasser, an autosampler, a diode-array detector (DAD) and a column as specified in the respective methods below. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters—for methods 6 and 7), and 3.15 kV at 110° C. on the ZQ™ (simple quadrupole Zspray™ mass spectrometer from Waters—for method 8). Nitrogen was used as the nebulizer gas. Data acquisition was performed with a Waters-Micromass Mass-Lynx-Openlynx data system.

General Procedure C:

The HPLC measurement was performed using a system comprising a Dionex P580LPG quaternary gradient pump, a TSP (Thermo Separation)- or Gilson ASPEC auto sampler, a Dionex UVD340S diode-array detector (DAD) or a TSP dual wavelengths UV-detector and a column as specified in the respective methods below. The column temperature was room temperature. The chromatograpy data system was Chromeleon Vs. 6.60 or higher.

Mass detection was done by Flow injection analysis (FIA) (e.g. MeOH, 0.2% formic acid) on a Thermo Finnigan AQA™ or Thermo Finnigan MSQ™ plus mass spectrometer. Ionisation was APCI+ (atmospheric pressure chemical ionization).

Typically, measurements were done at 3-4 cone voltages simultaneously. The cone voltage was modified during the measurement in short intervals e.g. for Thermo Finnigan AQA™ at 5, 15 and 30 V and e.g. for the Thermo Finnigan MSQ™ plus at 40, 50 and 70 V, alternating within ca. 0.3 seconds. The APCI probe temperature was 350° C. Mass spectra were acquired by scanning from 100 to 800 within 2.5 seconds. Nitrogen was used as the nebulizer gas.

General Procedure D:

The HPLC measurement was performed using an Agilent 1100 series liquid chromatography system comprising a binary pump with degasser, an autosampler, a column oven, a UV detector and a column as specified in the respective methods below. Flow from the column was split to a MS spectrometer. The MS detector was configured with an electrospray ionization source. The capillary voltage was 3 kV, the quadrupole temperature was maintained at 100° C. and the desolvation temperature was 300° C. Nitrogen was used as the nebulizer gas. Data acquisition was performed with an Agilent Chemstation data system.

General Procedure E:

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

Method 1:

In addition to general procedure C: Reversed phase HPLC was carried out on a Develosil RPAq column (4.6×50 mm) with a flow rate of 1.5 ml/min. UV-detection at 220 nm and 254 nm. A linear gradient run was employed from 5% acetonitrile and 95% water (0.1% TFA; TFA is defined as trifluoroacetic acid) to 100% acetonitrile in 5 minutes and hold for 1 minute.

Method 2:

In addition to general procedure C: Reversed phase HPLC was carried out on a Develosil RPAq column (4.6×50 mm) with a flow rate of 1.5 ml/min. UV-detection at 220 nm and 254 nm. A linear gradient run was employed from 10% acetonitrile and 90% water (0.1% TFA) to 100% acetonitrile in 5 minutes and hold for 1 minute.

Method 3:

In addition to general procedure C: Reversed phase HPLC was carried out on a Develosil RPAq column (4.6×50 mm) with a flow rate of 1.5 ml/min. UV-detection at 220 nm and 254 nm. A linear gradient run was employed from 40% acetonitrile and 60% water (0.1% TFA) to 100% acetonitrile in 5 minutes and hold for 1 minute.

Method 4:

In addition to general procedure D: Reversed phase HPLC was carried out on a YMC-Pack ODS-AQ C18 column (4.6×50 mm) with a flow rate of 2.6 ml/min. A gradient run was used from 95% water and 5% acetonitrile to 95% acetonitrile in 4.80 minutes and was hold for 1.20 minutes. Mass spectra were acquired by scanning from 100 to 1400. Injection volume was 10 µl. Column temperature was 35° C.

Method 5:

In addition to general procedure D: Reversed phase HPLC was carried out on a YMC-Pack ODS-AQ C18 column (4.6×50 mm) with a flow rate of 2.6 ml/min. A gradient run was used from 88% water and 12% acetonitrile to 88% acetonitrile in 3.40 minutes and was hold for 1.20 minutes. Mass spectra were acquired by scanning from 110 to 1000. Injection volume was 10 µl. Column temperature was 35° C.

Method 6:

In addition to general procedure B: Reversed phase HPLC was carried out on a Xterra-RP C18 column (5 µm, 3.9×150 mm) with a flow rate of 1.0 ml/min at a temperature of 30° C. Two mobile phases (mobile phase A: 100% 7 mM ammonium acetate; mobile phase B: 100% acetonitrile; were employed to run a gradient condition from 85% A, 15% B (hold for 3 minutes) to 20% A, 80% B in 5 minutes, hold at 20% A and 80% B for 6 minutes and reequilibrated with initial conditions for 3 minutes. An injection volume of 20 µl was used. Cone voltage was 20 V for positive ionization mode and 20 V for negative ionization mode. Mass spectra were acquired by scanning from 100 to 900 in 0.8 seconds using an interscan delay of 0.08 seconds.

Method 7:

In addition to general procedure B: Reversed phase HPLC was carried out on a Xterra-RPC18 column (5 µm, 3.9×150 mm) with a flow rate of 1.0 ml/min at a temperature of 30° C. Two mobile phases (mobile phase A: 100% 7 mM ammonium acetate; mobile phase B: 100% acetonitrile; were employed to run a gradient condition from 85% A, 15% B (hold for 3 minutes) to 20% A, 80% B in 5 minutes, hold at 20% A and 80% B for 6 minutes and reequilibrated with initial conditions for 3 minutes. An injection volume of 20 µl was used. Cone voltage was 5 V for positive ionization mode. Mass spectra were acquired by scanning from 100 to 900 in 0.8 seconds using an interscan delay of 0.08 seconds.

Method 8:

In addition to general procedure B: Reversed phase HPLC was carried out on a Xterra-RP C18 column (5 µm, 3.9×150 mm) with a flow rate of 1.0 ml/min at a temperature of 30° C. Two mobile phases (mobile phase A: 100% 7 mM ammonium acetate; mobile phase B: 100% acetonitrile; were employed to run a gradient condition from 85% A, 15% B (hold for 3 minutes) to 20% A, 80% B in 5 minutes, hold at 20% A and 80% B for 6 minutes and reequilibrated with initial conditions for 3 minutes. An injection volume of 20 µl was used. Cone voltage was 20 V for positive and negative ionization mode. Mass spectra were acquired by scanning from 100 to 1000 in 0.4 seconds using an interscan delay of 0.3 seconds.

Method 9:

In addition to general procedure A: Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 0.9 minutes, to 100% B in 0.3 minutes and hold for 0.2 minutes. An injection volume of 2 µl was used. Cone voltage was 10 V for positive ionization mode and 20 V for negative ionization mode.

Method 10:

In addition general procedure C: Reversed phase HPLC was carried out on a Develosil RPAq column (4.6×50 mm) with a flow rate of 1.5 ml/min. UV-detection at 220 nm and 254 nm. A linear gradient run was employed from 20% acetonitrile and 80% water (0.1% TFA) to 100% acetonitrile in 5 minutes and hold for 1 minute.

Method 11:

In addition general procedure C: Reversed phase HPLC was carried out on a Develosil RPAq column (4.6×50 mm) with a flow rate of 1.5 ml/min. UV-detection at 220 nm and 254 nm. A linear gradient run was employed from 15% acetonitrile and 85% water (0.1% TFA) to 100% acetonitrile in 5 minutes and hold for 1 minute.

Method 12:

In addition general procedure E: Reversed phase HPLC (Ultra Performance Liquid Chromatography) was carried out on a bridged ethylsiloxane/silica (BEH) C18 column (1.7 µm, 2.1×50 mm) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 µl was used. Cone voltage was 10 V for positive ionization mode and 20 V for negative ionization mode.

Method 13:

In addition to general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

Melting Points:

For a number of compounds, melting points were obtained with a Kofler hot bench, consisting of a heated plate with linear temperature gradient, a sliding pointer and a temperature scale in degrees Celsius. Values were obtained with experimental uncertainties that are commonly associated with this analytical method.

For a number of compounds, melting points were obtained with a Büchi melting point apparatus B-540 or B-545 (in open capillary tubes). The heating medium was a metal block. The melting of the sample was visually observed by a magnifying lense and a big light contrast. Melting points were measured with a temperature gradient of either 3 or 10° C./minute. Maximum temperature was 300° C. Values were obtained with experimental uncertainties that are commonly associated with this analytical method.

TABLE retention time (Rt in minutes), MH+ peak, melting point and stereochemistry data.

| Comp. No. | Rt | MW (MH+) | LC/GC/MS Method | Melting point (° C.) | Stereo-chemistry |
|---|---|---|---|---|---|
| A10 | 0.87 | 409 | 9 | | |
|  | 2.70 | 409 | 2 | | |
| A11 | 1.01 | 423 | 9 | | |
|  | 3.04 | 423 | 1 | | |
| A12 | 0.95 | 409 | 9 | | |
|  | 1.22 | 409 | 1 | | |
| B31 | 1.01 | 511 | 9 | | |
| B1 | 2.80 | 550 | 1 | | S |
| B2 | 1.52 | 467 | 1 | | |
|  | 1.01 | 467 | 9 | | |
| B18 | 1.04 | 536 | 9 | | |
| B19 | 1.01 | 534 | 9 | | |
| B20 | 2.94 | 520 | 1 | | |
|  | 0.57 | 520 | 12 | | |
| B12 | 1.05 | 549 | 9 | | |
| B22 | 1.05 | 520 | 9 | | |
| B13 | 0.96 | 579 | 9 | | |
|  | 2.78 | 579 | 1 | | |
| B68 | 0.95 | 572 | 9 | | |
| B16 | 0.94 | 600 | 9 | | |
| B69 | 0.89 | 510 | 9 | | |
| B15 | 0.94 | 524 | 9 | | |
| B70 | 0.96 | 524 | 9 | | |
| B23 | 0.99 | 584 | 9 | | |
| B65 | 1.01 | 654 | 9 | | |
| B24 | 0.93 | 600 | 9 | | S |
| B25 | 0.94 | 600 | 9 | | R |
| A57 | 2.77 | 466 | 1 | | |
| B17 | 0.94 | 516 | 9 | | |
| B43 | 1.08 | 501 | 9 | | |
| B8 | 3.23 | 487 | 1 | | |
|  | 0.80 | 487 | 12 | | |
| A22 | 2.69 | 438 | 2 | | |
|  | 0.57 | 438 | 12 | | |
| B9 | 2.62 | 452 | 2 | | |
| B10 | 2.61 | 452 | 2 | | |
|  | 0.84 | 452 | 12 | | |
| A38 | 2.87 | 466 | 1 | | S |
|  | 0.61 | 466 | 12 | | |
| B30 | 3.25 | 448 | 1 | | |
| A8 | 2.05 | 543 | 5 | | |
|  | 3.66 | 543 | 11 | | |
|  | 1.16 | 543 | 12 | | |
| B44 | 8.44 | 473 | 6 | | |
| B45 | 0.84 | 395 | 9 | | |
| B46 | 1.17 | 395 | 4 | | |
| A23 | 2.57 | 424 | 2 | | |
| B11 | 2.58 | 424 | 2 | | |
|  | 0.49 | 424 | 12 | | |
| A20 | 3.32 | 623 | 2 | | |
|  | 0.93 | 623 | 12 | | |
| B34 | 2.85 | 551 | 1 | | |
|  | 5.09 | 551 | 13 | | |
| A24 | 2.98 | 524 | 2 | | |
|  | 0.89 | 524 | 12 | | |
| A40 | 2.78 | 452 | 1 | | S |
|  | 0.54 | 452 | 12 | | |
| A27 | 3.99 | 664 | 1 | | |
| A29 | 4.09 | 639 | 1 | | |
|  | 0.74 | 639 | 12 | | |
| A28 | 3.48 | 626 | 3 | | |
| B5 | 2.44 | 539 | 2 | | |
|  | 4.08 | 539 | 13 | | |
| B3 | 2.41 | 564 | 2 | | |
|  | 0.46 | 564 | 12 | | |
| B35 | 2.54 | 539 | 2 | | |
|  | 0.48 | 539 | 12 | | |
| B4 | 2.79 | 526 | 2 | | |
|  | 0.66 | 526 | 12 | | |
| A54 | 3.02 | 727 | 2 | | |
| B14 | 2.92 | 627 | 1 | | |
|  | 4.83 | 627 | 13 | | |
| A42 | 0.79 | 579 | 9 | | |
|  | 2.60 | 579 | 1 | | |
|  | 0.47 | 579 | 12 | | |
| B6 | 2.71 | 579 | 1 | | |
|  | 0.47 | 579 | 12 | | |
| B32 | 3.33 | 539 | 2 | | |
|  | 0.98 | 539 | 12 | | |
| A68 | 0.98 | 650 | 9 | | |
| B54 | 2.53 | 622 | 1 | | S |
|  | 0.47 | 622 | 12 | | |
| B55 | 2.69 | 683 | 1 | | S |
|  | 0.51 | 683 | 12 | | |
| B38 | 2.64 | 567 | 1 | | S |
|  | 0.51 | 567 | 12 | | |
| B39 | 3.96 | 553 | 2 | | S |
| B40 | 2.70 | 567 | 1 | | S |
|  | 0.46 | 567 | 12 | | |
| B56 | 2.66 | 655 | 1 | | S |
|  | 0.48 | 655 | 12 | | |
| B41 | 2.80 | 510 | 1 | | S |
|  | 0.66 | 510 | 12 | | |
| A43 | 2.97 | 554 | 1 | | S |
| B7 | 2.86 | 554 | 1 | | S |
| B42 | 2.90 | 508 | 1 | | S, S |
|  | 0.62 | 508 | 12 | | |
| B27 | 8.03 | 584 | 6 | 224 | |
| B47 | 7.16 | 409 | 6 | 250 | |
| B48 | 9.17 | 487 | 6 | | |
| B71 | 8.10 | 588 | 6 | 241 | |
| B58 | 2.52 | 592 | 1 | | S |
|  | 0.48 | 592 | 12 | | |
| B57 | 2.68 | 592 | 1 | | S |
| B59 | 2.63 | 712 | 1 | | S |
|  | 0.47 | 712 | 12 | | |
| B61 | 2.58 | 663 | 1 | | S |
| B60 | 2.57 | 663 | 1 | | S |
| B37 | 2.76 | 627 | 1 | | S |
| B36 | 2.63 | 627 | 1 | | S |
|  | 0.61 | 627 | 12 | | |
| B63 | 2.61 | 609 | 1 | | S, S |
| B62 | 2.51 | 609 | 1 | | S, S |
|  | 0.45 | 609 | 12 | | |
| B74 | 3.05 | 500 | 1 | | S |
|  | 0.80 | 500 | 12 | | |
| B77 | 3.03 | 514 | 1 | | S |
| B76 | 0.89 | 514 | 9 | | S |
| B33 | 1.18 | 453 | 5 | | |
| B66 | 8.24 | 657 | 6 | | |
| B28 | 7.86 | 613 | 6 | 244 | |
| B72 | 8.19 | 602 | 6 | | |
| B49 | 8.80 | 395 | 6 | | |
| B78 | 0.82 | 480 | 9 | | S |
| B79 | 2.90 | 480 | 1 | | S |
| B81 | n.d. | 480 | n.d. | | |
| B80 | 2.74 | 480 | 1 | | |
| B50 | 3.72 | 543 | 2 | | |
|  | 1.11 | 543 | 12 | | |
| B51 | 2.80 | 409 | 1 | | |
| B52 | 2.66 | 423 | 1 | | |
|  | 0.47 | 423 | 12 | | |
| B53 | 0.76 | 423 | 9 | | | n.d.: not determined

C. Pharmacological Examples

The in vitro inhibition of c-Src kinase was assessed using the glass-fiber filter technology as described by Davies, S. P. et al., *Biochem J.* (2000), 351; p. 95-105.

In the glass-fiber filter technology the activity of the kinase is measured using an appropriate substrate that is incubated with the aforementioned kinase protein in the presence of ($^{33}$P) radiolabeled ATP. ($^{33}$P) Phosporylation of the substrate is subsequently measured as radioactivity bound on a glass-fiber-filter.

C1: c-Src Filter Assay

In an alternative filter based assay the final kinase activity was assessed using a phosphostorage screen instead of scintilation counting.

In this assay the Src kinase reaction is performed at 25° C. for 10 minutes in a 96-well microtiterplate. The 25 µl reaction volume contains 8 mM MOPS pH 7.0, 20 mM Mg-acetate, 0.2 mM Na$_2$EDTA, 0.5 mM MnCl$_2$, 1.0 µM unlabeled ATP, 0.2 µCi AT$^{33}$P, 20 ng poly(Glu,Tyr) 4:1 and 5 ng human Src.

The reaction is stopped by adding 5 µl of a 3% phosphoric acid solution. 5 µl of the reaction mixture is then spotted onto a Filtermat A filter (Wallac) and washed 3 times for 5 min. in 75 mM phosphoric acid and 1 time for 5 min. in methanol prior to drying and quantification on the Typhoon (Amersham) using a phosphostorage screen.

C2: Fyn Kinase Assay

In this assay the Fyn kinase reaction is performed at 25° C. for 10 minutes in a 96-well microtiterplate. The 25 µl reaction volume contains 8 mM MOPS pH 7.0, 20 mM Mg-acetate, 0.2 mM Na$_2$EDTA, 0.5 mM MnCl$_2$, 1.0 µM unlabeled ATP, 0.2 µCi AT$^{33}$P, 20 ng poly(Glu,Tyr) 4:1 and 5 ng human Fyn.

The reaction is stopped by adding 5 µl of a 3% phosphoric acid solution. 5 µl of the reaction mixture is then spotted onto a Filtermat A filter (Wallac) and washed 3 times for 5 min. in 75 mM phosphoric acid and 1 time for 5 min. in methanol prior to drying and scintillation counting.

The following tables provides the pIC50 values for the compounds according to the invention.

| Comp. No. | C1: c-SRC filter pIC50 | C2: Fyn kinase pIC50 | Comp. No. | C1: c-SRC filter pIC50 | C2: Fyn kinase pIC50 |
| --- | --- | --- | --- | --- | --- |
| A9 | 5.64 | >6 | B5 | 6.30 | 7.68 |
| A10 | 5.59 | >6 | B3 | 6.35 | 7.93 |
| A11 | n.d. | 7.74 | B35 | 6.20 | 7.53 |
| A12 | <5 | 7.46 | B4 | 5.83 | 7.63 |
| B31 | 5.58 | >9 | A54 | n.d. | 7.16 |
| B18 | 6.33 | >9 | B14 | n.d. | 7.71 |
| B19 | 6.21 | 8.91 | A25 | n.d. | <6 |
| B21 | 6.24 | 10.24 | A42 | n.d. | 7.19 |
| B1 | 6.27 | >9 | B6 | n.d. | 7.42 |
| B12 | 6.58 | 9.56 | B32 | n.d. | 7.42 |
| B2 | 5.96 | 8.11 | A68 | n.d. | <6 |
| B22 | 5.89 | <6 | B54 | n.d. | 7.29 |
| B73 | <5 | 7.55 | B55 | n.d. | 6.94 |
| B13 | 6.53 | 8.44 | B38 | n.d. | 6.86 |
| B68 | 6.16 | >6 | B39 | n.d. | 6.89 |
| B16 | 5.64 | >6 | B40 | n.d. | 6.67 |
| B69 | 6.32 | 8.21 | B56 | n.d. | 7.07 |
| B15 | 6.25 | 9.76 | B41 | n.d. | 7.09 |
| B70 | 6.11 | 8.30 | B7 | n.d. | 7.04 |
| B23 | 6.15 | >6 | B42 | n.d. | 6.55 |
| B65 | 5.74 | 8.24 | B27 | n.d. | >6 |
| B24 | 6.17 | >6 | B47 | n.d. | 6.92 |
| B25 | 5.85 | 8.28 | B48 | n.d. | 7.05 |
| A56 | <5 | >6 | B57 | n.d. | 7.58 |
| A57 | 6.03 | 7.74 | B58 | n.d. | 7.48 |
| B17 | <5 | 7.39 | B59 | n.d. | 7.37 |
| B43 | <5 | 7.71 | B60 | n.d. | 7.43 |
| B8 | 5.19 | 7.78 | B36 | n.d. | 7.42 |
| A22 | 5.49 | 7.40 | B62 | n.d. | 6.70 |
| B10 | 5.72 | 7.66 | B74 | n.d. | 7.16 |
| A38 | 5.48 | 6.61 | B76 | n.d. | 6.50 |
| A8 | n.d. | 6.69 | B33 | n.d. | 7.88 |
| B44 | n.d. | 6.68 | B66 | n.d. | >6 |
| A23 | <5 | <6 | B28 | n.d. | >6 |
| B11 | <5 | <6 | B72 | n.d. | >6 |
| A20 | 6.73 | 8.16 | B78 | n.d. | <6 |

-continued

| Comp. No. | C1: c-SRC filter pIC50 | C2: Fyn kinase pIC50 | Comp. No. | C1: c-SRC filter pIC50 | C2: Fyn kinase pIC50 |
| --- | --- | --- | --- | --- | --- |
| B34 | 6.37 | >6 | B50 | n.d. | <6 |
| A24 | <5 | <6 | B52 | n.d. | 6.89 |
| A40 | <5 | <6 | B53 | n.d. | 6.96 |
| A27 | 5.65 | 7.65 | | | |
| A29 | 5.58 | 7.36 | | | |
| A28 | <5 | >6 | | | | n.d.: not determined

D. Composition Examples

The following formulations exemplify typical pharmaceutical compositions suitable for systemic administration to animal and human subjects in accordance with the present invention.

"Active ingredient" (A.I.) as used throughout these examples relates to a compound of formula (I) or a pharmaceutically acceptable addition salt thereof.

Example D.1

Film-Coated Tablets

Preparation of Tablet-Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) was added a solution of ethyl cellulose (5 g) in DCM (150 ml). Then there were added DCM (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

The invention claimed is:

1. A compound having the formula

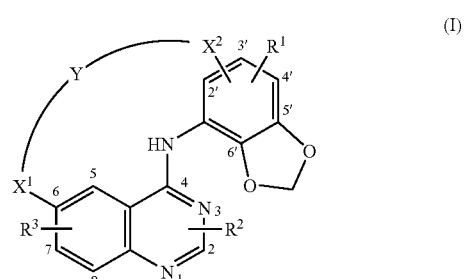

N-oxide forms, pharmaceutically acceptable addition salts or stereochemically isomeric forms thereof, wherein Y represents —$C_{3-9}$alkyl-, —$C_{1-5}$alkyl-O—$C_{1-5}$alkyl-, —$C_{1-5}$alkyl-NR$^6$—$C_{1-5}$alkyl-, or —$C_{1-5}$alkyl-NR$^7$—CO—$C_{1-5}$alkyl-;

$X^1$ represents —O—;

$X^2$ represents —NR$^5$—$C_{1-2}$alkyl-, wherein $X^2$ is attached at position 2';

$R^1$ represents hydrogen, cyano, halo, hydroxy, $C_{1-4}$alkyl, Het$^3$, Ar$^1$, Het$^3$-O— or Ar$^1$—O—;

$R^2$ represents hydrogen, cyano, halo, $C_{2-6}$alkenyl, $C_{2-6}$alkynyl, $C_{3-7}$cycloalkyl or $C_{1-6}$alkyl wherein said $C_{2-6}$alkenyl, $C_{2-6}$alkynyl, $C_{3-7}$cycloalkyl or $C_{1-6}$alkyl are optionally substituted with one or where possible two or more substituents selected from hydroxy or halo $R^3$ represents hydroxy; $C_{1-4}$alkyloxy; or $C_{1-4}$alkyloxy-substituted with one or where possible two or more substituents each independently selected from Het$^4$, hydroxy, $C_{1-4}$alkyloxy-, halo, NR$^9$R$^{10}$, $C_{1-4}$alkyl-O—C(=O)—O—, Ar$^2$, NR$^{11}$R$^{12}$-carbonyl, Het$^5$-carbonyl and oxiranyl;

$R^4$ represents hydrogen, Ar$^3$—S(=O)$_2$—, Ar$^3$—S(=O)—, $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- wherein said $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- is optionally substituted with $C_{1-4}$alkyloxy-, Het$^6$ or phenyl;

$R^5$ represents hydrogen, $C_{1-4}$alkyl, or $C_{1-4}$alkyloxycarbonyl- wherein said $C_{1-4}$alkyl or $C_{1-4}$alkyloxycarbonyl- is optionally substituted with $C_{1-4}$alkyloxy-, Het$^6$ or phenyl;

$R^6$ represents hydrogen or $C_{1-4}$alkyl;

$R^7$ represents hydrogen or $C_{1-4}$alkyl;

$R^8$ represents hydrogen, Ar$^5$—S(=O)$_2$—, Ar$^5$—S(=O)—, $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- wherein said $C_{1-4}$alkyl, $C_{2-4}$alkenyl, $C_{3-7}$cycloalkyl, $C_{2-4}$alkynyl, $C_{1-4}$alkylcarbonyl or $C_{1-4}$alkyloxycarbonyl- is optionally substituted with $C_{1-4}$alkyloxy-, Het$^8$ or phenyl;

$R^9$ and $R^{10}$ each independently represent hydrogen; Het$^9$; Het$^{11}$-S(=O)$_2$; $C_{1-4}$alkyl or $C_{1-4}$alkyl substituted with one or where possible two or more substituents selected from hydroxy, $C_{1-4}$alkyloxy, $C_{1-4}$alkyl-S(=O)$_2$, halo, Het$^{10}$, $C_{1-4}$alkyl-C(=O)—NR$^{13}$—, $C_{1-4}$alkyl-S(=O)$_2$—NR$^{14}$—, amino-C(=O)—NR$^{15}$, mono- or di($C_{1-4}$alkyl)amino-C(=O)—NR$^{16}$—, aminocarbonyl, aminocarbonyloxy, mono- or di($C_{1-4}$alkyl)aminocarbonyl, mono- or di($C_{1-4}$alkyl)aminocarbonyloxy, Het$^{12}$-oxycarbonyl, $C_{1-4}$alkyloxy-$C_{1-4}$alkyloxy-, Het$^{13}$-carbonyl or $C_{1-4}$alkyl-S(=O)$_2$—$C_{1-4}$alkyl-NR$^{17}$—C(=O)—;

$R^{11}$ and $R^{12}$ each independently represent hydrogen; $C_{1-4}$alkyl or $C_{1-4}$alkyl substituted with one or where possible two or more substituents selected from hydroxy, $C_{1-4}$alkyloxy or $C_{1-4}$alkyl-S(=O)$_2$—;

$R^{13}$ represents hydrogen or $C_{1-4}$alkyl;

$R^{14}$ represents hydrogen or $C_{1-4}$alkyl;

$R^{15}$, $R^{16}$ and $R^{17}$ each independently represent hydrogen or $C_{1-4}$alkyl;

$R^{18}$ and $R^{19}$ each independently represent hydrogen; $C_{1-4}$alkyl or $C_{1-4}$alkyl substituted with one or where possible two or more substituents selected from hydroxy, $C_{1-4}$alkyloxy or $C_{1-4}$alkyl-S(=O)$_2$—;

Het$^1$ represents pyrrolidinyl, 2-pyrrolidinonyl or piperidinyl wherein said Het$^1$ is optionally substituted with one or where possible two or more substituents selected from hydroxy, $C_{1-4}$alkyl, $C_{1-4}$alkyloxy or $C_{1-4}$alkyloxycarbonyl;

Het$^2$ represents pyrrolidinyl, 2-pyrrolidinonyl or piperidinyl wherein said Het$^2$ is optionally substituted with one or where possible two or more substituents selected from hydroxy, $C_{1-4}$alkyl, $C_{1-4}$alkyloxy or $C_{1-4}$alkyloxycarbonyl;

Het$^3$ represents morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said Het$^3$ is optionally substituted with one or where possible two or more substituents selected from hydroxy, $C_{1-4}$alkyl, $C_{1-4}$alkyloxy- or $C_{1-4}$alkylsulfonyl;

Het$^4$ represents morpholinyl, piperidinyl, pyrrolidinyl, 1,1-dioxothiomorpholinyl, piperazinyl, furanyl, thiomorpholinyl, imidazolyl or pyrazolidinyl wherein said Het$^4$ is optionally substituted with one or where possible two or more substituents selected from hydroxy; $C_{1-4}$alkyl; amino; mono- or di($C_{1-4}$alkyl)amino; $C_{1-4}$alkyl-S(=O)$_2$—; $C_{1-4}$alkyl substituted with one or where possible two or more substituents selected from hydroxy, $C_{1-4}$alkyl-C(=O)—NH—, $C_{1-4}$alkyl-S(=O)$_2$—, amino, mono- or di($C_{1-4}$alkyl)aminocarbonyl, NR$^{18}$R$^{19}$, aminocarbonyl, $C_{1-4}$alkyloxy and mono- or di($C_{1-4}$alkyl)aminocarbonyl; $C_{1-4}$alkyl-C(=O)— optionally substituted with one or where possible two or more substituents selected from hydroxy, $C_{1-4}$alkyloxy and $C_{1-4}$alkylsulfonyl; or with $C_{1-4}$alkyloxycarbonyl optionally substituted with one or where possible two or more substituents selected from hydroxy, $C_{1-4}$alkyloxy and $C_{1-4}$alkylsulfonyl;

Het$^5$ represents morpholinyl, piperidinyl, pyrrolidinyl, 1,1-dioxothiomorpholinyl, piperazinyl or thiomorpholinyl wherein said Het$^5$ is optionally substituted with one or where possible two or more substituents selected from $C_{1-4}$alkyl; hydroxy; amino; mono- or di($C_{1-4}$alkyl)amino;

$C_{1-4}$alkyl-S(=O)$_2$; and $C_{1-4}$alkyl substituted with one or where possible two or more substituents selected from hydroxy, $C_{1-4}$alkyl-C(=O)—NH— and $C_{1-4}$alkyl-S(=O)$_2$—;

Het$^6$, Het$^7$ and Het$^8$ each independently represent morpholinyl, piperazinyl, piperidinyl or pyrrolidinyl wherein said Het$^6$, Het$^7$ and Het$^8$ are optionally substituted with one or more substituents selected from hydroxy, amino, $C_{1-4}$alkyl and $C_{1-4}$alkyl substituted with one or where possible two or more substituents selected from hydroxy, halo, and $C_{1-4}$alkyloxy-;

Het$^9$ and Het$^{10}$ each independently represent morpholinyl, piperidinyl, pyrrolidinyl, 1,1-dioxothiomorpholinyl, piperazinyl or thiomorpholinyl wherein said Het$^9$ and Het$^{10}$ are optionally substituted with one or where possible two or more substituents selected from $C_{1-4}$alkyl; hydroxy; amino; mono- or di($C_{1-4}$alkyl)amino; $C_{1-4}$alkyl-S(=O)$_2$; and $C_{1-4}$alkyl substituted with one or where possible two or more substituents selected from hydroxy, $C_{1-4}$alkyl-C(=O)—NH— and $C_{1-4}$alkyl-S(=O)$_2$—;

Het$^{11}$, Het$^{12}$ and Het$^{13}$ each independently represent morpholinyl, piperazinyl, piperidinyl or pyrrolidinyl wherein said Het$^{11}$, Het$^{12}$ and Het$^{13}$ are optionally substituted with one or more substituents selected from hydroxy, amino, $C_{1-4}$alkyl and $C_{1-4}$alkyl substituted with one or where possible two or more substituents selected from hydroxy, halo, and $C_{1-4}$alkyloxy-;

$Ar^1$ and $Ar^2$ each independently represent phenyl optionally substituted with nitro, cyano, hydroxy, $C_{1-4}$alkyl, $C_{1-4}$alkyloxy- or amino;

$Ar^3$, $Ar^4$ and $Ar^5$ each independently represent phenyl optionally substituted with nitro, cyano, hydroxy, $C_{1-4}$alkyl, $C_{1-4}$alkyloxy- or amino.

2. A compound according to claim 1 wherein;

Y represents —$C_{3-9}$alkyl-, —$C_{1-5}$alkyl-$NR^6$—$C_{1-5}$alkyl-, or —$C_{1-5}$alkyl-$NR^7$—CO—$C_{1-5}$alkyl-;

$X^1$ represents —O—;

$X^2$ represents —$NR^5$—$C_{1-2}$alkyl-, wherein $X^2$ is attached at position 2';

$R^1$ represents hydrogen, cyano, halo, hydroxy, $C_{1-4}$alkyl, $Het^3$, $Het^3$-O— or $Ar^1$—O—;

$R^2$ represents hydrogen;

$R^3$ represents hydroxy; $C_{1-4}$alkyloxy; or $C_{1-4}$alkyloxy-substituted with one or where possible two or more substituents each independently selected from $Het^4$, hydroxy, $C_{1-4}$alkyloxy-, halo, $NR^9R^{10}$, $C_{1-4}$alkyl-O—C(=O)—O— and oxiranyl;

$R^5$ represents hydrogen, $C_{1-4}$alkyl, or $C_{1-4}$alkyloxycarbonyl- wherein said $C_{1-4}$alkyloxycarbonyl- is optionally substituted with phenyl;

$R^6$ represents hydrogen or $C_{1-4}$alkyl;

$R^7$ represents hydrogen or $C_{1-4}$alkyl;

$R^8$ represents hydrogen, $C_{1-4}$alkyl, $Ar^5$—S(=O)$_2$— or $C_{1-4}$alkyloxycarbonyl;

$R^9$ and $R^{10}$ each independently represent hydrogen; $C_{1-4}$alkyl or $C_{1-4}$alkyl substituted with one or where possible two or more substituents selected from hydroxy, $C_{1-4}$alkyloxy, $C_{1-4}$alkyl-S(=O)$_2$, halo, or $C_{1-4}$alkyloxy-$C_{1-4}$alkyloxy-;

$Het^1$ represents pyrrolidinyl or piperidinyl wherein said $Het^1$ is optionally substituted with one or where possible two or more substituents selected from hydroxy, or $C_{1-4}$alkyl;

$Het^2$ represents pyrrolidinyl or piperidinyl wherein said $Het^2$ is optionally substituted with one or where possible two or more substituents selected from hydroxy, or $C_{1-4}$alkyl;

$Het^3$ represents morpholinyl, piperidinyl, piperazinyl or pyrrolidinyl wherein said $Het^3$ is optionally substituted with one or where possible two or more substituents selected from hydroxy or $C_{1-4}$alkyl;

$Het^4$ represents morpholinyl, piperidinyl, pyrrolidinyl, 1,1-dioxothiomorpholinyl, or piperazinyl wherein said $Het^4$ is optionally substituted with one or where possible two or more substituents selected from hydroxy; $C_{1-4}$alkyl; amino;

$C_{1-4}$alkyl-S(=O)$_2$—; $C_{1-4}$alkyl substituted with one or where possible two or more substituents selected from hydroxy and $C_{1-4}$alkyl-C(=O)—NH—;

or with $C_{1-4}$alkyl-C(=O)— optionally substituted with one or where possible two or more substituents selected from hydroxy, $C_{1-4}$alkyloxy and $C_{1-4}$alkylsulfonyl;

$Ar^3$ and $Ar^5$ each independently represent phenyl optionally substituted with nitro, cyano, hydroxy, or $C_{1-4}$alkyloxy-.

3. A compound according to claim 1 wherein;

$R^3$ represents hydroxy; $C_{1-4}$alkyloxy; or $C_{1-4}$alkyloxy-substituted with one or where possible two or more substituents each independently selected from $Het^4$, hydroxy, $C_{1-4}$alkyloxy-, halo, $NR^9R^{10}$, and $C_{1-4}$alkyl-O—C(=O)—O—.

4. A compound according to claim 1 wherein;

Y represents —$C_{3-9}$alkyl-, —$C_{1-5}$alkyl-$NR^6$—$C_{1-5}$alkyl- or —$C_{1-5}$alkyl-$NR^7$—CO—$C_{1-5}$alkyl-;

$X^1$ represents —O—;

$X^2$ represents —$NR^5$—$C_{1-2}$alkyl-, wherein $X^2$ is attached at position 2';

$R^1$ represents hydrogen, halo or $Het^3$-O—;

$R^2$ represents hydrogen;

$R^3$ represents hydroxy, $C_{1-4}$alkyloxy or $C_{1-4}$alkyloxy substituted with one or two substituents each independently selected from $Het^4$, hydroxy, $C_{1-4}$alkyloxy-, $C_{1-4}$alkyloxy-$C_{1-4}$alkyloxy and $NR^9R^{10}$;

$R^5$ represents hydrogen or $C_{1-4}$alkyl;

$R^6$ represents hydrogen or $C_{1-4}$alkyl;

$R^7$ represents hydrogen;

$R^9$ and $R^{10}$ each independently represent hydrogen; $C_{1-4}$alkyl-S(=O)$_2$—$C_{1-4}$alkyl-C(=O)—; $C_{1-4}$alkyl or $C_{1-4}$alkyl substituted with hydroxy;

$Het^3$ represents pyridinyl optionally substituted with $C_{1-4}$alkyl;

$Het^4$ represents morpholinyl, piperidinyl or piperazinyl wherein said $Het^4$ is optionally substituted with hydroxy-$C_{1-4}$alkyl or $C_{1-4}$alkyl-S(=O)$_2$—$C_{1-4}$alkyl-.

5. A compound according to claim 1 wherein;

$X^1$ represents —O—;

$X^2$— represents —$NR^5$—$C_{1-2}$alkyl- or —N($CH_3$)—$C_{1-2}$alkyl-, wherein $X^2$ is attached at position 2';

$R^1$ is fluoro, chloro or bromo;

$R^2$ is cyano;

$R^3$ is at position 7 of the structure of formula (I).

6. A compound according to claim 1 wherein;

$R^3$ represents $C_{1-4}$alkyloxy substituted with hydroxy and one substituent selected from $NR^9R^{10}$ or $Het^4$-.

7. A compound according to claim 1 wherein;

$R^3$ represents $C_{1-4}$alkyloxy substituted with $C_{1-4}$alkyloxy-$C_{1-4}$alkyloxy.

8. A compound according to claim 1 wherein;

$R^3$ represents $C_{1-4}$alkyloxy.

9. A compound according to claim 1 wherein;

$R^9$ is hydrogen or methyl and $R^{10}$ represents $C_{1-4}$alkyl-S(=O)$_2$—$C_{1-4}$alkyl-C(=O)—, $C_{1-4}$alkyl or hydroxy-$C_{1-4}$alkyl.

10. A compound according to claim 1 wherein;

$Het^4$ represents piperidinyl or piperazynil wherein said $Het^4$ is substituted with methyl of hydroxyethyl.

11. A compound according to claim 1 wherein;

the $X^2$ substituent is at position 2', the $R^1$ substituent represents hydrogen or halo and is at position 4', the $R^2$ substituent is at position 2 and the $R^3$ substituent at position 7 of the structure of formula (I).

12. A compound of formula (I) in claim 1 selected from the group consisting of

| | |
|---|---|
| 1-piperidineethanol, alpha-[[(8,9,10,11,12,13,14,20-octahydro-13-methyl-4,6-etheno[1,3]dioxolo[4,5-q]pyrimido[4,5-b][6,1,12]benzoxadiazacyclopentadecin-21-yl)oxy]methyl]-, (alphaS)- | B1 |
| 4,6-etheno[1,3]dioxolo[4,5-q]pyrimido[4,5-b][6,1,12]benzoxadiazacyclopentadecine, 8,9,10,11,12,13,14,20-octahydro-21-(2-methoxyethoxy)-13-methyl- | B2 |
| ethanol, 2-[methyl[3-[(8,9,10,11,12,13,14,20-octahydro-13-methyl-4,6-etheno[1,3]dioxolo[4,5-q]pyrimido[4,5-b][6,1,12]benzoxadiazacyclopentadecin-21-yl)oxy]propyl]amino]- | B15 |
| propanamide, 3-(methylsulfonyl)-N-[3-[(8,9,10,11,12,13,14,20-octahydro-13-methyl-4,6-etheno[1,3]dioxolo[4,5-q]pyrimido[4,5-b][6,1,12]benzoxadiazacyclopentadecin-21-yl)oxy]propyl]- | B16 |

| | |
|---|---|
| 5,7-etheno-1H-[1,3]dioxolo[4,5-r]pyrimido[4,5-b][6,1,10,13]benzoxatriazacyclohexadecine, 9,10,11,12,13,14,15,16-octahydro-15-methyl-22-[3-(4-methyl-1-piperazinyl)propoxy]- | B3 |
| 5,7-etheno-1H-[1,3]dioxolo[4,5-r]pyrimido[4,5-b][6,1,10,13]benzoxatriazacyclohexadecine, 9,10,11,12,13,14,15,16-octahydro-22-[2-(2-methoxyethoxy)ethoxy]-15-methyl- | B4 |
| ethanol, 2-[methyl[3-[(9,10,11,12,13,14,15,16-octahydro-15-methyl-5,7-etheno-1H-[1,3]dioxolo[4,5-r]pyrimido[4,5-b][6,1,10,13]benzoxatriaza-cyclohexadecin-22-yl)oxy]propyl]amino]- | B5 |
| 5,7-etheno-13H-[1,3]dioxolo[4,5-r]pyrimido[4,5-b][6,1,10,13]benzoxatriazacyclohexadecin-13-one, 1,9,10,11,12,14,15,16-octahydro-14,15-dimethyl-22-[3-(4-morpholinyl)propoxy]-, (14S)- | B6 |
| 4,6-etheno[1,3]dioxolo[4,5-q]pyrimido[4,5-b][6,1,12]benzoxadiazacyclopentadecine, 8,9,10,11,12,13,14,20-octahydro-21-methoxy-16-[(6-methyl-3-pyridinyl)oxy]- | B17 |
| 5,7-etheno-13H-[1,3]dioxolo[4,5-r]pyrimido[4,5-b][6,1,10,13]benzoxatriazacyclohexadecin-13-one, 1,9,10,11,12,14,15,16-octahydro-22-[2-(2-methoxyethoxy)ethoxy]-14,15-dimethyl-, (14S)- | B7 |
| 4,6-etheno[1,3]dioxolo[4,5-q]pyrimido[4,5-b][6,1,12]benzoxadiazacyclopentadecine, 16-bromo-8,9,10,11,12,13,14,20-octahydro-21-methoxy- | B8 |
| 5,7-etheno-1H-[1,3]dioxolo[4,5-r]pyrimido[4,5-b][6,1,10,13]benzoxatriazacyclohexadecine, 9,10,11,12,13,14,15,16-octahydro-22-methoxy-12,15-dimethyl- | B9 |
| 5,7-etheno-13H-[1,3]dioxolo[4,5-r]pyrimido[4,5-b][6,1,10,13]benzoxatriazacyclohexadecin-13-one, 1,9,10,11,12,14,15,16-octahydro-22-methoxy-14,15-dimethyl-, (14S)- | B79 |
| 5,7-etheno-1H-[1,3]dioxolo[4,5-r]pyrimido[4,5-b][6,1,10,13]benzoxatriazacyclohexadecin-22-ol, 9,10,11,12,13,14,15,16-octahydro-15-methyl- | B11 |
| 4,6-etheno[1,3]dioxolo[4,5-q]pyrimido[4,5-b][6,1,12]benzoxadiazacyclopentadecine, 8,9,10,11,12,13,14,20-octahydro-13-methyl-21-[3-(4-methyl-1-piperazinyl)propoxy]- | B12 |
| 1-piperazineethanol, 4-[3-[(8,9,10,11,12,13,14,20-octahydro-13-methyl-4,6-etheno[1,3]dioxol[4,5-q]pyrimido[4,5-b][6,1,12]benzoxadiazacyclopentadecin-21-yl)oxy]propyl]- and | B13 |
| 5,7-etheno-1H-[1,3]dioxolo[4,5-r]pyrimido[4,5-b][6,1,10,13]benzoxatriazacyclohexadecine, 9,10,11,12,13,14,15,16-octahydro-15-methyl-22-[3-[4-(methylsulfonyl)-1-piperidinyl]propoxy]- | B14. |

13. The compound of formula (I) in claim 1, wherein the compound is a kinase inhibitor.

14. A pharmaceutical composition comprising a compound as claimed in claim 1.

15. A pharmaceutical composition comprising a pharmaceutically acceptable carrier and, as active ingredient, an effective kinase inhibitory amount of a compound as described in claim 1.

* * * * *

UNITED STATES PATENT AND TRADEMARK OFFICE
CERTIFICATE OF CORRECTION

PATENT NO. : 8,492,377 B2 Page 1 of 1
APPLICATION NO. : 12/373404
DATED : July 23, 2013
INVENTOR(S) : Papanikos et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 509 days.

Signed and Sealed this
Eighth Day of September, 2015

Michelle K. Lee
*Director of the United States Patent and Trademark Office*